(12) United States Patent
Isenberg et al.

(10) Patent No.: US 12,090,274 B2
(45) Date of Patent: Sep. 17, 2024

(54) NASAL VENTILATION MASK

(71) Applicant: Lisa M. Butler, Skillman, NJ (US)

(72) Inventors: Derek Lawrence Isenberg, Haddon Heights, NJ (US); James Wittes, Princeton, NJ (US); Philip J. Blyskal, Belmont, VT (US)

(*) Notice: Subject to any disclaimer, the term of this patent is extended or adjusted under 35 U.S.C. 154(b) by 0 days.

(21) Appl. No.: 17/814,602

(22) Filed: Jul. 25, 2022

(65) Prior Publication Data
US 2022/0355056 A1 Nov. 10, 2022

Related U.S. Application Data

(63) Continuation of application No. 17/356,289, filed on Jun. 23, 2021, now Pat. No. 11,426,551.

(60) Provisional application No. 63/175,774, filed on Apr. 16, 2021, provisional application No. 63/152,452, filed on Feb. 23, 2021, provisional application No. 63/042,896, filed on Jun. 23, 2020.

(51) Int. Cl.
  *A61M 16/06* (2006.01)
  *A61M 16/00* (2006.01)

(52) U.S. Cl.
  CPC .... *A61M 16/0616* (2014.02); *A61M 16/0084* (2014.02); *A61M 2210/0618* (2013.01)

(58) Field of Classification Search
  CPC .......... A61M 16/0616; A61M 16/0622; A61M 16/06–0694; A61M 2016/0661
  See application file for complete search history.

(56) References Cited

U.S. PATENT DOCUMENTS

| | | |
|---|---|---|
| 4,811,730 A | 3/1989 | Milano |
| D412,745 S | 8/1999 | Scheu |
| D431,077 S | 9/2000 | McGinnis et al. |
| 6,112,746 A | 9/2000 | Kwok et al. |
| 6,192,886 B1 | 2/2001 | Rudolph |
| D485,905 S | 1/2004 | Moore et al. |
| 6,729,333 B2 | 5/2004 | Barnett et al. |
| 7,007,696 B2 | 3/2006 | Palkon et al. |
| 7,255,107 B1 | 8/2007 | Gomez |
| D576,272 S | 9/2008 | Jones et al. |
| 7,451,764 B2 | 11/2008 | Wang |

(Continued)

FOREIGN PATENT DOCUMENTS

| | | |
|---|---|---|
| CA | 2662353 C | 2/2015 |
| CN | 210542787 U | 5/2020 |

(Continued)

*Primary Examiner* — Valerie L Woodward
(74) *Attorney, Agent, or Firm* — Schacht Law Office, Inc.; Paul J. Nykaza

(57) ABSTRACT

A nasal ventilation mask supplies breathing gas to an airway of a patient. The mask has a housing defining an internal cavity and having a peripheral end defining an end opening. The end opening is in fluid communication with the internal cavity. The end opening is configured to be positioned over an airway on a face of the patient. A sealing member is connected to the housing proximate the end opening. The sealing member extends towards the internal cavity and is configured to abut the face of the patient and deflect towards the internal cavity. The housing further defines a connector assembly having an opening in fluid communication with the internal cavity. The connector assembly is configured to be operably connected to a supply of breathing gas.

30 Claims, 40 Drawing Sheets

(56) References Cited

U.S. PATENT DOCUMENTS

| | | |
|---|---|---|
| 7,621,274 B2 | 11/2009 | Sprinkle et al. |
| 8,479,726 B2 | 7/2013 | McAuley |
| 8,596,273 B2 | 12/2013 | Burz et al. |
| 9,604,023 B2 | 3/2017 | Matula et al. |
| 9,629,975 B1 | 4/2017 | Pedro et al. |
| 10,166,354 B2 | 1/2019 | Eifler |
| 10,252,016 B2 | 4/2019 | Pedro et al. |
| 10,589,047 B2 | 3/2020 | Pedro et al. |
| 11,426,551 B1 | 8/2022 | Isenberg et al. |
| 2004/0065327 A1 | 4/2004 | Gradon et al. |
| 2007/0267021 A1 | 11/2007 | Kwok |
| 2008/0092895 A1 | 4/2008 | Birnkrant |
| 2008/0190432 A1* | 8/2008 | Blochlinger ...... A61M 16/0616 128/207.18 |
| 2008/0257338 A1 | 10/2008 | Gee-Turner |
| 2008/0295846 A1* | 12/2008 | Han ................ A61M 16/0858 128/207.13 |
| 2009/0187113 A1 | 7/2009 | Friedman et al. |
| 2012/0067349 A1* | 3/2012 | Barlow ............. A61M 16/0075 128/205.25 |
| 2012/0285452 A1 | 11/2012 | Amirav et al. |
| 2013/0008449 A1 | 1/2013 | Busch et al. |
| 2013/0199537 A1 | 8/2013 | Formica et al. |
| 2013/0312758 A1 | 11/2013 | Jones et al. |
| 2013/0340761 A1 | 12/2013 | Drew et al. |
| 2014/0144448 A1* | 5/2014 | Eifler ............... A61M 16/0616 128/206.24 |
| 2014/0158136 A1 | 6/2014 | Romagnoli et al. |
| 2014/0166018 A1 | 6/2014 | Dravitzki et al. |
| 2014/0174446 A1* | 6/2014 | Prentice ............ A61M 16/0825 128/205.25 |
| 2014/0174448 A1 | 6/2014 | Dravitzki et al. |
| 2014/0283843 A1* | 9/2014 | Eves ................ A61M 16/0616 128/206.24 |
| 2015/0157824 A1* | 6/2015 | Ho ........................ A61M 16/06 128/206.24 |
| 2015/0250971 A1 | 9/2015 | Bachelder et al. |
| 2016/0151222 A1 | 6/2016 | Pedro et al. |
| 2017/0014590 A1 | 1/2017 | Ritz et al. |
| 2017/0028149 A1 | 2/2017 | Pedro et al. |
| 2017/0087321 A1 | 3/2017 | Jordan et al. |
| 2017/0173290 A1 | 6/2017 | Pedro et al. |
| 2017/0246411 A1* | 8/2017 | Mashal ............ A61M 16/0605 |
| 2018/0021606 A1 | 1/2018 | Eisenkraft et al. |
| 2018/0133426 A1* | 5/2018 | Hallett .............. A61M 16/0644 |
| 2018/0250485 A1 | 9/2018 | Zhan et al. |
| 2019/0232012 A1 | 8/2019 | Pedro et al. |
| 2019/0314594 A1 | 10/2019 | Eifler |
| 2020/0114107 A1* | 4/2020 | Guney ............. A61M 16/0622 |
| 2020/0155782 A1 | 5/2020 | Swenson et al. |

FOREIGN PATENT DOCUMENTS

| | | |
|---|---|---|
| EP | 3233213 B1 | 9/2020 |
| FR | 2889073 A1 | 2/2007 |
| WO | 9925410 A1 | 5/1999 |
| WO | 2012176369 A1 | 12/2012 |

\* cited by examiner

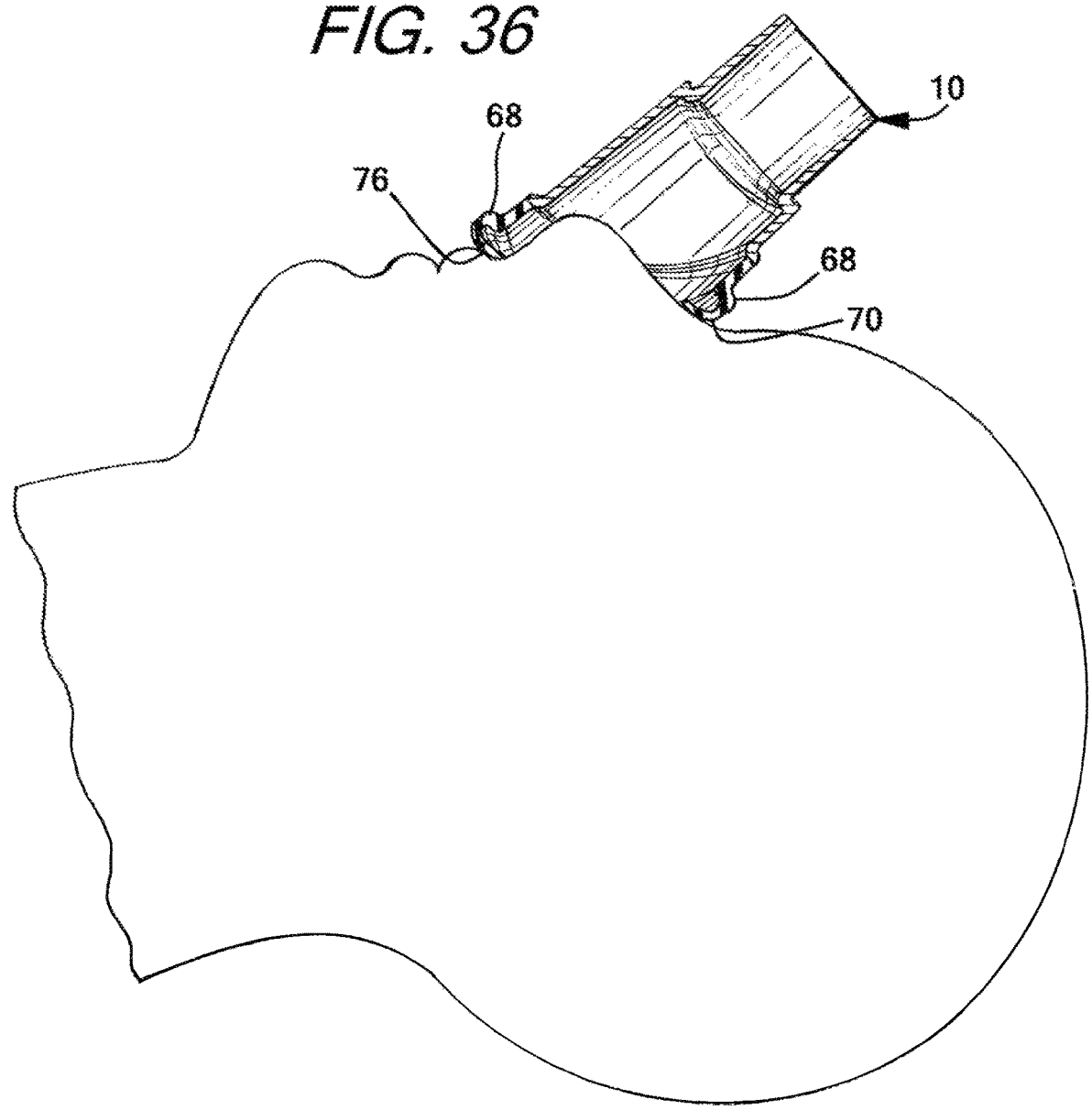

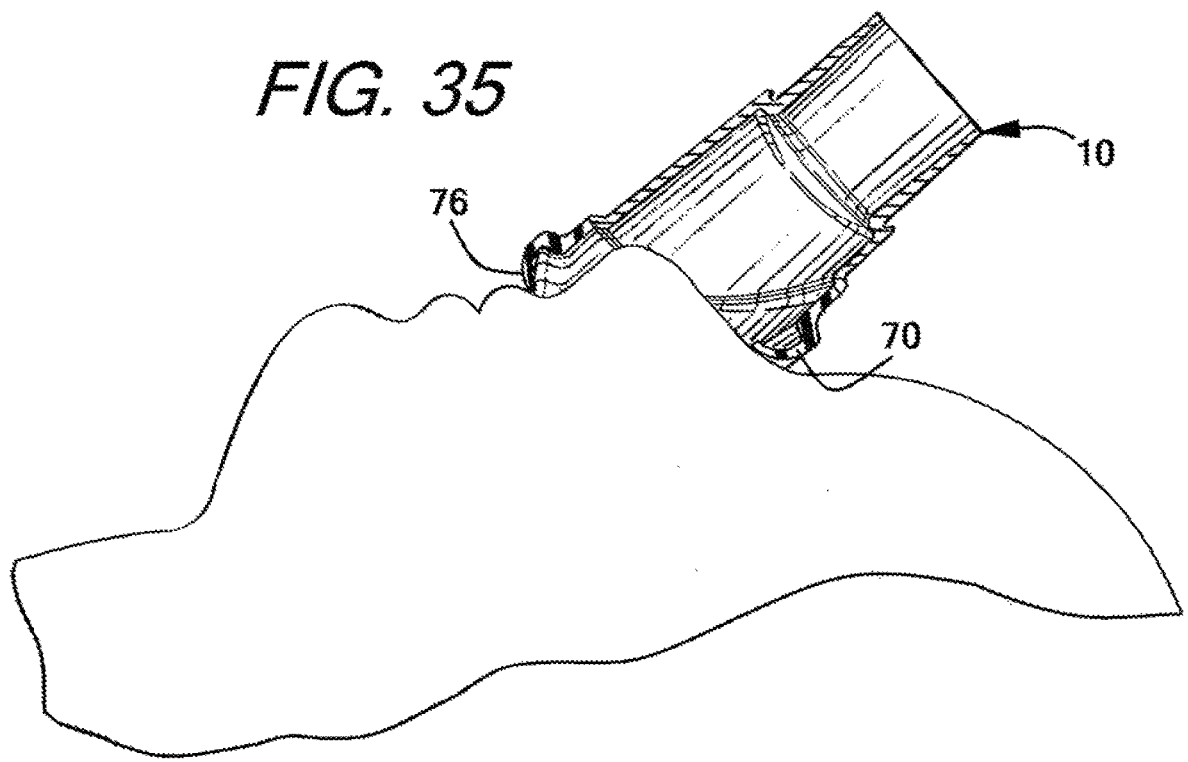
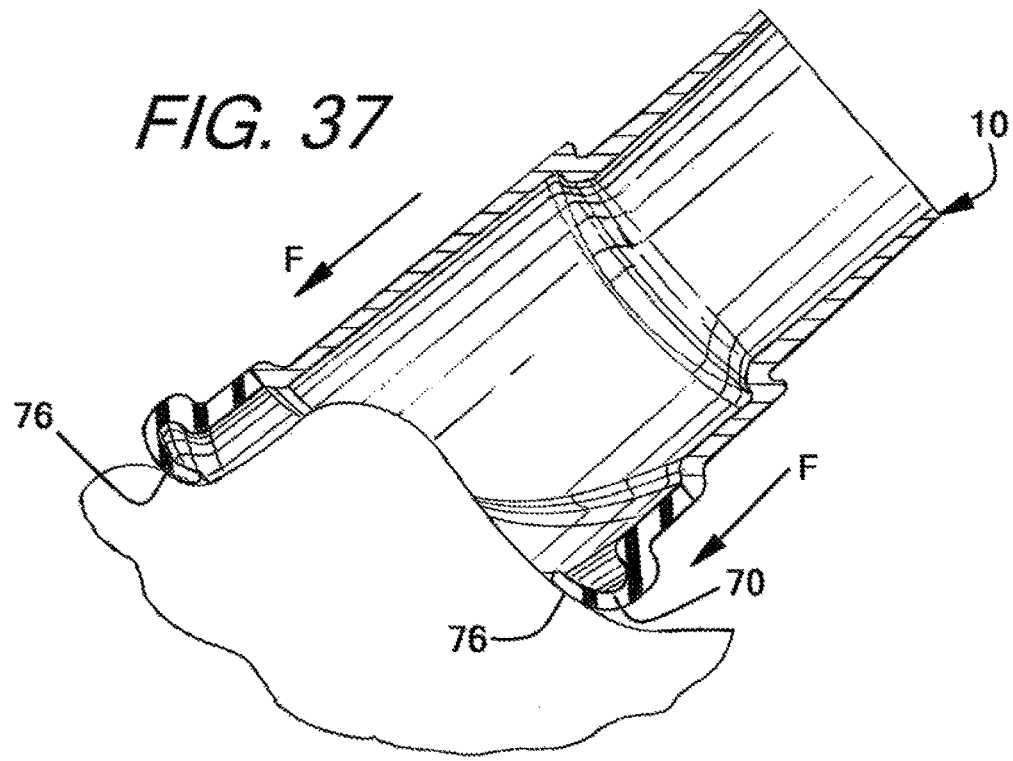

FIG. 68
FIG. 69
FIG. 70
FIG. 71
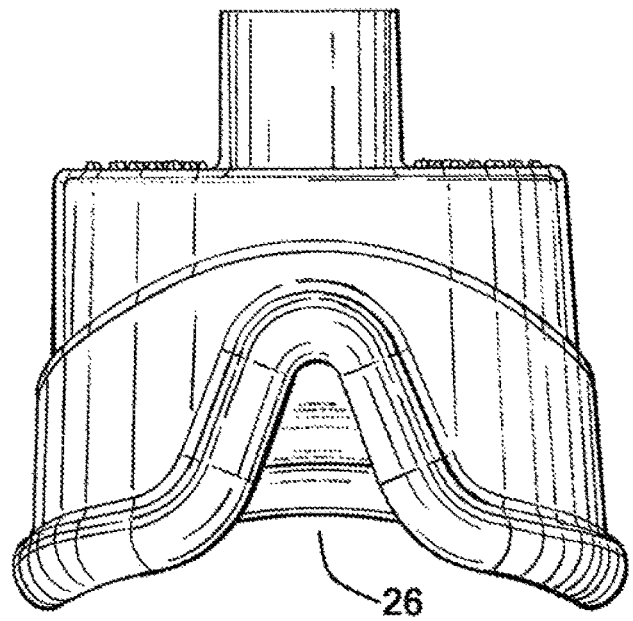
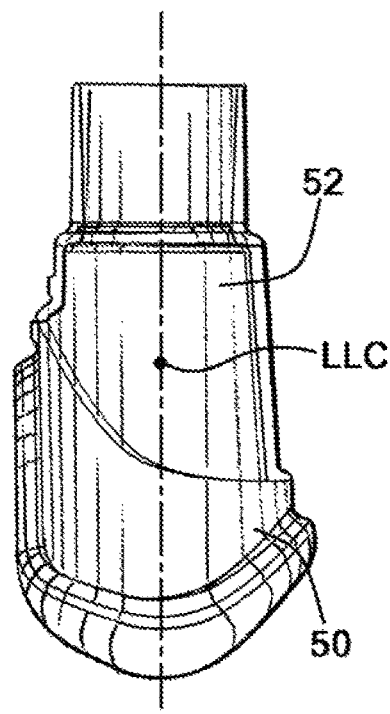
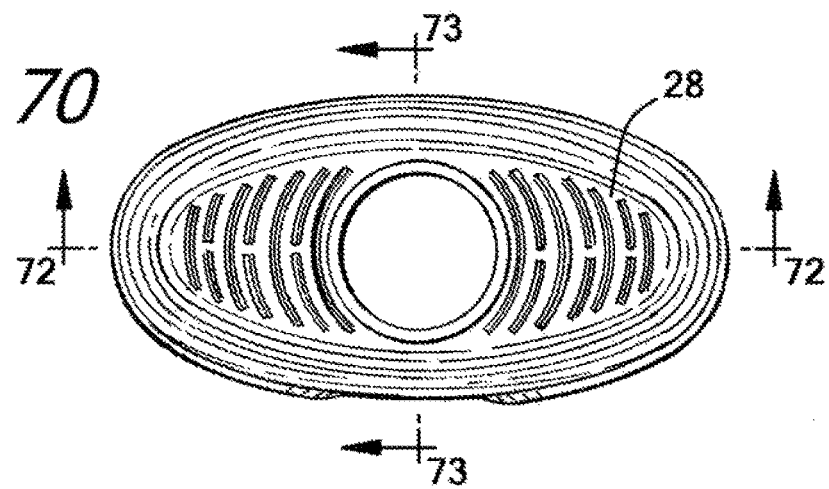
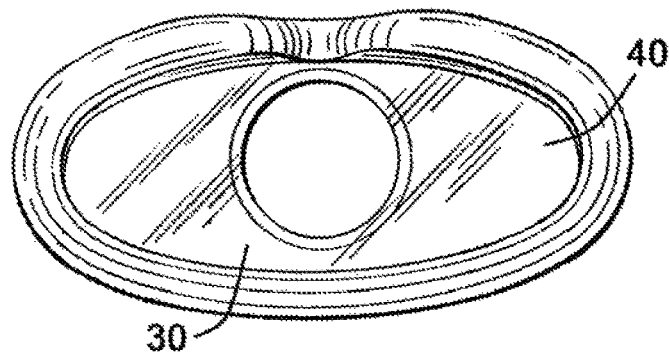

NASAL VENTILATION MASK

CROSS-REFERENCE TO RELATED APPLICATIONS

The present application is a continuation patent application of U.S. patent application Ser. No. 17/356,289, filed on Jun. 23, 2021, which application is incorporated by reference herein in its entirety.

FEDERALLY SPONSORED RESEARCH OR DEVELOPMENT

None.

TECHNICAL FIELD

The invention relates generally to a respiratory mask and, in particular, a nasal ventilation mask for use with a manual resuscitator for ventilation of a patient.

BACKGROUND OF THE INVENTION

Manual resuscitators, or manual resuscitator bag assemblies, or artificial manual breathing units are known in the art and used in medical settings. These devices are sometimes referred to as bag valve masks or breathing units as well. Artificial manual breathing units and manual resuscitator bag assemblies incorporate a face mask to cover the nose and/or mouth of a patient for ventilation (supplying breathing gas to lungs of a patient). Trained medical personnel such as doctors, nurses, paramedics or emergency medical technicians, resuscitators or other emergency responders use the breathing unit as a medical tool to supply breathing gas to an airway of a patient, e.g., to force air into the lungs of the patient who is not breathing or is not breathing adequately and needs assistance.

As shown in FIGS. 1 and 2, such manual resuscitators, designated with the reference numeral 1, typically include a squeezable, inflatable bag 2, and a face mask 3 operably connected to the bag 2. FIGS. 1 and 2 show prior art manual resuscitator bag assemblies. In addition to being connected to the face mask 3, the bag 2 can also have a tube(s) that can be connected to an oxygen source to be used if desired. The face mask 3 may have an inflatable seal portion 4 designed to be pressed against the patient's face when the face mask 3 is place over the patient's mouth and nose. FIG. 2 shows a medical worker using the bag assembly 1 on a patient and squeezing the inflatable bag 2 to force air into the lungs of the patient. Emergency responders are trained in the use of the manual resuscitator devices as further injury or even death to the patient can result if the device not used properly.

In many manual resuscitator bag assembly designs, it is difficult for medical personnel to achieve a tight seal against the patient's face. Certain mask designs make it difficult for medical personnel or emergency responders to engage the mask to assist in creating a tight seal. In certain uses, multiple workers may be required to successfully use the device. A less than tight seal prevents proper operation of the manual resuscitator. In other designs, the face masks have more complex multi-component designs that are more rigid, costly and cumbersome to use. Other face masks are designed to cover both a nasal airway and an oral airway resulting in other difficulties if medical personnel require access to the oral airway while still being able to deliver oxygen to the nasal airway.

While such face masks used with manual resuscitators according to the prior art provide a number of advantageous features, they nevertheless have certain limitations. The present invention is provided to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY OF THE INVENTION

The present invention provides a nasal ventilation mask for use with an artificial manual breathing unit or manual resuscitator bag assembly for ventilation of a patient.

According to a first aspect of the invention, a ventilation mask for supplying breathing gas to an airway of a patient has a housing having a sidewall defining an internal cavity and having a peripheral end defining an end opening. The end opening is in fluid communication with the internal cavity, and the end opening configured to be positioned over an airway on a face of a patient. A sealing member is connected to the housing proximate the end opening and remote from the sidewall. The sealing member extends towards the internal cavity, and the sealing member is configured to abut the face of the patient and deflect towards the internal cavity. The housing further defines a connector assembly having an opening in fluid communication with the internal cavity. The connector assembly is configured to be operably connected to a supply of breathing gas.

According to another aspect of the invention, the sealing member of the mask forms an inwardly curled lip member extending into the internal cavity. The lip member has an outer surface configured to abut the face of the patient. The lip member has a proximal end and a distal end, and the lip member has a thickness being tapered towards the distal end. The housing defines an internal surface wherein an imaginary line extends from the internal surface past the end opening. A distal end of the lip member extends past the imaginary line. An outer surface of the inwardly curled lip is smooth and uninterrupted. In addition, the outer surface of the inwardly curled lip has a convex shape.

According to a further aspect of the invention, the housing has a reinforcing member extending therefrom proximate the end opening. The reinforcing member has an outer end, wherein the sealing member defines an inwardly curled lip member having a proximal end depending from the outer end of the reinforcing member. The lip member has a thickness that is tapered towards the distal end. In addition, the housing, reinforcing member and lip member comprise an integral structure.

According to another aspect of the invention, the housing comprises a housing body segment operably connected to a connector segment defining a circumferential connection joint. The housing further defines a front wall section opposite a rear wall section and a first end wall section extending between the front wall section and the rear wall section. The connection joint extends along a downwardly curved path on the first end wall section from the front wall section towards the rear wall section.

According to a further aspect of the invention, the connection joint on the first end wall section has a curved segment adjacent a substantially horizontal segment proximate the rear wall section.

According to another aspect of the invention, the housing body segment defines a lower sidewall segment and the connector segment defines an upper sidewall segment. The upper sidewall segment is positioned inwardly offset from the lower sidewall segment. In addition, the lower sidewall segment has a first thickness and the upper sidewall segment has a second thickness. The first thickness is greater than the second thickness.

According to another aspect of the invention, the connection joint is a butt joint formed between the housing body segment and the connector segment. A chemical bond is formed between the materials of the housing body segment and the connector segment. In an alternative configuration, the connection joint is comprised of a tongue on one of the housing body segment and the connector segment and a groove on the other of the housing body segment and the connector segment.

According to a further aspect of the invention, the housing body segment is of a thermoplastic polyurethane material. The connector segment is of an acrylonitrile butadiene styrene material.

According to yet another aspect of the invention, housing defines a gripping member thereon. The gripping member is a ridge or a plurality of ridges on a shoulder of the housing. The gripping member can also be a plurality of protrusions, the protrusions in the form of truncated cones.

According to a further aspect of the invention, the end opening defines a substantially oval footprint.

According to another aspect of the invention, the housing has a plurality of longitudinal ribs spaced thereon.

According to another aspect of the invention, the housing further defines a slot, the slot being in fluid communication with the end opening. When the end opening is configured to be placed over a nasal cavity of a patient, the slot is dimensioned to be positioned proximate a dorsal base of a nose of the patient.

According to yet another aspect of the invention, the housing further defines a slot, the slot being in fluid communication with the end opening. The lip member extends around a full peripheral of the end opening and slot.

According to another aspect of the invention, a ventilation mask supplies a breathing gas to an airway of a patient. The ventilation mask has a housing defining an internal cavity and having a peripheral end defining an end opening. The end opening is in fluid communication with the internal cavity, and the end opening is configured to be positioned over an airway on a face of a patient. The peripheral end of the housing has a sealing member configured to abut a face of the patient. The housing further defines a front wall section, a rear wall section and opposite end wall sections extending between the front wall section and the rear wall section. The housing comprises a housing body segment operably connected to a connector segment defining a circumferential connection joint around the housing. On the opposite end wall sections the connection joint has segments sloping downwardly along a curved path from the front wall section towards the rear wall section. The connector segment has an inlet opening in fluid communication with the internal cavity. The connector segment is configured to be operably connected to a supply of breathing gas.

According to a further aspect of the invention, a ventilation mask supplies breathing gas to an airway of a patient. The ventilation mask has a housing defining an internal cavity and having a peripheral end defining an end opening, the end opening being in fluid communication with the internal cavity. The end opening is configured to be positioned over an airway on a face of a patient. The peripheral end of the housing has an inwardly curled lip extending towards the internal cavity, the inwardly curled lip configured to abut the face of the patient and deflect towards the internal cavity. The housing further defines a front wall section, a rear wall section and opposite end wall sections extending between the front wall section and the rear wall section. The housing further comprises a housing body segment operably connected to a connector segment defining a circumferential connection joint around the housing. On opposite end wall sections, the connection joint has segments sloping downwardly along a curved path from the front wall section towards the rear wall section. The connector segment has an inlet opening in fluid communication with the internal cavity, the connector segment configured to be operably connected to a supply of breathing gas.

According to another aspect of the invention, a nasal ventilation mask supplies breathing gas to a nasal airway of a patient. The nasal ventilation mask has a housing defining an internal cavity and comprising a housing body segment of flexible thermoplastic polyurethane material operably connected to a connector segment of rigid acrylonitrile butadiene styrene material defining a circumferential connection joint. The housing body segment defines a distal end defining an end opening in fluid communication with the internal cavity. The housing body segment further defines a slot, the slot being in fluid communication with the end opening. The distal end has a sealing member positioned around the end opening and slot. The sealing member forms an inwardly curled lip member extending into the internal cavity. The housing body segment further has a reinforcing member extending therefrom proximate the distal end. The reinforcing member has an outer end wherein a proximal end of the lip member depends from the outer end of the reinforcing member. The connector segment has a receiver member defining an inlet opening in communication with the internal cavity. On opposite end wall sections of the housing, the circumferential connection joint has segments extending along a conic curve towards the distal end, wherein a location proximate a central portion of each end wall section of the housing is positioned on the connector segment. The nasal ventilation mask is configured to be pressed against a face of the patient wherein the lip member is configured to engage the face of the patient and deflect into the internal cavity and configured to create a seal between the face of the patient and the lip member, and wherein the slot is dimensioned to be positioned proximate a dorsal base of a nose of the patient. An inflatable bag of a manual resuscitator bag assembly is configured to be operably connected to the inlet opening of the receiver member of the connector segment wherein breathing gas is delivered to the nasal airway of the patient.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 35 is cross-sectional side elevation view of the nasal ventilation mask positioned on the face of a patient;

FIG. 36 is an cross-sectional side elevation view of the nasal ventilation mask positioned on the face of the patient and pressed against the face of the patient;

FIG. 37 is an enlarged cross-sectional side view of the nasal ventilation mask positioned on and pressed against the face of the patient;

FIG. 68 is a front elevation view of the nasal ventilation mask of FIG. 66;

FIG. 69 is a side elevation view of the nasal ventilation mask of FIG. 66, the opposite side elevation view being the same;

FIG. 70 is a top plan view of the nasal ventilation mask of FIG. 66;

FIG. 71 is a bottom plan view of the nasal ventilation mask of FIG. 66;

DETAILED DESCRIPTION OF THE PREFERRED EMBODIMENTS

Figure 1:
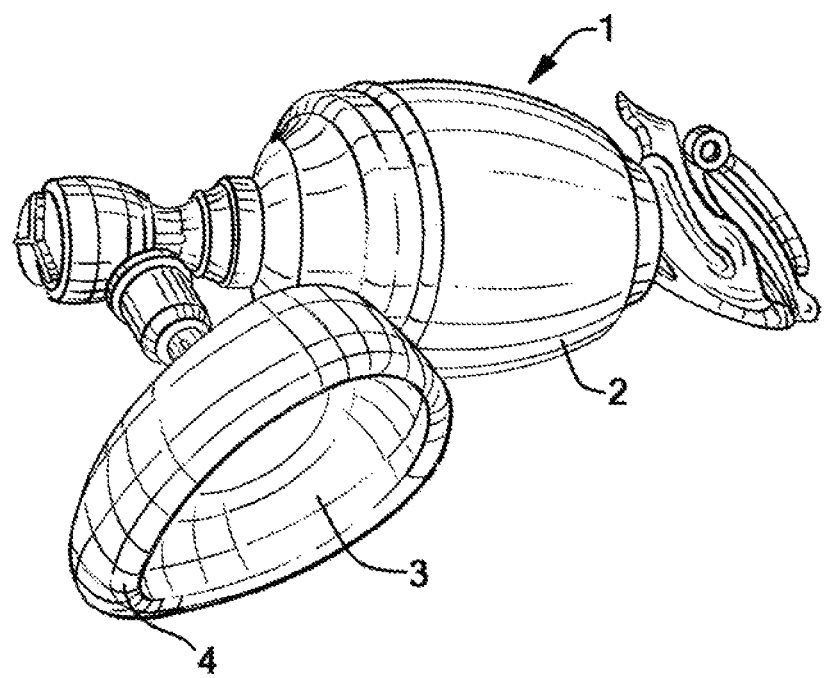
FIG. 1 is a perspective view of a prior art manual resuscitator bag assembly.
Figure 2:
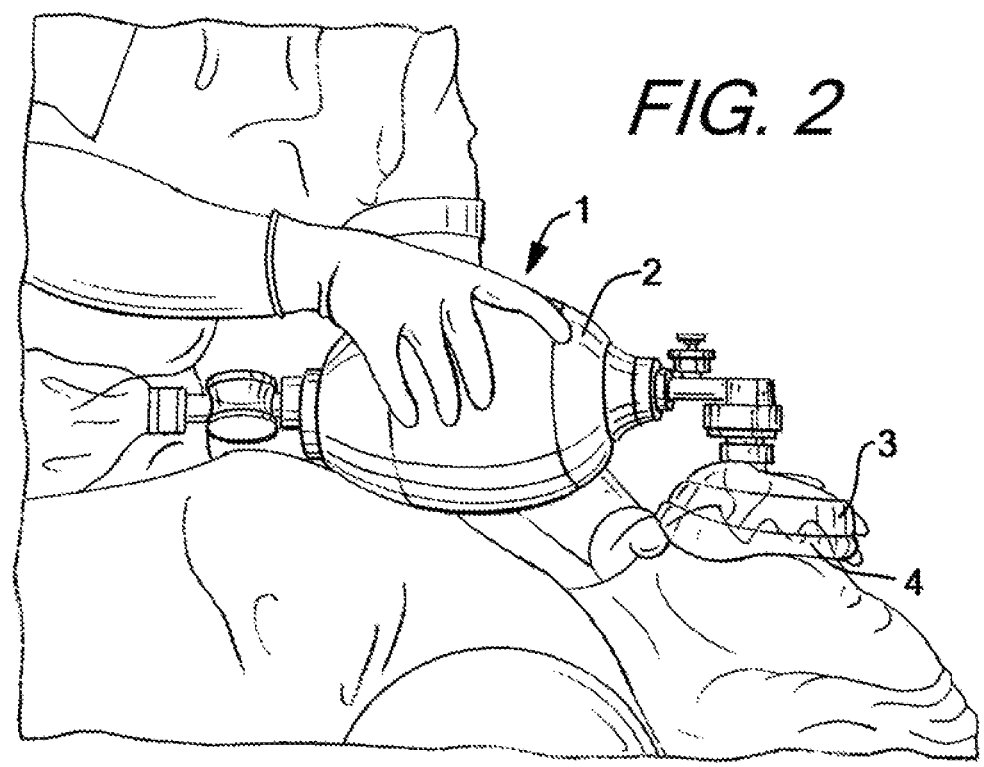
FIG. 2 is a schematic side elevation view of a medical worker using a prior art manual resuscitator bag assembly on a patient.

While this invention is susceptible of embodiments in many different forms, there are shown in the drawings and will herein be described in detail preferred embodiments of the invention with the understanding that the present disclosure is to be considered as an exemplification of the principles of the invention and is not intended to limit the broad aspect of the invention to the embodiments illustrated.

Figure 3:
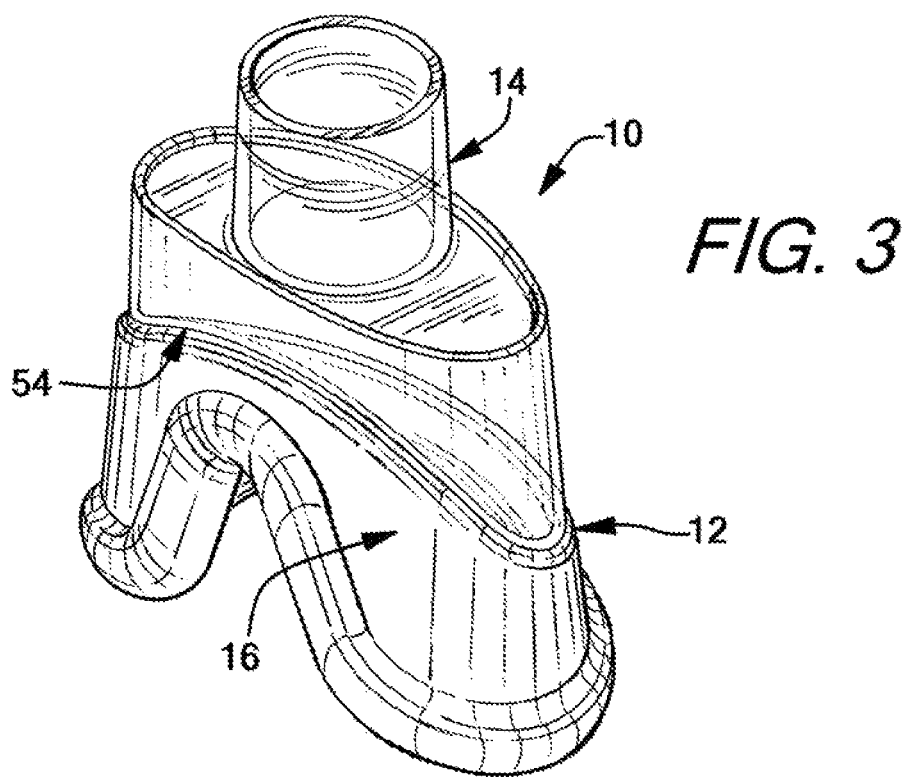
FIG. 3 is a front perspective view of a nasal ventilation mask according to an exemplary embodiment of the present invention.

Referring to the drawings, FIG. 3 shows a perspective view of a nasal ventilation mask according to an exemplary embodiment of the invention. It is understood that the nasal ventilation mask is used as part of a manual resuscitator device to deliver a supply of breathing gas such as oxygen to a patient as described above. The structure of the nasal ventilation mask will be described followed by a description of operation of the nasal ventilation mask on a patient such as by an emergency responder, resuscitator or other medical worker. It is further understood that the nasal ventilation mask may be referred to as a nasal mask, face mask, respiratory mask, ventilation mask or other apparatus for supplying breathing gas. It is further understood that features of the mask can apply to other breathing-type masks. Features of the mask can be used in masks designed to cover both an oral airway and nasal airway or just one airway.

In a first exemplary embodiment, the nasal ventilation mask is shown in FIGS. 3-32 and is designated with the reference numeral 10. The nasal ventilation mask 10 generally includes a housing body 12 and a connector assembly 14. It is understood that in one exemplary embodiment, the nasal ventilation mask 10 can have a single, one-piece integral configuration having a sidewall and other components. In such a configuration, the housing body 12 is integral with the connector assembly 14. In a further exemplary embodiment, the nasal ventilation mask 10 has a multi-component configuration such as shown in FIGS. 3-32 wherein multiple components are operably connected together. General structural configurations of the nasal ventilation mask 10 are described herein, and structures of the multiple components that form the mask 10 and respective connection details are also described herein for the exemplary embodiment of FIGS. 3-32.

As further shown in FIGS. 3-11, the nasal ventilation mask has a housing body 12 wherein the connector assembly 14 operably extends from the housing body 12. The housing body 12 has a sidewall 16 that extends fully around the housing 12. The sidewall 16 may be referred to as a circumferential sidewall 16 having a contoured configuration. The sidewall 16 may also be referred to as an annular sidewall 16 while not necessarily having a circular cross-section. In this exemplary embodiment, the circumferential sidewall 16 has a generally oval cross-section to be further described below. As further shown in FIGS. 5-11, the sidewall 16 of the housing 12 has a front wall section 18, a rear wall section 20, a first end wall section 22 and a second end wall section 24. In an exemplary embodiment, the rear wall section 20, the first end wall section 22 and the second end wall section 24 are generally plain and uninterrupted and void of any openings therethrough. It is understood that the front wall section 18 is generally opposite the rear wall section 20. The first end wall section 22 and generally opposite to the second end wall section 24. The end wall sections 22,24 extend between the front wall section 18 and the rear wall section 24. As the sidewall 26 has a contoured configuration, it is understood the wall sections 18-24 smoothly transition from wall section to the next adjacent wall section circumferentially around the mask 10. The front wall section 18 of the sidewall 16 further defines a slot 26 to receive a portion of a nose of a patient to be further described. The slot 26 has a slot height SH also to be further described (FIG. 14) and it is understood the lower end of the slot 26 can be measured at different locations. The housing 12 further has a top wall 28 operably connected to the sidewall 16. In this exemplary embodiment, the top wall 28 is generally transverse to the sidewall 16 although the top wall 28 can have some curvature. The housing 12 defines an internal cavity 30 wherein the sidewall 16 and top wall 28 cooperate to define the internal cavity 30. Proximate generally an interface area between the top wall 28 and the end wall sections 22,24, the housing 12 defines a first shoulder 32 and a second shoulder 34. It is understood the shoulders 32,34 can be positioned on the top wall 28 or also a combination of the top wall 28 and adjacent sections of the sidewall 16. The shoulders 32,34 are generally rigid in construction and are engaged by an emergency responder or medical worker when using the nasal mask 10 to provide an enhanced seal as described in greater detail below.

The housing 12 further has a peripheral end 36 or a distal end 36 wherein the housing 12 has a sealing member 38 proximate the distal end 36. The sealing member 38 has structures for sealing against a face of a patient. The sealing member 38 is an air pressure sealing member so that air pressure in the internal cavity 30 of the mask 10 is not lost through the seal to be described in greater detail below. At the peripheral end 36 or distal end 36, the housing 12 defines a distal end opening 40. The end opening 40 is in fluid communication with the internal cavity 30. It is understood that the end opening 40 is further in fluid communication with the slot 26. The slot 26 has a height dimensioned to only extend to a dorsal base of a patient's nose as opposed to reaching the dorsal bridge of the nose as explained in greater detail below. The distal end opening 40 is placed over a nasal airway of a patient and the slot 26 is positioned over the nose to be described in greater detail below. As will be further described below, the sealing member 38 extends around a fully periphery of the end opening 40 and including the slot 26.

As further shown in FIGS. 5-11, the connector assembly 14 extends from a proximal end of the housing 12 and is generally located opposite the distal end 36 of the housing 12. In one exemplary embodiment, the connector assembly includes a receiver member 42. The receiver member 42 is a generally a slight conical tube member that extends from the top wall 28 of the housing 12. The receiver member 42 defines an internal conduit 44 that is in fluid communication with the internal cavity 30. The receiver member 42 further has an inlet opening 46 in fluid communication with the internal conduit 44. The receiver member 42 is dimensioned to be operably connected to an inflatable bag of a manual resuscitator bag assembly to be described in greater detail below. It is understood that there is fluid communication from the inlet opening 46, the internal conduit 44, internal cavity 30 and distal end opening 40, thereby defining a passageway for a breathing gas to flow through the mask 10 as further described below. Furthermore, this passageway is generally an inline configuration traveling linearly through the mask 10.

As discussed, the nasal ventilation mask 10 of FIGS. 3-32 is formed from multiple components in one exemplary embodiment of the invention. The nasal ventilation mask 10 has a two-piece construction. The nasal mask 10 has a housing body segment 50 and a connector segment 52. The housing body segment 50 is operably connected to the connector segment 52 wherein the housing body 12 and the connector assembly 14 are formed as described above. Once connected as shown for example in FIGS. 3-4, the nasal ventilation mask 10 has a connection joint 54 defined therebetween and generally has the same structures and function as described herein. The connection joint 54 will be described in greater detail below.

Figure 16:
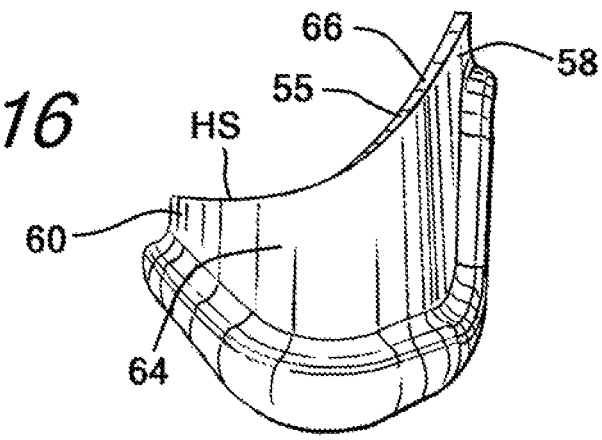
FIG. 16 is a side elevation view of the housing body segment of the nasal ventilation mask of FIG. 3, the opposite side elevation view being the same.

FIGS. 12-21 further show the housing body segment 50. The housing body segment 50 generally forms a lower portion of the nasal ventilation mask 10, and thus defines, among other structures, the distal end 36 of the mask 10 as well as the sealing member 38. The housing body segment 50 has a lower sidewall segment 56 that forms the lower portion of the sidewall 16 of the housing 12. The lower sidewall segment 56 defines an internal area that will cooperate to form the internal cavity 30. The lower sidewall segment 56 also defines a front wall section 58, a rear wall section 60, a first end wall section 62 and a second end wall section 64. It is understood that the wall sections 58-64 cooperate with other wall sections to be described to form the wall sections 18-24 of the mask 10 previously described. The front wall section 58 contains the slot 26 wherein the slot 26 is defined completely in the front wall section 58. As further shown, the front wall section 58 has a greater height/length dimension than the rear wall section 60. The front wall section 58 has a convex upper perimeter. The lower sidewall segment 56 has a proximal end that defines a first connection surface 66 and facing upwards and away from the distal end 36. It is understood that the first connection surface 66 could take various configurations such as a combination of planar and angled surfaces. As can be appreciated from FIGS. 12-16, the first connection surface 66 has a greater height from the distal end 36 at the front wall section 58 than a height of the first connection surface 66 from the distal end 36 at the rear wall section 60. In addition, the first connection surface 66 slopes downwardly from the front wall section 58 towards the rear wall section 60 along a curved path. The first connection surface 66 may be considered to slope along generally a conic curve. At proximate a lateral midpoint of the housing body segment 50 between the front wall section 58 and the rear wall section 60, the first connection surface 66 has a generally horizontal configuration HS towards the rear wall section 60. Thus, as shown in FIG. 16, the first connection surface 66 has a sloped segment SS from the front wall section 58 and a generally horizontal segment HS towards the rear wall section 60. As further shown in FIGS. 19-20, the lower sidewall segment 56 has a first thickness $t_1$, wherein the first thickness $t_1$ is 0.070 inches in one exemplary embodiment. It is understood that the thickness can be varied. For example, in another exemplary embodiment, the lower sidewall segment 56 could have a thickness of 0.125 inches.

Figure 19:
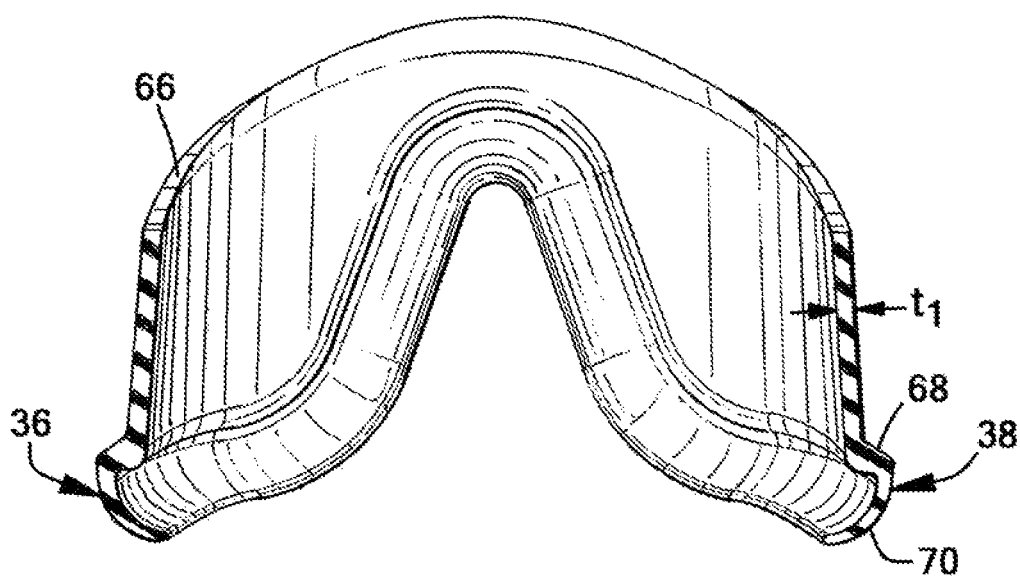
FIG. 19 is a cross-sectional view taken along lines 19-19 of FIG. 17.
Figure 20:
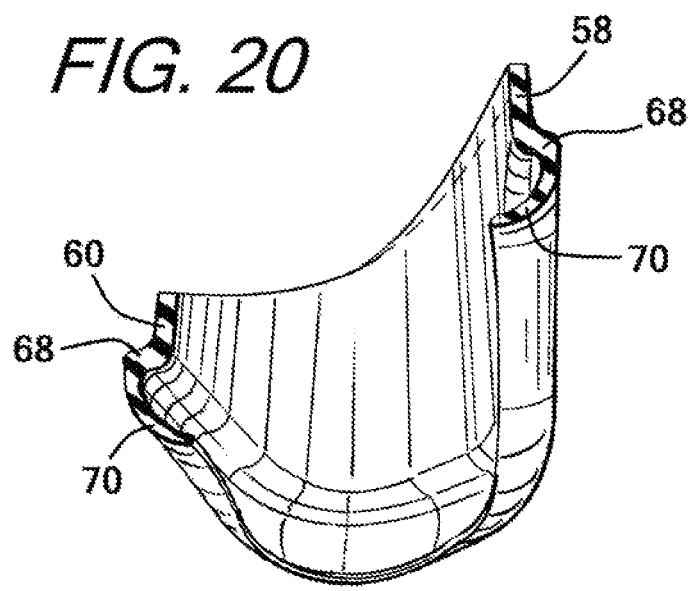
FIG. 20 is a cross-sectional view taken along lines 20-20 of FIG. 17.
Figure 21:
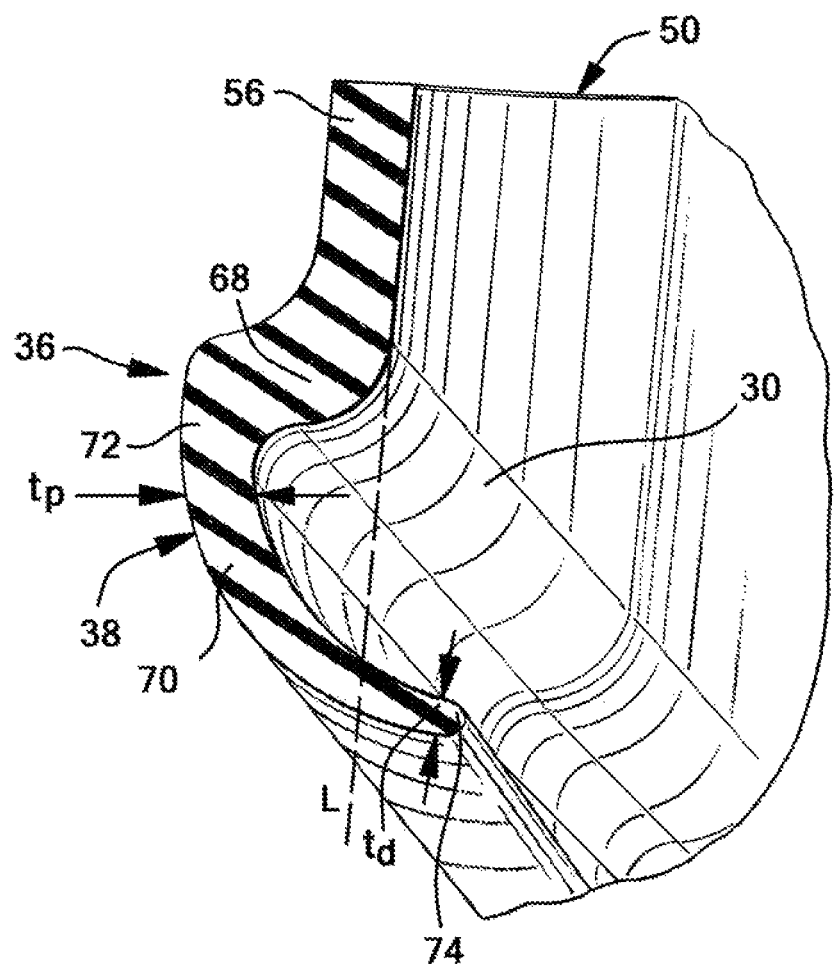
FIG. 21 is a partial enlarged cross-sectional view of a distal end of the housing body segment of the nasal ventilation mask of FIG. 3.
Figure 21A:
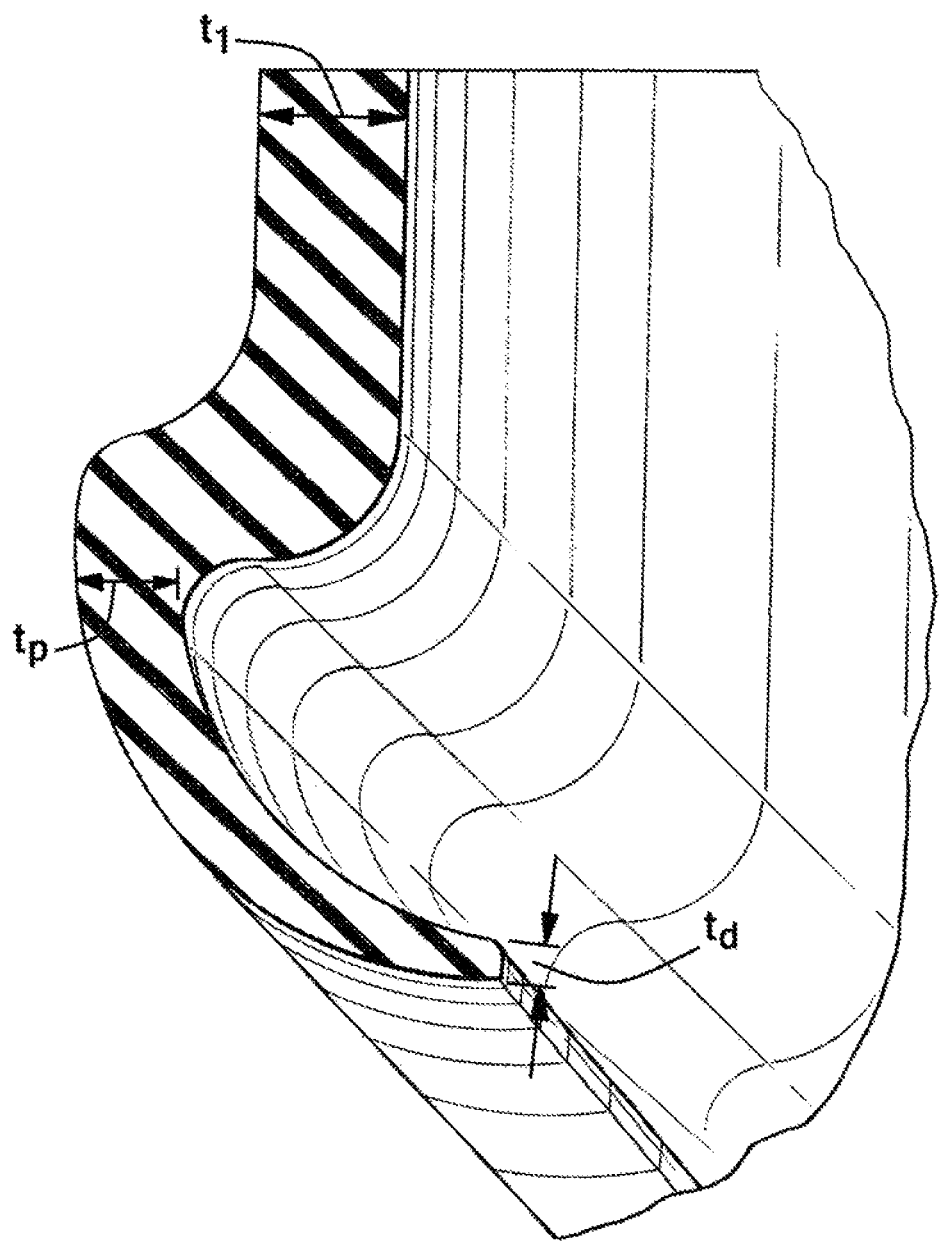
FIG. 21A is a partial enlarged cross-sectional view of the distal end of the housing body segment as shown in FIG. 21 and showing additional detail.
Figure 22:
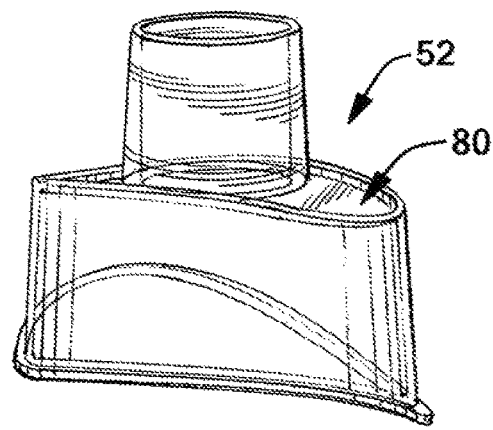
FIG. 22 is a front perspective view of a connector segment of the nasal ventilation mask of FIG. 3.
Figure 23:
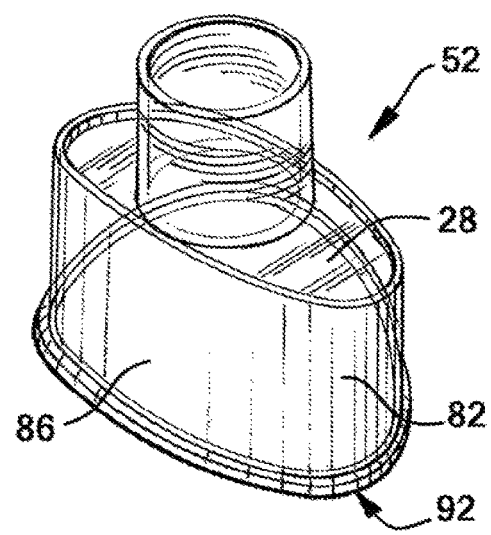
FIG. 23 is a rear perspective view of the connector segment of the nasal ventilation mask of FIG. 3.
Figure 24:
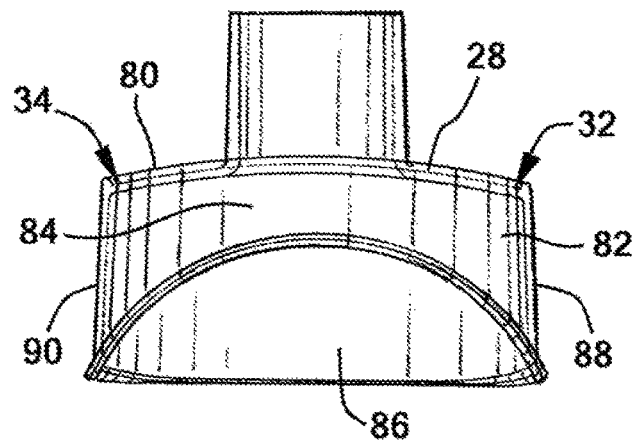
FIG. 24 is a front elevation view of the connector segment of the nasal ventilation mask of FIG. 3.
Figure 25:
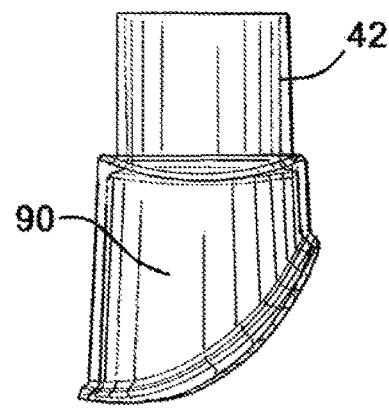
FIG. 25 is a side elevation view of the connector segment of the nasal ventilation mask of FIG. 3, the opposite side elevation view being the same.
Figure 26:
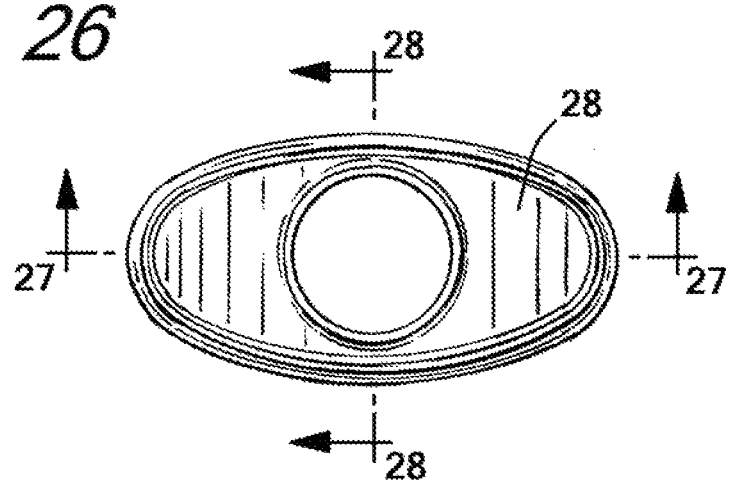
FIG. 26 is a top plan view of the connector segment of the nasal ventilation mask of FIG. 3.

FIGS. 19-21 further show additional structure and detail at the peripheral end 36 or the distal end 36 of the housing body segment 50. At proximate the distal end 36, the housing body segment 50 has a reinforcing member 68 extending from an outer surface of the lower sidewall segment 56. Thus, the reinforcing member 68 is generally normally to the lower sidewall segment 56 and has a cantilevered configuration (FIG. 21). As further shown in FIG. 21A, the reinforcing member 68 can have an upper surface having a radius at an interface with the outer surface of the sidewall 16 wherein an angle of 15° is formed as shown. The reinforcing member 68 can still be considered generally or approximately normal or transverse to the sidewall 16 of the housing 12. FIGS. 21 and 21A further show that in this configuration, the sealing member 38 and lip member 70, while being connected to the housing 12 proximate the end opening 40, the sealing member 38 is remote from the sidewall 16 via the reinforcing member 68. The reinforcing member 68 may have a thickness of approximately 0.090 inches and extend outwardly from the sidewall 16 approximately 0.10 inches in an exemplary embodiment. In a further exemplary embodiment, the reinforcing member 68 is integral with the housing body segment 50. As described in greater detail below, as the housing body segment 50 is formed of a more flexible material, the reinforcing member 68 provides an amount of rigidity in certain areas of the mask 10 to resist buckling as desired. As further shown in FIGS. 19-21, the housing body segment 50 has the sealing member 38 at the distal end 36. In particular, the sealing member 38 depends from an outer end of the reinforcing member 68. The sealing member 38 has a lip member 70. The lip member 70 has a proximal end 72 integrally connected to the outer end of the reinforcing member 68. The lip member 70 is inwardly curled wherein a distal end 74 of the lip member 70 extends towards the internal cavity 30, and into the internal cavity 30 in an exemplary embodiment. The lip member 70 has a proximal thickness $t_p$ at the proximal end 72. The lip member 70 is tapered towards the distal end 74 wherein the distal end 74 of the lip member 70 has a distal thickness $t_d$. The distal thickness $t_d$ is less than the proximal thickness $t_p$. It is understood that the thickness of the lip member 70 gradually decreases towards the distal end 74 of the lip member 70. As further shown in FIG. 21, the housing body segment 50 defines an inner surface (and an inner surface of the sidewall 16) and an imaginary line L extends from the inner surface and beyond the distal end 36. The lip member 70 extends past the imaginary line L wherein the distal end 74 of the lip member 70 extends past the imaginary line L and towards the internal cavity 30. It is understood that the length of the lip member 70 can vary wherein the distal end 74 of the lip member 70 extends just to the imaginary line L or short of the imaginary line L. As described, the lip member 70 depends from an outer end of the reinforcing member 68. In particular, the proximal end 72 depends from the free cantilevered end of the reinforcing member 68. Thus, the proximal end of the lip member 70 is generally offset from the lower sidewall segment 56 as well as the overall sidewall 16 of the mask 10. The proximal end 72 of the lip member 70 is outwardly offset from the lower sidewall segment 56 and further remote from the internal cavity 30. In other exemplary embodiments, the lip member 70 can be aligned with the lower sidewall segment 56. In an exemplary embodiment, the housing body segment 50 or sidewall 16, the reinforcing member 68 and the lip member 70 are all integral with one another. As further shown in FIGS. 21 and 21A, the lip member 70 has an outer surface 76 that engages a face of the patient in use to be described. The outer surface 76 of the lip member 70 has a generally convex shape and is generally smooth and uninterrupted. In one exemplary embodiment, the proximal end thickness $t_p$ is 0.060 inches or in the range of 0.040-0.080 inches, and the distal end thickness $t_d$ is 0.025 inches or in the range of 0.015-0.040 inches. The thicknesses of the lip member 70 can vary depending on various factors such as sealing requirements or the durometer of the material of the lip member 70.

Thus, as can be appreciated from FIGS. 19-21, the reinforcing member 68 is generally incorporated with the sealing member 38 and, in particular, the lip member 70. The reinforcing member 68 extends generally transverse to the lower sidewall segment 56 and sidewall 16 of the mask 10. The reinforcing member 68 is incorporated into, or integrated into an outer end of the sidewall 16. The inwardly curled lip member 70 depends from the reinforcing member 68 and extends into the internal cavity 30. In this configuration, the lip member 70 of the sealing member 38 is connected proximate the end opening of the housing 12 but remote from the sidewall 16 as the lip member 60 is positioned outwardly away from the sidewall 16. Further in this configuration, the reinforcing member 68 and lip member 70 provide an integrated reinforcing structure that minimizes potential floppiness in the mask 10. Such integration provides a cleaner, enhanced design as well for allowing more efficient resin flow in the mold when forming the component. In addition, the depending and cantilevered configuration enhances the seal achieved by the lip member 70 in providing smooth inward deflection of the lip member 70.

Figure 17:
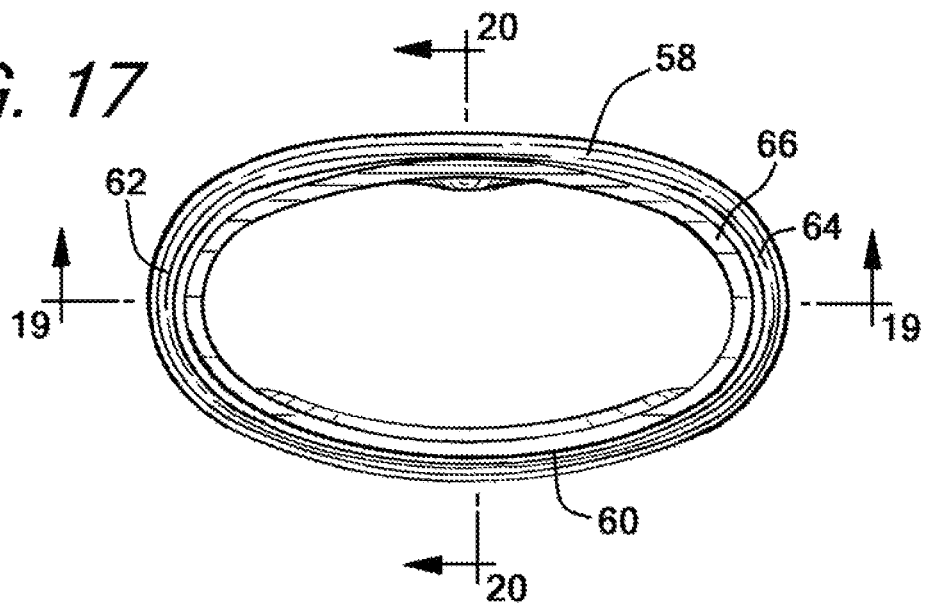
FIG. 17 is a top plan view of the housing body segment of the nasal ventilation mask of FIG. 3.
Figure 18:
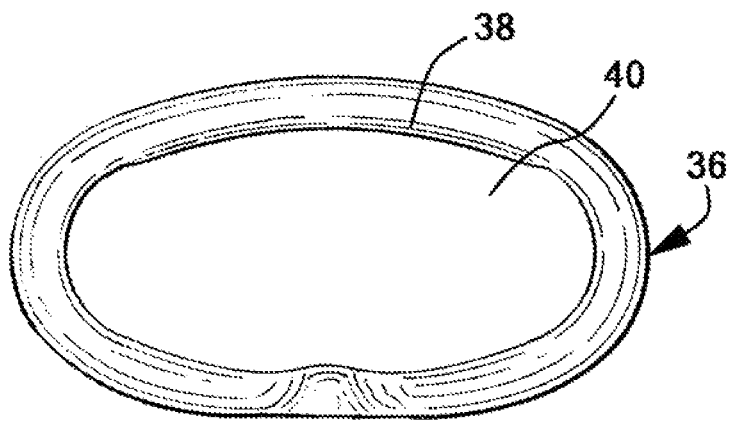
FIG. 18 is bottom plan view of the housing body segment of the nasal ventilation mask of FIG. 3.

The housing body segment 50 can also have the generally oval footprint or configuration generally at the distal end 36 or approximately oval as shown for example in FIGS. 17-18. Thus, the distal end opening 40 may have an oval configuration to be placed on the face of a patient. As discussed in greater detail below, other exemplary embodiments may have more of an obround configuration at the distal end 36.

As discussed, the housing body segment 50 is made from a flexible elastomeric material having a low or soft durometer value. In certain exemplary embodiments, the material can be thermoplastic polyurethane (TPU), thermoplastic elastomer or low durometer silicone. In further examples, such materials can have a Shore A durometer in the range of 20-50. In still a further exemplary embodiment, the Shore A durometer can be in the range of 30-40. In an exemplary embodiment, the housing body segment 112 has a part material volume of 1.042 cubic inches.

FIGS. 22-28 further disclose the connector segment 52. As discussed, the connector segment 52 cooperates with and is operably connected to the housing body segment 50 to form the nasal mask 10 as described in greater detail below. The connector segment 52 generally forms an upper portion of the nasal mask 10. The connector segment 52 has a base portion 80 that generally corresponds to the top wall 28 of nasal mask 10. The connector segment 52 further has an upper sidewall segment 82 that generally depends down from the base portion 80. The base portion 80, or top wall 28, in cooperation with the upper sidewall segment 82 defines an internal area that cooperates with the internal area defined by the housing body segment 50 to define the internal cavity 30. It is further understood that the base portion 80, or top wall 28 is generally recessed from an upper most portion of the upper sidewall segment 86. This configuration assists in providing a tactile feedback for emergency responders when pressing on the mask 10. As discussed below, the emergency responder, with fingers or a thumb and finger, may press down on the top wall 28 to assist in generating a airtight seal and the recessed configuration helps better achieve this action.

Figure 27:
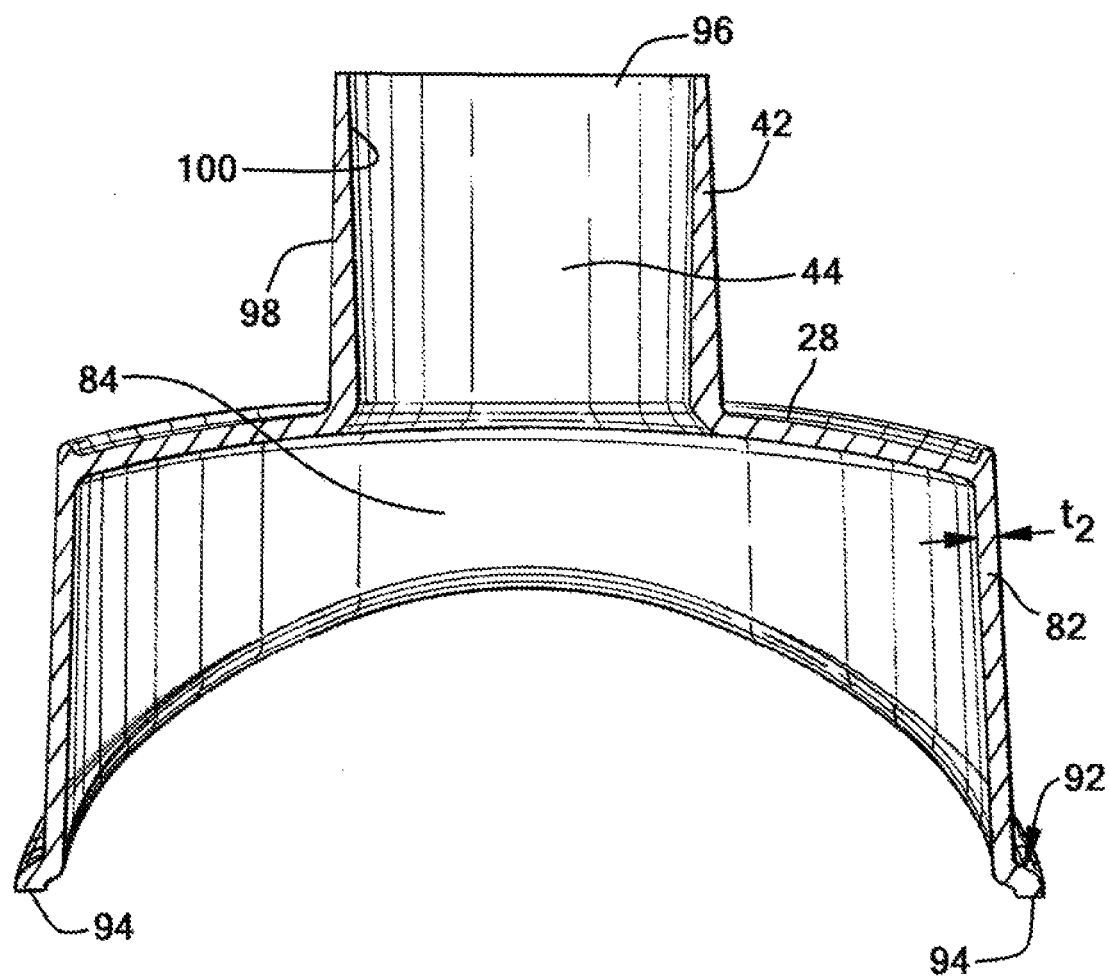
FIG. 27 is a cross-sectional view taken along lines 27-27 of FIG. 26.

Similar to the lower sidewall segment 56 of the housing body segment 50, the upper sidewall segment 82 defines a front wall section 84, a rear wall section 86, a first end wall section 88 and a second end wall section 90. As further shown, the front wall section 84 has a shorter dimension than the rear wall section 86. The front wall section 84 has a concave lower perimeter. The upper sidewall segment 82 has a proximal end that is integrally connected to the base portion 80 and top wall 28. These connections further define the first shoulder 32 and the second shoulder 34 at respective interface areas between the top wall 28 and the upper sidewall segment 82. It is understood that such connections are integral in an exemplary embodiment of the invention. As shown in FIG. 27, an angled transition connector 92 is formed generally at a distal end of the upper sidewall segment 82. The transition connector 92 extends outwardly from the upper sidewall segment 82. Thus, the upper sidewall segment 82 is positioned inward of the transition connector 92 or the upper sidewall segment 82 is inwardly offset from the transition connector 92. Thus, transition connector 92 extends circumferentially inward from the housing body segment 50 wherein the upper sidewall segment 82 is offset circumferentially inward from the lower sidewall segment 56 of the housing body segment 50. In one exemplary embodiment, the angled transition connector 92 is integral with upper sidewall segment 82. A free end of the angled transition connector 92 defines a second connection surface 94 that faces downward way from the top wall 28. It is understood that the second connection surface 94 could take various configurations such as a combination of planar and angled surfaces, but generally has a cooperative configuration to be operably connected to the first connection surface 66. The second connection surface 94 is closer in proximity to the top wall 28 at the front wall section 84 than the second connection surface 94 at the rear wall surface 86. In addition, the second connection surface 94 slopes downwardly from the front wall section 84 towards the rear wall section 86. The second connection surface 94 may be considered to slope along generally a conic curve in one exemplary embodiment. Other sloped curves are also possible with the connector segment 52 as well as the housing body segment 50. As can be appreciated from FIG. 28, at proximate a lateral midpoint of the connector segment 52 between the front wall section 84 and the rear wall section 86, the second connection surface 94 has a generally horizontal configuration HS towards the rear wall section 86. The connection surface 94 has a downwardly sloped segment SS and a generally horizontal segment HS (or a segment that is considered generally tangential to a horizontal plane). As further shown in FIG. 27, the upper sidewall segment 82 has a second thickness $t_2$, wherein the second thickness $t_2$ is 0.045 inches in one exemplary embodiment. It is understood that the thickness can be varied. In addition, the top wall 28 has a thickness of 0.050 inches. It is further understood that the free end of the angled transition connector 92 that defines the second connector surface 94 has a thickness of 0.070 inches, which generally corresponds to the thickness $t_1$ of the lower sidewall segment 56.

Figure 28A:
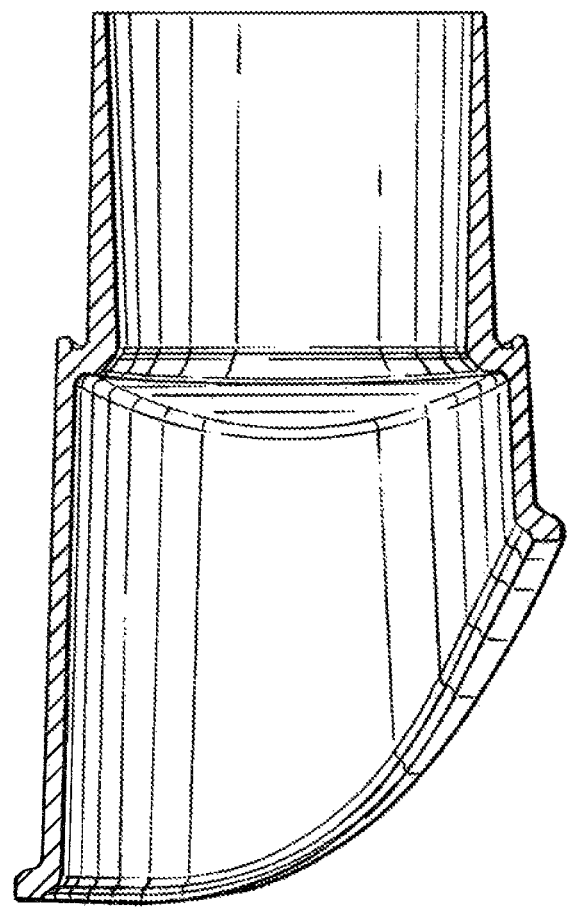
FIG. 28A is another cross-sectional view taken along lines 28-28 of FIG. 26.
Figure 28:
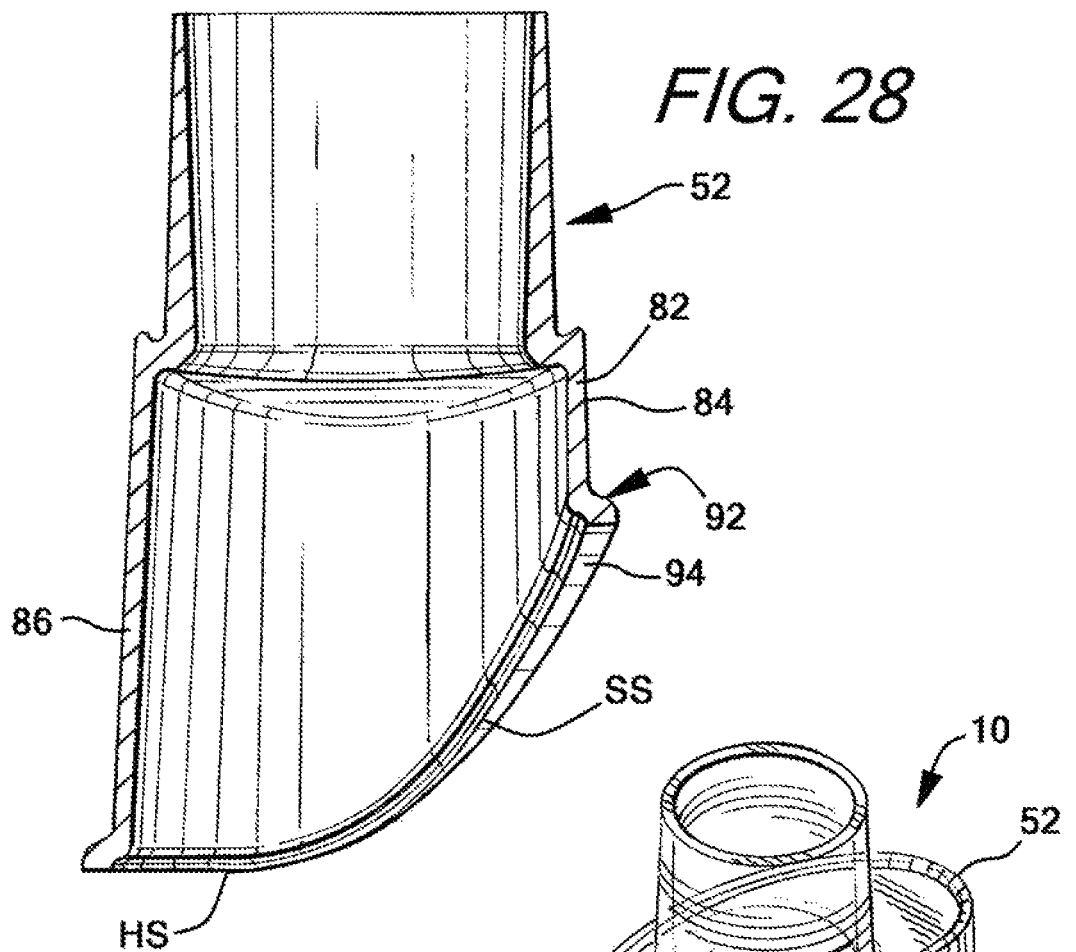
FIG. 28 is a cross-sectional view taken along lines 28-28 of FIG. 26.
Figure 29:
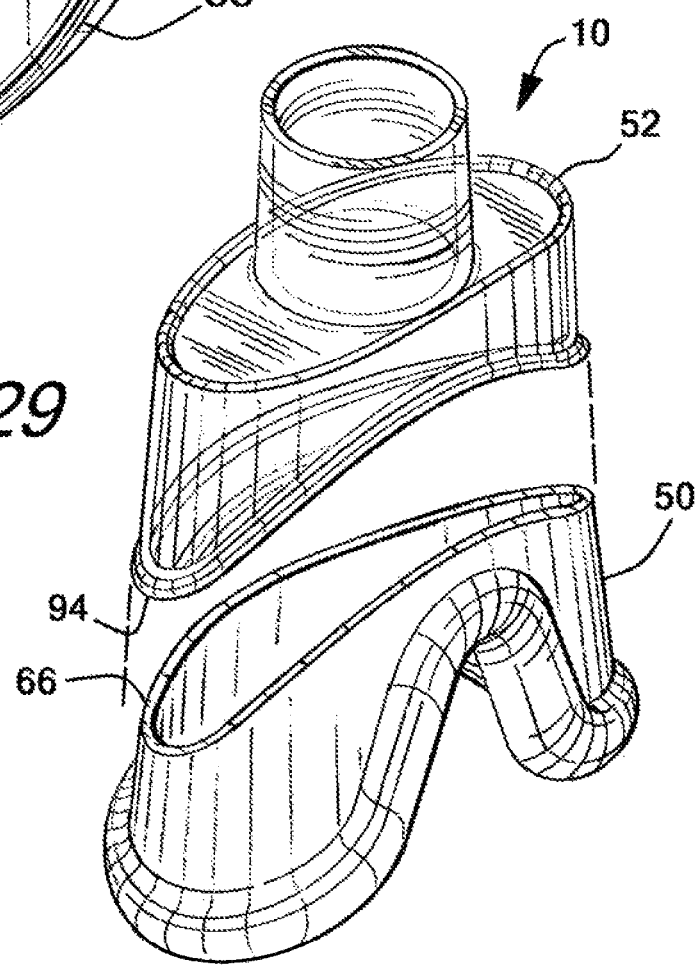
FIG. 29 is an exploded perspective view of the nasal ventilation mask of FIG. 3 and showing the housing body segment and the connector segment.

As described and shown in FIG. 27, the connector segment 52 supports the receiver member 42, which extends from the top wall 28. The receiver member 42 defines an inlet opening 96 that is in fluid communication with the internal conduit 44, which is also in fluid communication with the internal cavity 30. The receiver member 42 has a tapered outer surface 98, and has a tapered inner surface 100. Thus, the receiver member 42 defines a conical tube. The wall thickness of the receiver member 42 can be in the range of 0.030 inches to 0.045 inches. In certain medical standards for respiratory equipment/conical connectors, a 1.432-degree internal diameter taper is specified. An external approximate 1.5-degree taper (draft angle) on the receiver member 42 is utilized for reliable ejection of the part during the molding process. In one exemplary embodiment, a distal end forming the outlet opening of the receiver member 42 is formed at approximately 0.030 inches in wall thickness. The wall thickness of the receiver member 42 more proximate the top wall 28 may be 0.074 inches. Thus, the receiver member 42 has a greater wall thickness proximate the top wall 28 and a lesser thickness towards the inlet opening 96. As discussed, the receiver member 42 is dimensioned to operably connect to the inflatable bag of the manual resuscitator assembly. This configuration is dimensioned to conform to International Standard Specifications for conical socket connectors for respiratory equipment. For example, FIG. 28A shows metric dimensions to conform to the International Standard specifications for a 22-millimeter conical socket connector for respiratory equipment.

The connector segment 52 is made from a more rigid material. In exemplary embodiments, the connector segment 52 can be made from acrylonitrile butadiene styrene (ABS) or polycarbonate. As will be discussed in greater detail below, these materials are more rigid than the materials forming the housing body segment 50. Other rigid materials are also possible for the connector segment 52. In a further exemplary embodiment, the connector segment 52 has a part material volume of 0.458 cubic inches.

Figure 30:
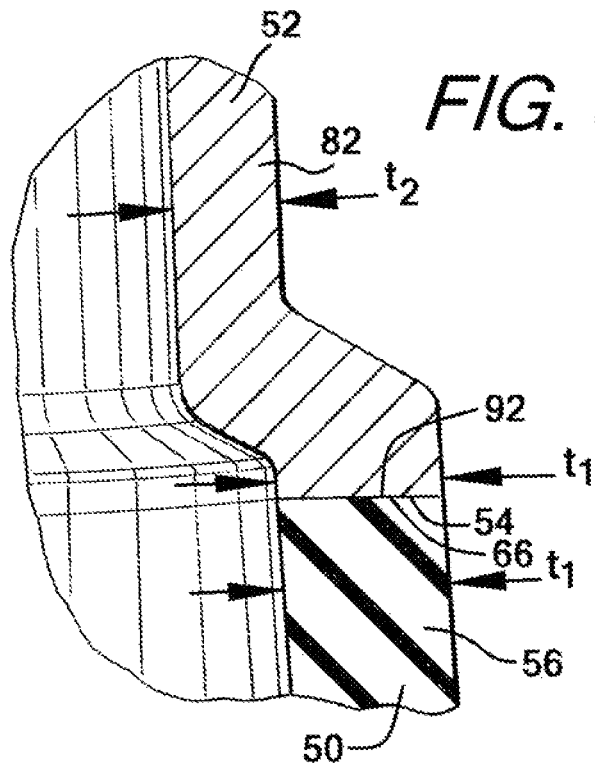
FIG. 30 is an enlarged partial view of the nasal ventilation mask showing a connection joint between the housing body segment and the connector segment.

As can be appreciated from FIGS. 3-7 and 30, the housing body segment 50 is operably connected to the connector segment 52 to form the nasal ventilation mask 10. When operably connected, the first connection surface 66 and the second connection surface 92 abut and are joined together to form the connection joint 54. The upwardly facing first connection surface 66 of the housing body segment 50 confronts the downward facing second connection surface 92 of the connector segment 52. In an exemplary embodiment, the connection joint 54 is formed via an over-molding injection process wherein the segments 50,52 are joined together. For example, those skilled in the art understand that the connector segment 52 can be injection molded in a first mold assembly initially and after completion, placed into another mold assembly. The housing body segment 50 can then be injected molded, or over-molded onto the connector segment 52 resulting in the configuration described above and wherein a chemical bond is formed at the connection joint 54 (FIG. 30). In addition, more complex mold assemblies can be used wherein the housing body segment 50 is molded sequentially during the same overall process as the molding of the connector body segment 52. Other connection methods are also possible such as adhesive bonding or other chemical bonding. Interlocking mechanical connections can also be utilized. Combinations of the above-described connection methods can also be utilized. It is further understood that in a two-shot molding process or over-molding process in forming the housing body segment 50 and connector segment 52, the chemical bond is formed between the segments 50,52. The chemical bond is formed between the materials of the two segments 50,52 to form the connection joint 54.

Figure 4:
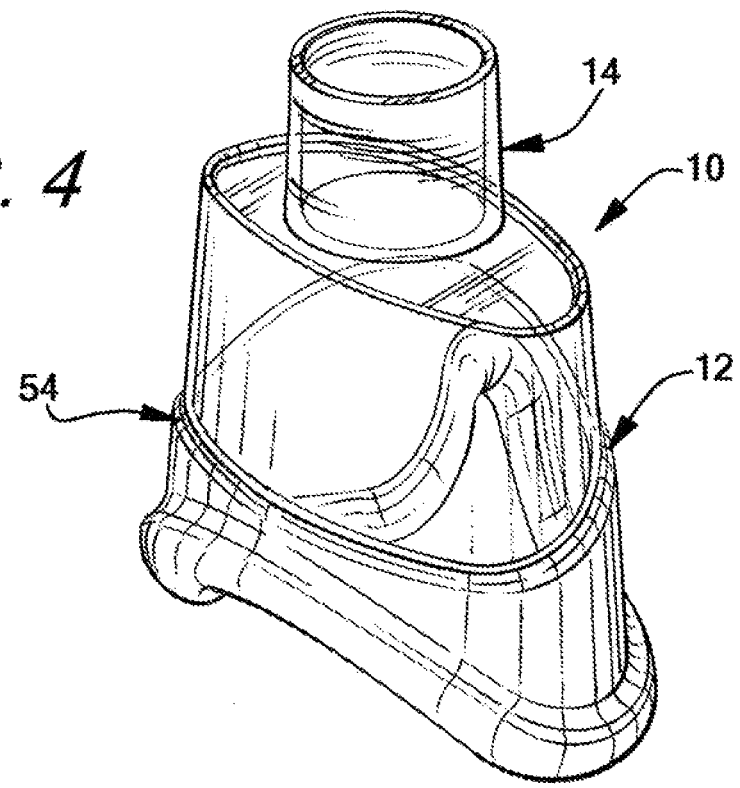
FIG. 4 is a rear perspective view of the nasal ventilation mask of FIG. 3.
Figure 5:
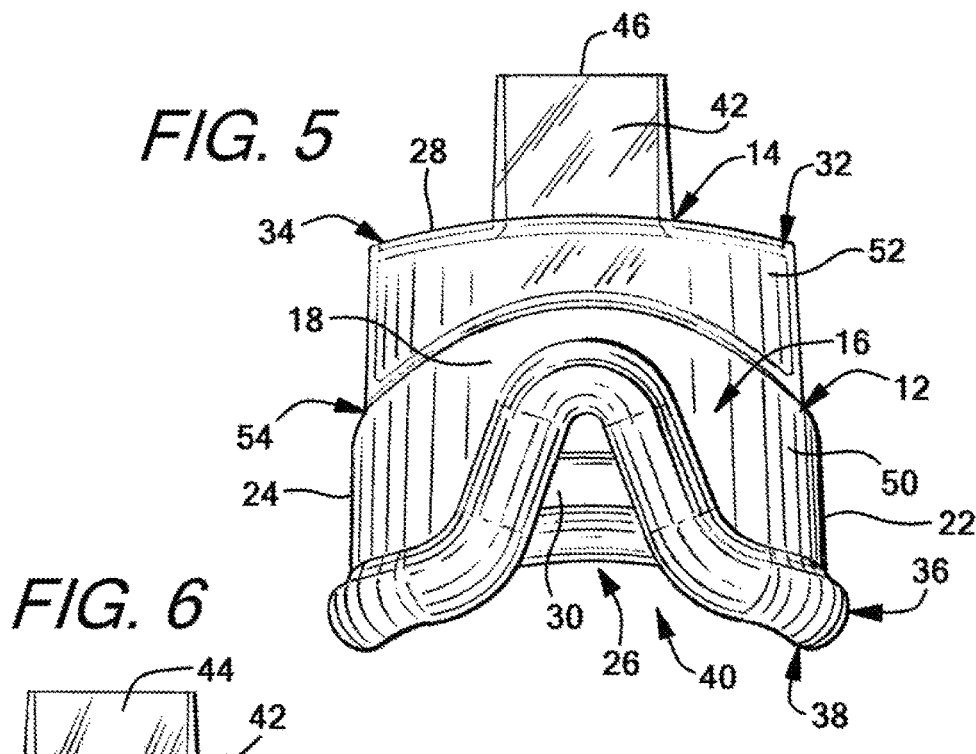
FIG. 5 is a front elevation view of the nasal ventilation mask of FIG. 3.
Figure 6:
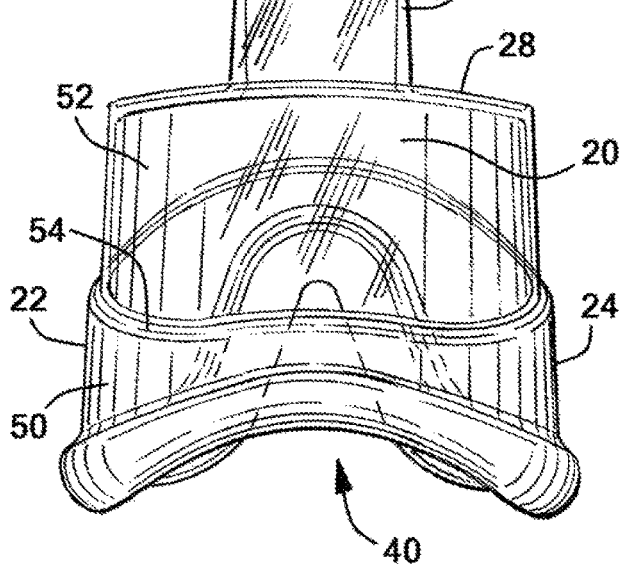
FIG. 6 is a rear elevation view of the nasal ventilation mask of FIG. 3.
Figure 7:
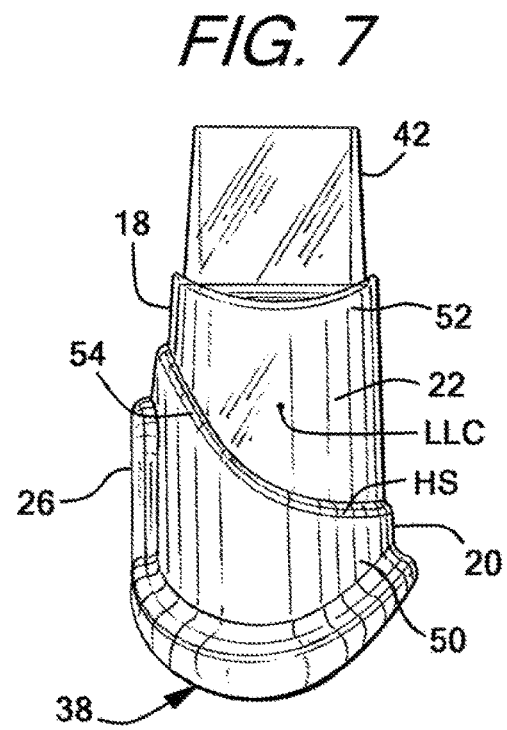
FIG. 7 is a side elevation view of the nasal ventilation mask of FIG. 3, the opposite side elevation view being the same.
Figure 8:
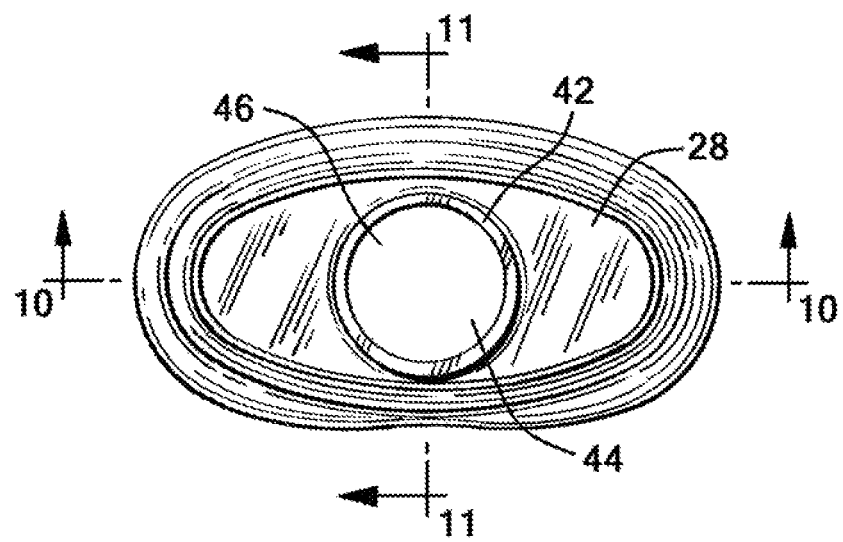
FIG. 8 is a top plan view of the nasal ventilation mask of FIG. 3.
Figure 9:
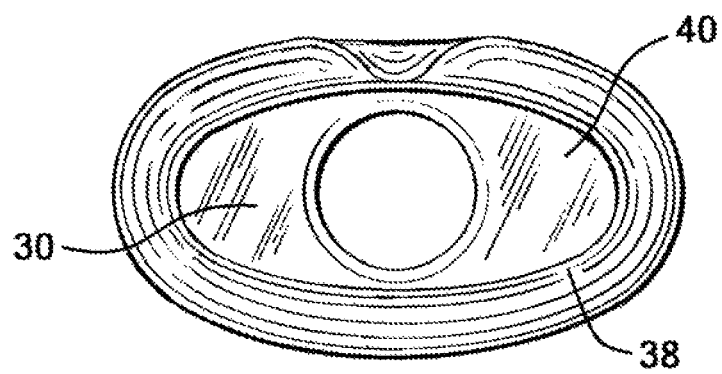
FIG. 9 is a bottom plan view of the nasal ventilation mask of FIG. 3.
Figure 10:
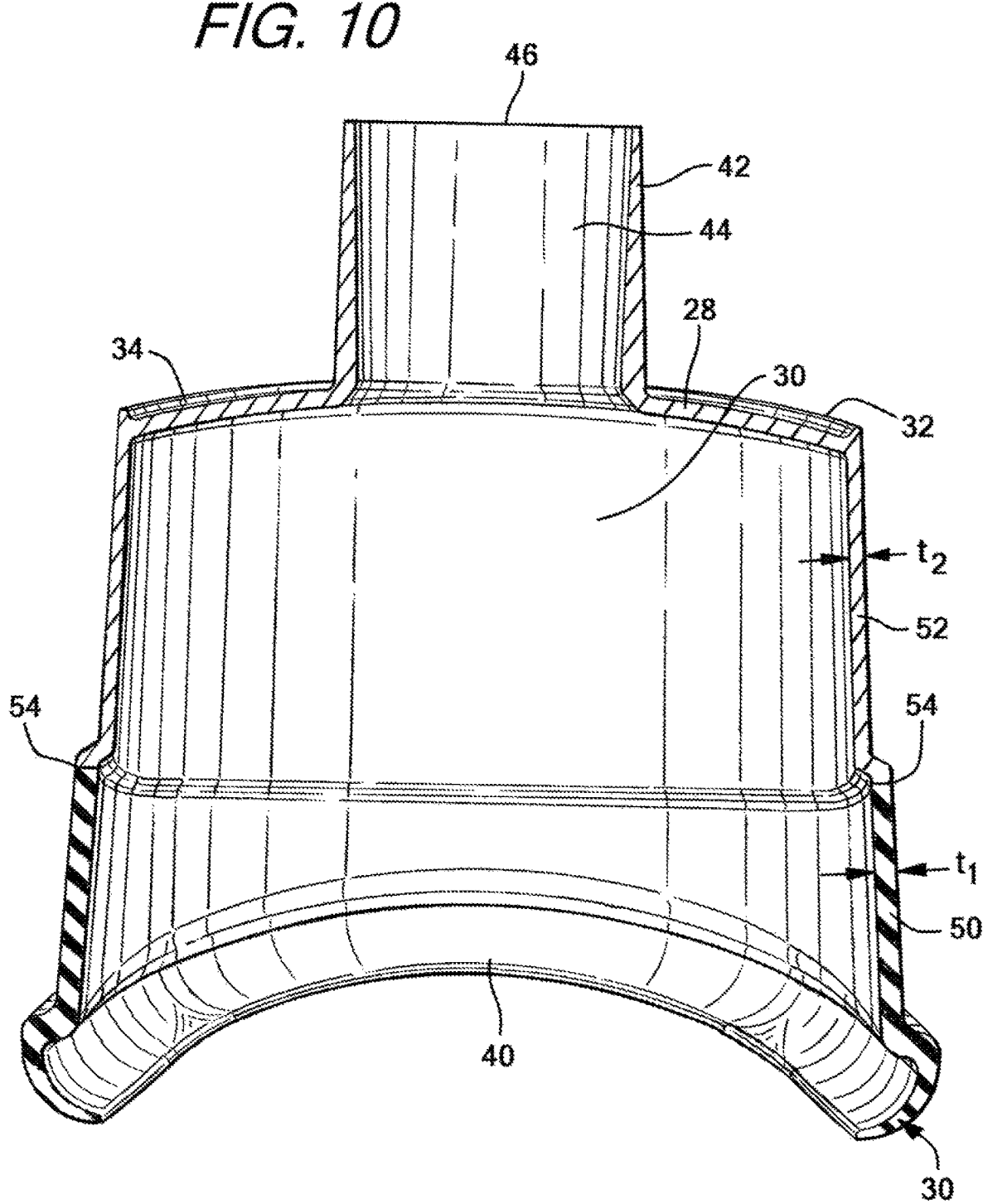
FIG. 10 is a cross-sectional view taken along lines 10-10 of FIG. 8.
Figure 11:
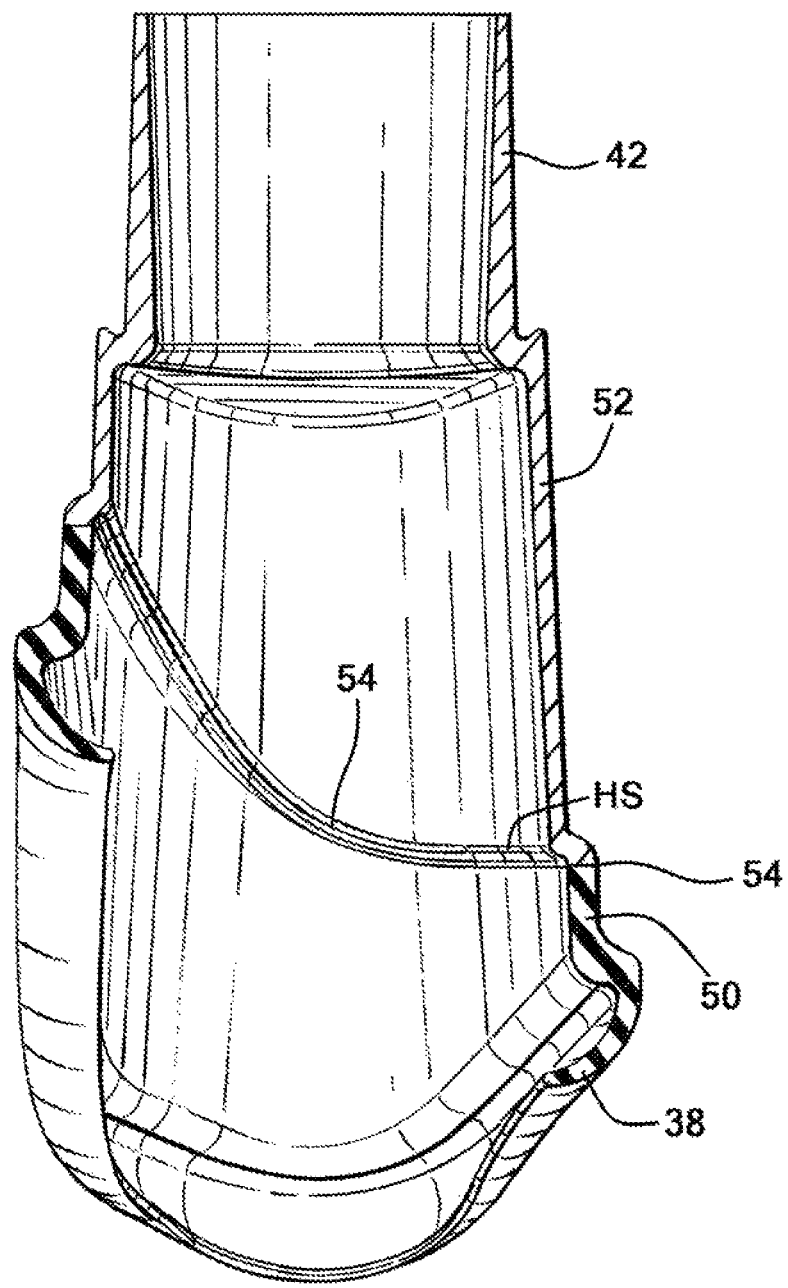
FIG. 11 is a cross-sectional view taken along lines 11-11 of FIG. 8.
Figure 12:
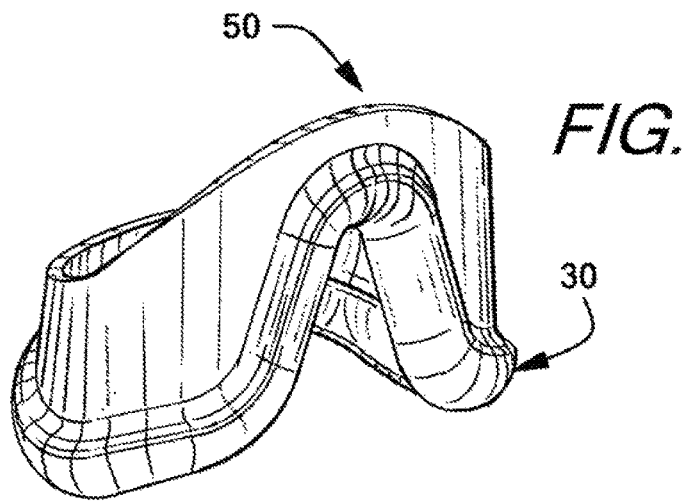
FIG. 12 is a front perspective view of a housing body segment of the nasal ventilation mask of FIG. 3.
Figure 13:
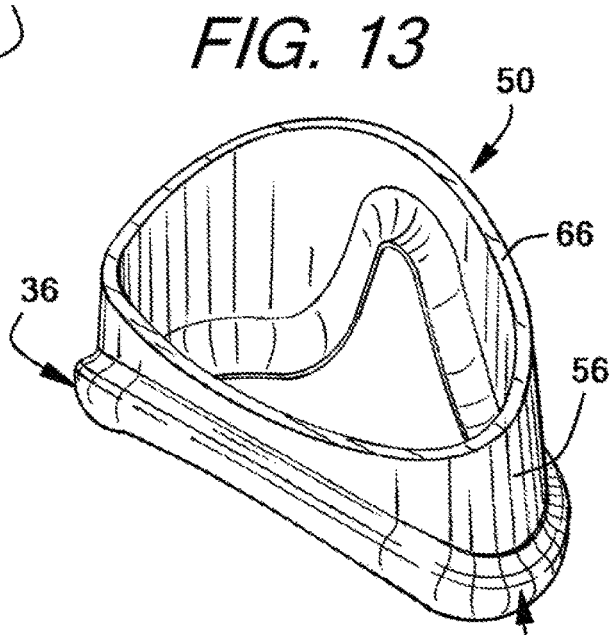
FIG. 13 is a rear perspective view of a housing body segment of the nasal ventilation mask of FIG. 3.
Figure 14:
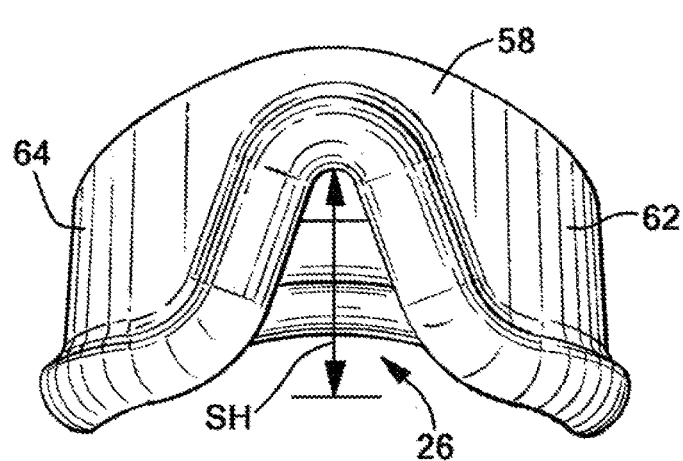
FIG. 14 is a front elevation view of the housing body segment of the nasal ventilation mask of FIG. 3.
Figure 15:
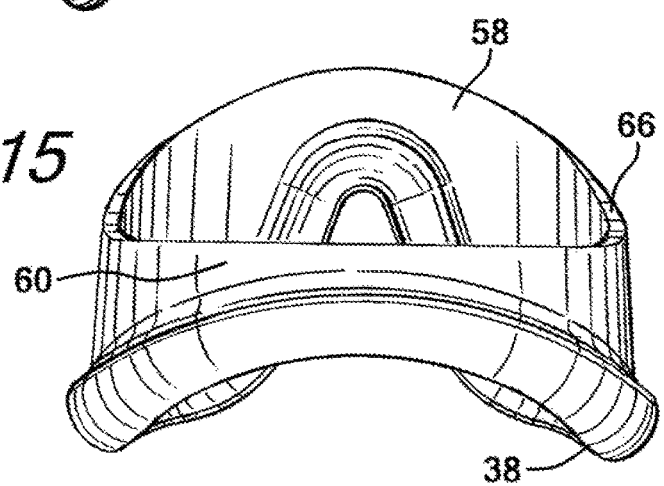
FIG. 15 is a rear elevation view of the housing body segment of the nasal ventilation mask of FIG. 3.

FIGS. 3, 4 and 30 further show the connection joint 54 formed between the housing body segment 50 and the connector segment 52. The connection joint 54 generally has a contoured path around the circumferential sidewall 16. It is understood that the connection joint 54 travels around the full periphery or circumference of the mask 10. The contoured path provides enhanced operability of the mask 10. The connection joint 54 is more proximate to the top wall 28 at the front wall section 18 of the mask 10 than at the rear wall section 20 of the mask 10. As shown in FIG. 5, the connection joint 54 has a generally concave configuration. As shown in FIG. 6, the connection joint 54 has a generally horizontal configuration across the rear wall section 20. As previously discussed, the connection joint 54 has a profile in a curved-slanted configuration, or downwardly sloped along a curved path, generally at the end wall sections 22,24 of the mask 10. In particular and as shown in FIGS. 7 and 11, the connection joint 54 generally slopes downwardly in a curved configuration at the first end wall section 22 and the second end wall section 24 from the front wall section 18 towards the rear wall section 20. The connection joint 54 thus has a curved segment SS and a substantially horizontal segment HS more proximate the rear wall section 20 of the mask 10. The contoured or curved segment of the connection joint 54 can also take other curved forms. In one exemplary embodiment, the connection joint 54 may slope downwardly along generally a conic curve. The connection joint 54 may also be contoured along generally a radial curve or have a configuration of an arc of a circle.

With the curved/slanted configuration of the connection joint 54, it is understood that the housing body segment 50 and the connector segment 52 also possess such curved/slanted configurations as described above. With such configuration, at proximate a lateral/longitudinal central portion LLC at the first end wall section 22 and the second end wall section 24 of the mask 10, the mask 10 is formed of the more rigid material of the connector segment 52. This can be appreciated from FIG. 7. With the curved profile, the more flexible housing body segment 50 is positioned below the lateral/longitudinal central location LLC while the connector segment 52 having more rigid material occupies the lateral/longitudinal central location LLC. With the sloped or contoured connection joint 54 along a downwardly sloped curve (sloping downwardly along a curved path) at the first end wall section 22 and the second end wall section 24, the mask 10 is formed of the more rigid material of the connector segment 52 at a larger area of the end wall sections 22,24 of the mask 110. This configuration assists in further stabilizing the mask 10 and resists undue flaring or bulging when pressing the mask 10 against a patient's skin during use to be described further. Such flaring has an adverse impact in creating an airtight seal against a patient's face. Thus, the configuration provides for more controlled flexibility of the mask 10 at the end wall sections 22,24 to accommodate varying patient facial contours while still providing for an enhanced seal against the face of the patient. Such configuration further provides material cost-saving benefits. In an exemplary embodiment, the curved slanted profile of the connection joint 54 is the result of a conic profile that travels linearly from one side of the mask body to the other side of the mask body in a path generally normal to a central plane of symmetry of the mask body. As discussed, it is understood that the housing body segment 50 and the connector segment 52 have the corresponding and confronting curved slanted profiles.

Figure 31:
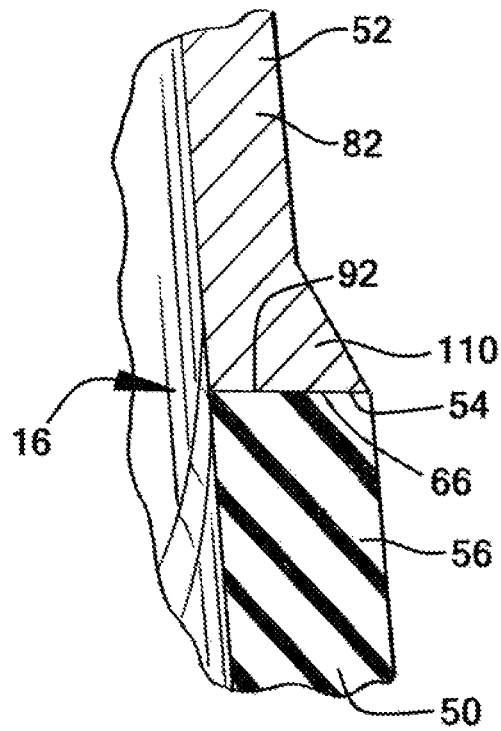
FIG. 31 is an enlarged partial view of the nasal ventilation mask showing an alternative connection joint between the housing body segment and the connector segment.

FIG. 31 further discloses another configuration of the connection joint 54 of the mask 10. The housing body segment 50 has the first connection surface 66 and the connector segment 52 has the second connection surface 94 wherein the respective connection surfaces 66,94 confront one another. In an over-molding process in one exemplary embodiment of the invention, the respective materials of the housing body segment 50 and the connector segment 52 are chemically-bonded in a butt joint to form the connection joint 54. As further shown in FIG. 31, the connector segment 52 has a flared portion 110 that gradually increases the thickness of the sidewall 82 of the connector segment 52 to correspond to the thickness of the sidewall 56 of the housing body segment 50. In an exemplary embodiment, the flared portion 110 forms a transitional wall thickness from 0.045 inches to 0.075 inches. The thickness of the sidewall 56 of the housing body segment 50 is 0.075 inches. It is further understood that the wall thicknesses could be in the range of 0.070 inches to 0.080 inches in other exemplary embodiments. The flared portion 110 is dimensioned to have an outwardly flared portion to correspond to the thickness of the lower sidewall segment 56.

Figure 32:
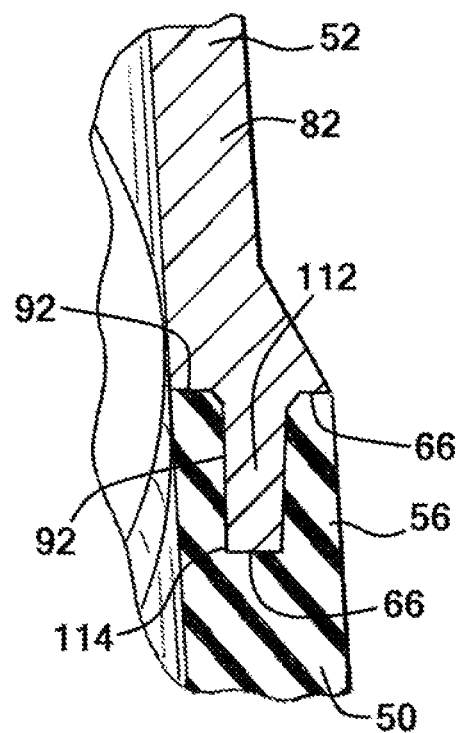
FIG. 32 is an enlarged partial view of the nasal ventilation mask showing an alternative connection joint between the housing body segment and the connector segment.

FIG. 32 discloses another alternative connection joint 54. The connector segment 52 has a tongue 112 and the housing body segment 50 has a groove 114. The tongue 112 is received in the groove 114. In the over-molding process as described, the segments 50,52 are chemically-bonded to form the connection joint 55. In this tongue/groove configuration, the connection joint 54 has increased bonding surface areas. The tongue/groove configuration provides additional mechanical integrity. It is further understood that one of the housing body segment 50 and the connector segment 52 can have the tongue 112 and the other of the housing body segment 50 and the connector segment 52 can have the groove 114. While a chemical bond is formed in any of the connection joints 54 in an exemplary embodiment, it is understood that other bonding structures can be utilized including adhesive bonding or other fused structures. It is understood that any of the various structures of the connection joint 54 can be used in the various exemplary embodiments of the nasal ventilation mask 10 described herein.

Figure 33:
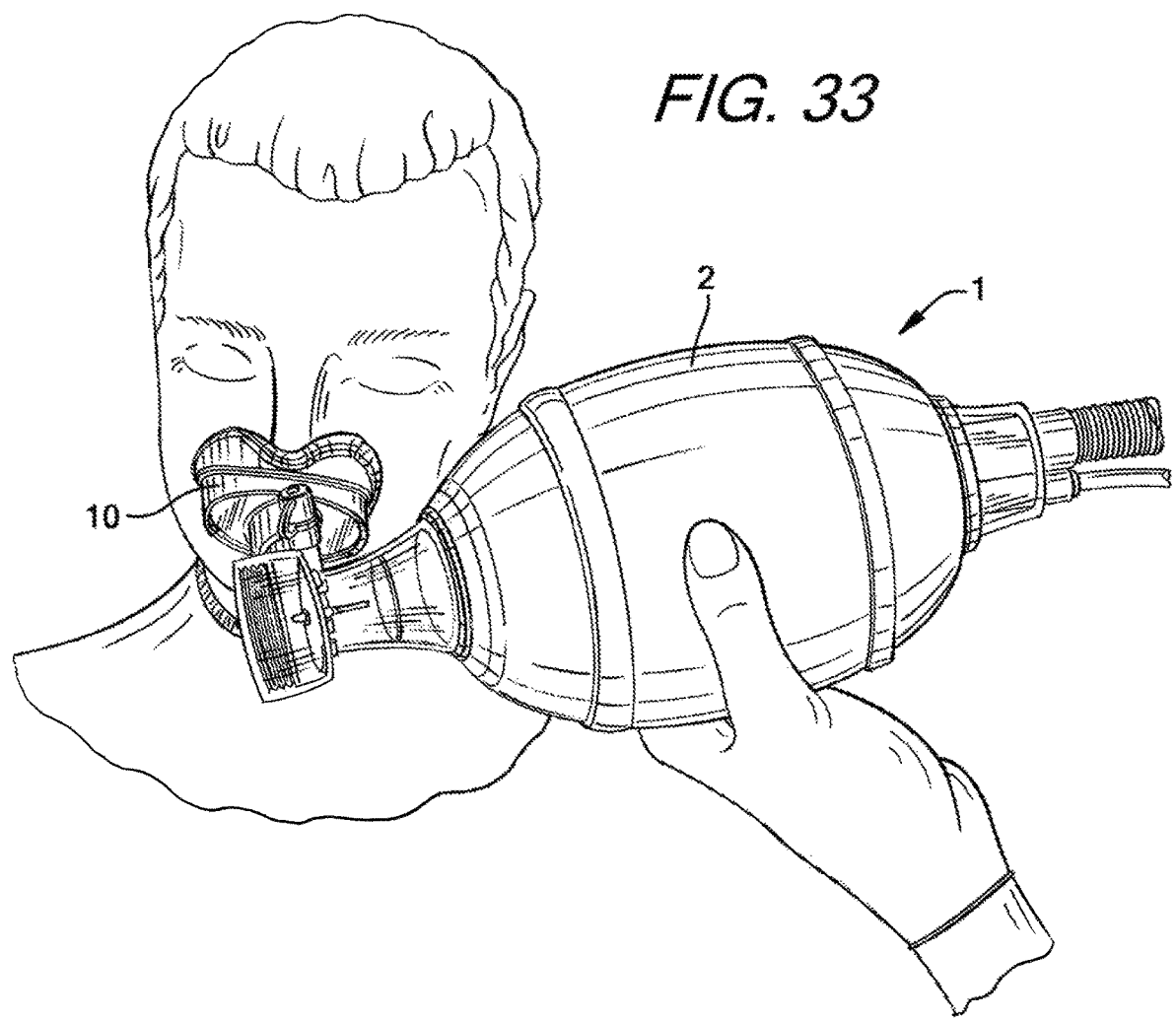
FIG. 33 is a perspective view of the nasal ventilation mask operably connected to the manual resuscitator bag assembly and in use on a patient.
Figure 34:
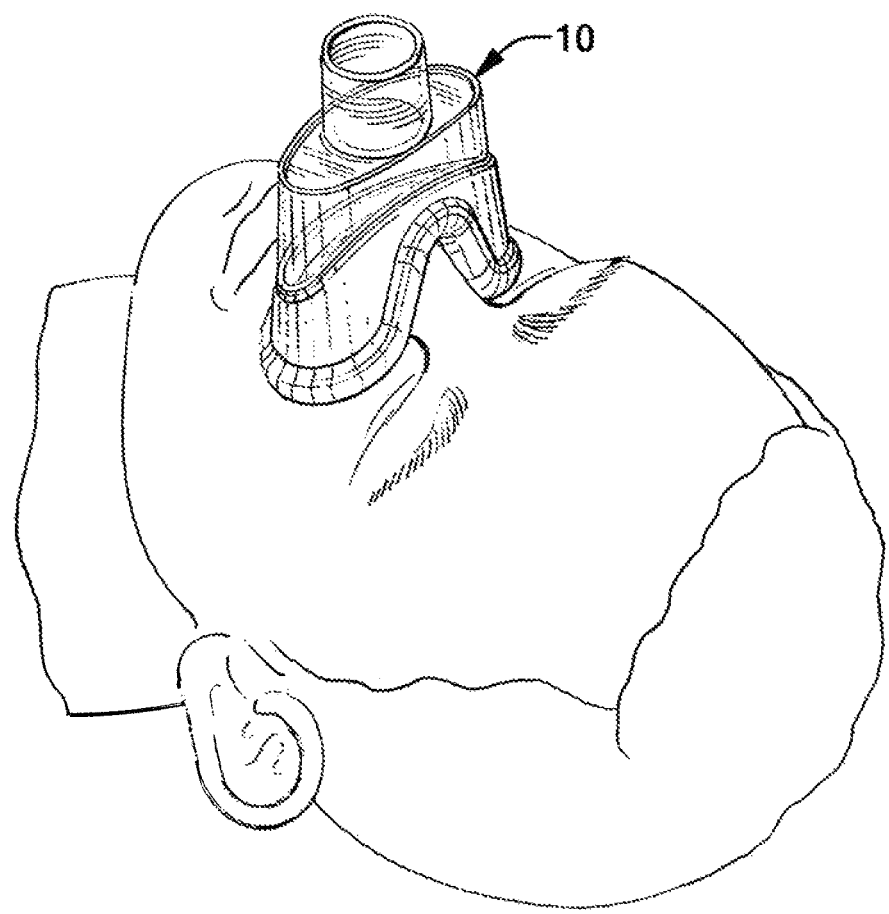
FIG. 34 is a schematic perspective view of the nasal ventilation mask positioned on the face of a patient.

With the nasal ventilation mask 10 fully formed, the mask 10 can be incorporated with an inflatable bag of a manual resuscitator bag assembly. The mask 10 is operably connected to the bag assembly where emergency responders or resuscitators can use the bag assembly on a patient to supply breathing gas to the patient. It is understood that associated fittings may be incorporated into the operable connection between the inflatable bag 2 and the nasal ventilation mask 10. FIG. 33 shows the nasal mask 10 connected to an inflatable bag 2 of a manual resuscitator bag assembly 1. It is understood that the bag assembly 1 has associated fittings to operably connect to the receiver member 42 in accordance with International Standard specifications for connectors for respiratory equipment as discussed herein (FIG. 28A). Upon such connection, the inflatable bag 2 along with any additional breathing gas supply is in fluid communication with the nasal ventilation mask 10 through the inlet opening 46, internal conduit 44 and internal cavity 30.

Figure 37A:
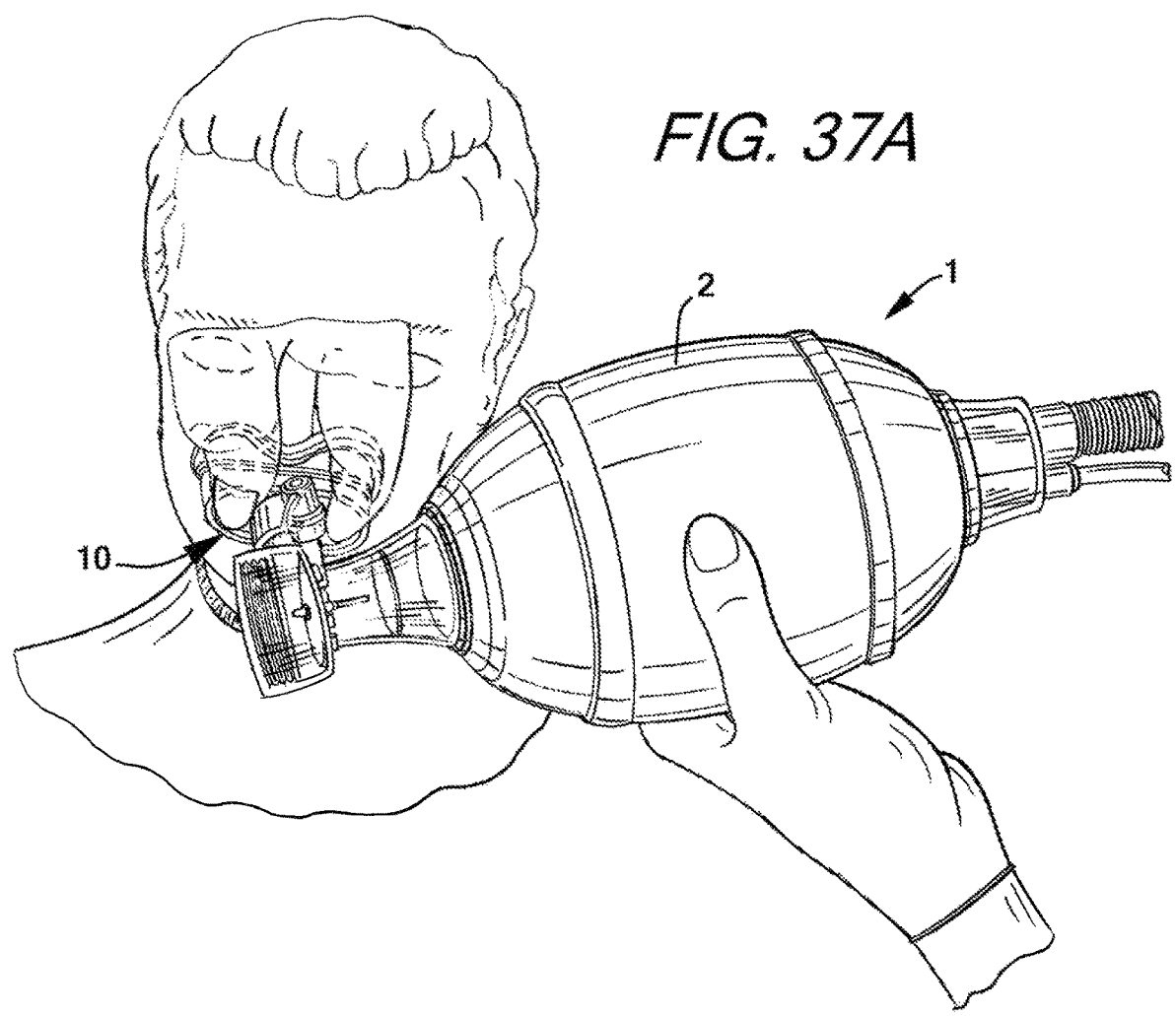
FIG. 37A is a perspective view of the nasal ventilation mask operably connected to the manual resuscitator bag assembly and in use on a patient.
Figure 37B:
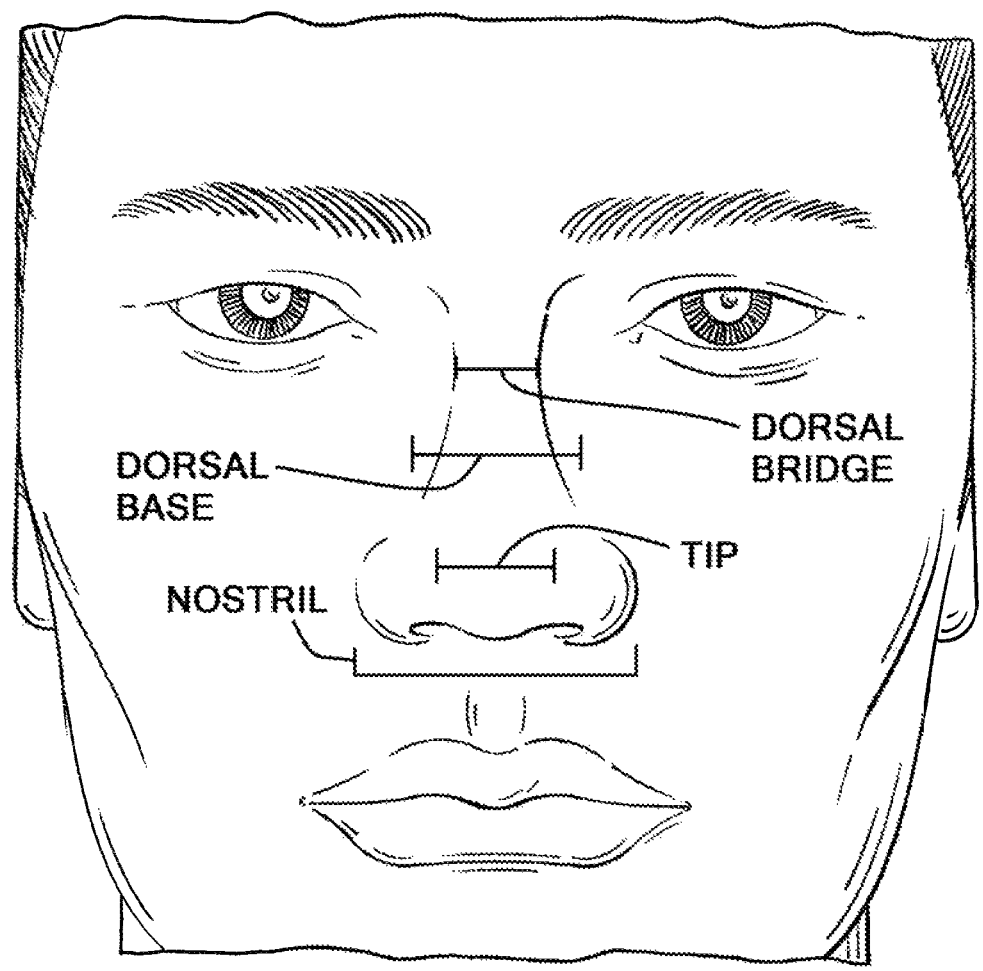
FIG. 37B is a schematic plan view of a face of a patient designating portions of a nose of the patient.
Figure 38:
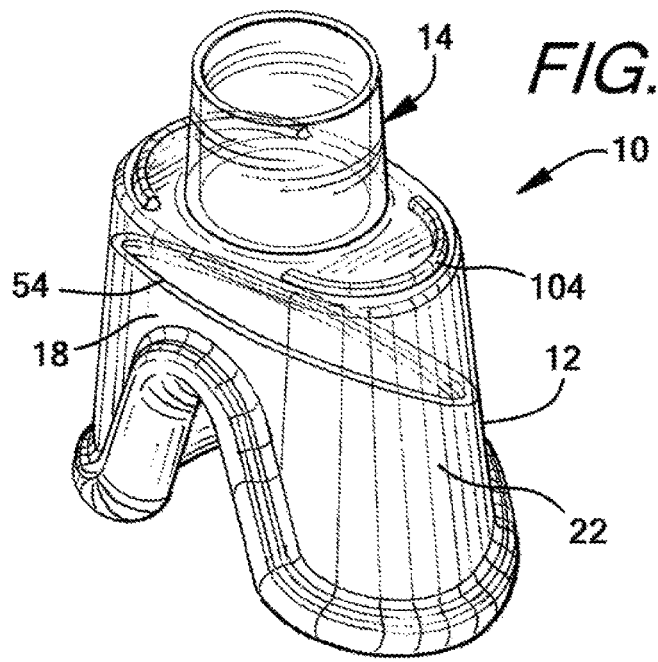
FIG. 38 is a front perspective view a nasal ventilation mask according to another exemplary embodiment of the present invention.
Figure 39:
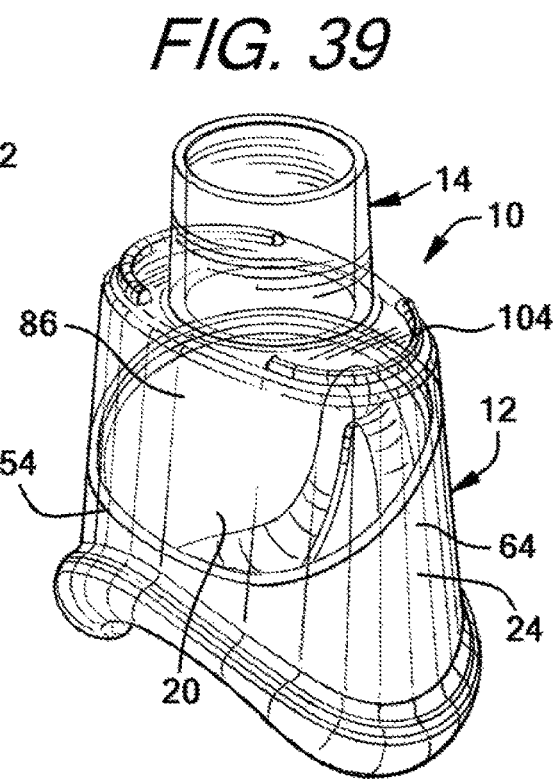
FIG. 39 is a rear perspective view of the nasal ventilation mask of FIG. 38.

A patient may experience an event requiring breathing assistance. In operation, the nasal ventilation mask 10 (understood already operably connected to the inflatable bag 2 of the bag assembly 1 or oxygen source) is placed over a nose of the patient, e.g., over a nasal airway of the patient. Thus, the nose of the patient is received through the distal end opening 40. The slot 26 also receives a portion of the nose wherein the mask 10 at the slot 26 engages the patient generally at the dorsal base of the nose of the patient. As can be appreciated from FIG. 37B, the generally oval footprint of the mask 10 is dimensioned such that the mask 10 at the top of the slot 26 engages the nose at the dorsal base and not at the dorsal bridge of the nose. Engaging at the dorsal base of the nose allows for creating a more consistent airtight seal against the patient's face. It is understood that the mask 10 could be designed wherein the end opening 40 is structured to not need the slot 26. In an exemplary embodiment, however, the slot 26 forms part of the end opening 40 or is in fluid communication thereto. The sealing member 38 is engaged with and pressed against the face of the patient to create an airtight seal between the mask 10 and the patient's skin. As can be appreciated in FIGS. 33-37, the sealing member 38 at the distal end 36 of the housing body 12 engages under the nostrils of the nose and above the upper lip of the patient. Further portions of the sealing member 38 engage at respective sides of the nose. Finally, portions of the sealing member 38 at the slot 26 engages up the nose, away from the tip of the nose and proximate the dorsal base of the nose. The mask 10 is designed and dimensioned with the substantially oval footprint and size (slot height SH) of slot 26 to engage at the dorsal base and not to extend all the way to the dorsal bridge of the nose. Thus, as the mask 10 has the oval configuration and slot 26, the mask 10 engages away from the dorsal bridge and not closer to the patient's eyes. As shown in FIG. 35, the outer surface 76 of the inwardly curled lip 70 of the second sealing segment 30 initially engages the skin of the face of the patient. It is understood that this engagement is fully around the entire end opening 40 including the slot 26. It is understood the lip member 70 may deflect a certain amount in response to the initial placement of the mask 10 on the face of the patient. FIG. 36, shows the mask 10 being further pressed against the face of the patient such as by an emergency responder. As shown in FIG. 37A, the emergency responder may use fingers or a finger and thumb to press against the shoulders 32,34 of the mask 10 to apply force F to create further sealing. The lip member 70 further deflects proximate the distal end 74 of the lip member 70 wherein the lip member 70 further deflects towards the internal cavity 30 wherein the outer surface 76 further engages the face of the patient. This deflected configuration of the lip member 70 achieves a tight enhanced pneumatic seal and airtight seal between the mask 10 and the patient's skin. The integrated reinforcing member 68 assists in providing stability to further enhance the airtight seal. It is understood that the airtight seal is achieved around the full end opening 40 including the slot 26. The seal achieved thus maintains air pressure in the internal cavity 30 of the mask.

As further can be appreciated from FIGS. 36-37A, the emergency responder can apply force F on the mask towards the patient's face to further enhance the seal. The emergency responder can use, for example, a thumb and finger, or other fingers, to press on the first shoulder 32 and the second shoulder 34. As the shoulders 32,34 provide a portion of a planar, platform-type surface that is rigid, the medical worker can easily apply any requisite force F to the mask 10 towards the patient's face to further enhance the seal (FIG. 37A). The profile of the mask 10 provides an easy engagement by the emergency responder. Because the nasal ventilation mask 10 only covers the nose, emergency responders or other medical workers have access to the patient's mouth to clean oral passageways such as if the patient vomits or if medical workers need to insert additional medical devices. After treatment on the patient is complete, the nasal mask 10 can be removed from the air bag by the emergency responder or other medical worker.

The nasal ventilation mask 10 can be used with a manual resuscitator bag assembly 1 as described but could also be used with other components. For example, the nasal ventilation mask can be used with a ventilator or a continuous positive airway pressure machine. Other components can also be operably associated or integrated with the mask such as oxygen monitors or carbon dioxide monitors or other sensors. Depending on desired configurations, the nasal mask 10 may incorporate additional port structures, adapters or other fittings for operable connection to such components. Such operable integrations with other components can be helpful to medical personnel. For example, integration of a carbon dioxide monitor assists in determining proper ventilation of the patient. Wireless technology can also be operably associated with the nasal mask 10 and such operable connections.

FIGS. 38-48 disclose a nasal ventilation mask according to another exemplary embodiment of the present invention, also designated with the reference numeral 10. The nasal mask 10 of FIGS. 38-48 has similar structures to the nasal mask 10 of FIGS. 3-37. The above descriptions regarding structures and functionality generally apply to this nasal mask 10, and similar structures are referenced with similar reference numerals. Structural features and functionality that are different from the previously-described embodiment will be further described herein and designated with additional reference numerals.

The nasal ventilation mask 10 of FIGS. 38-48 also utilizes the two-piece design having the housing body segment 50 and the connector segment 52. These segments 50,52 have a modified cooperative structure that forms the connection joint 54. In this embodiment, the connection joint 54 also has a contoured configuration around the sidewall 16 of the housing 12 rather than a linear, horizontal configuration to be described. As described in greater detail below, the connection joint 54 has a slanted configuration at the first end wall section 22 and the second end wall section 24.

Figure 40:
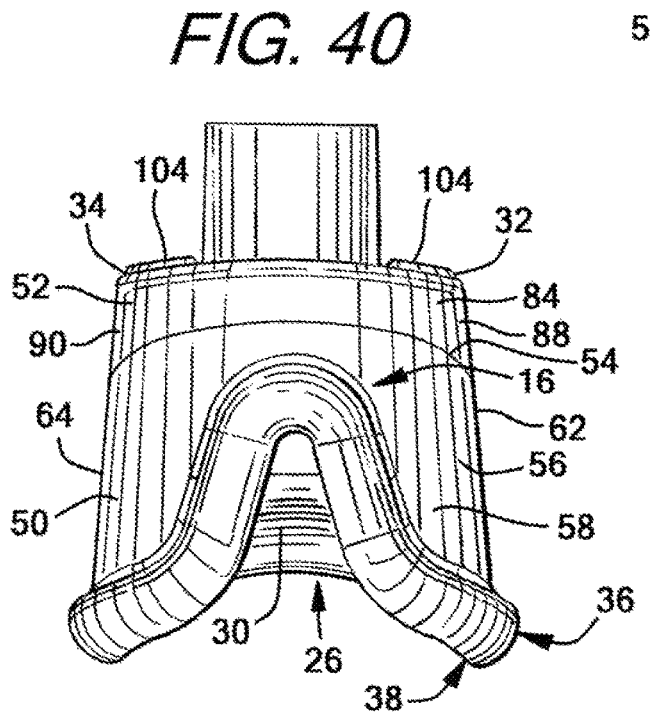
FIG. 40 is a front elevation view of the nasal ventilation mask of FIG. 38.
Figure 41:
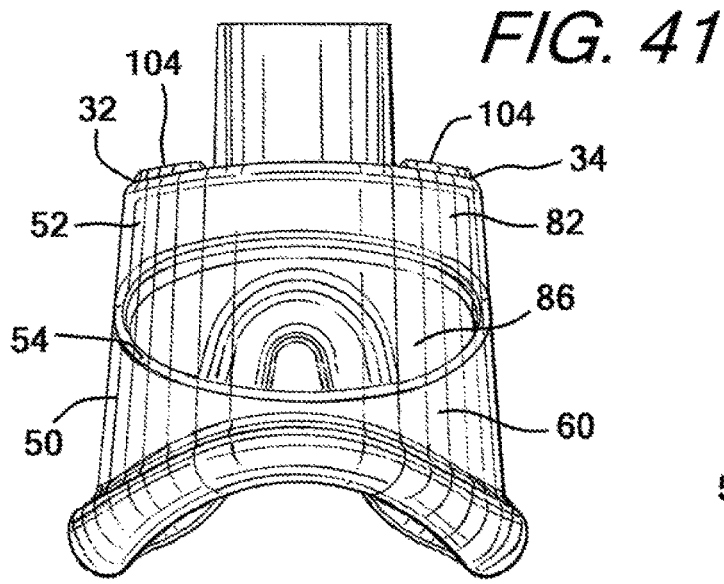
FIG. 41 is a rear elevation view of the nasal ventilation mask of FIG. 38.
Figure 42:
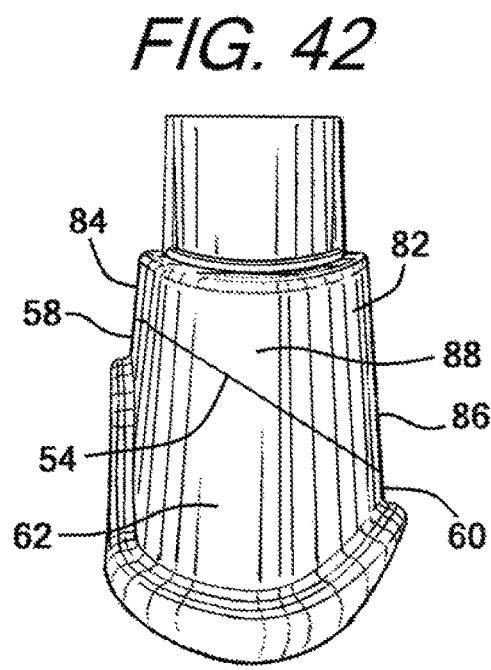
FIG. 42 is a side elevation view of the nasal ventilation mask of FIG. 38, the opposite side elevation view being the same.
Figure 48:
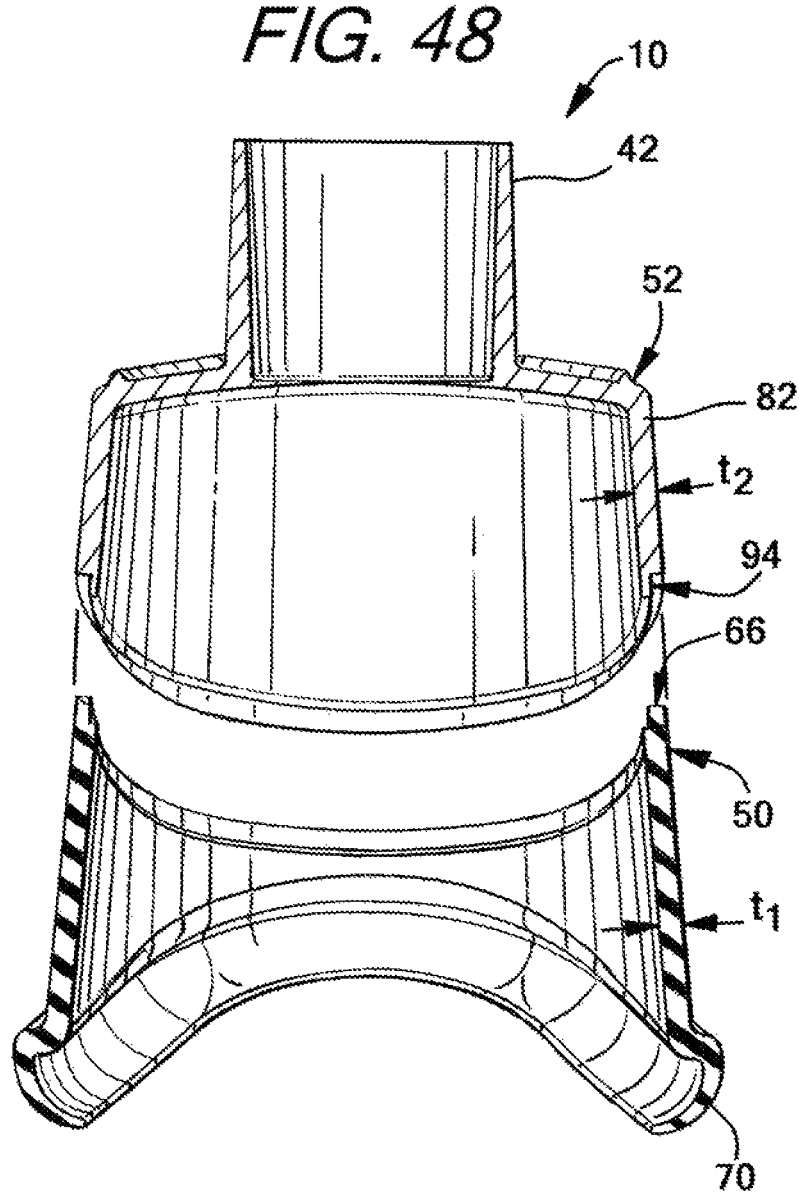
FIG. 48 is an exploded cross-sectional view of the nasal ventilation mask of FIG. 38; are side elevation views of the nasal ventilation masks of FIGS. 7 and 25.

FIGS. 38-48 further show the housing body segment 50. It is understood that the housing body segment 50 of FIGS. 38-48 is similar in structure to the housing body segment 50 of FIGS. 3-37. As shown in FIGS. 38-48, the housing body segment 50 generally forms a lower portion of the nasal ventilation mask 10, and thus defines, among other structures, the distal end 36 of the mask 10 as well as the sealing member 38. The housing body segment 50 has a lower sidewall segment 56 that forms the lower portion of the sidewall 16 of the housing 12. The lower sidewall segment 56 defines an internal area that will cooperate to form the internal cavity 30. The lower sidewall segment 56 also defines a front wall section 58, a rear wall section 60, a first end wall section 62 and a second end wall section 64. The front wall section 58 contains the slot 26 wherein the slot 26 is defined completely in the front wall section 58. As in the previous embodiment, the slot 26 is a portion of the end opening 40 and in communication with the end opening 40. As further shown, the front wall section 58 has a greater height/length dimension than the rear wall section 60. The front wall section 58 has a convex upper perimeter, but with a substantially horizontal central portion (FIG. 40). The lower sidewall segment 56 has a proximal end that defines a first connection surface 66 and facing upwards and away from the distal end 38 (FIG. 48). It is understood that the first connection surface 66 could take various configurations such as a combination of planar and angled surfaces. The first connection surface 66 has a greater height from the distal end 36 at the front wall section 58 than a height of the first connection surface 66 from the distal end 36 at the rear wall section 60. As can be appreciated from FIGS. 42 and 46, the first connection surface 66 slopes downwardly from the front wall section 58 towards the rear wall section 60. The first connection surface 66 slopes generally along a linear path from the front wall section 58 to the rear wall section 60 on both the first end wall section 62 and the second end wall section 64. At proximate a lateral midpoint of the housing body segment 50 between the front wall section 58 and the rear wall section 60, the first connection surface 66 generally passes therethrough. As further shown in FIG. 48, the first connection surface 66 defines a planar surface and an inclined surface facing into the internal area of the housing body segment 50. As further shown in FIG. 48, the lower sidewall segment 56 has a first thickness $t_1$ of 0.075 inches in one exemplary embodiment. It is understood that the thickness can be varied. For example, in another exemplary embodiment, the lower sidewall segment 56 could have a thickness of 0.125 inches.

Similar to the embodiment of FIGS. 3-37, the housing body segment 50 defines the distal end 36 and has the sealing member 38 proximate the distal end 36. As can be appreciated from FIGS. 45-48, the sealing member 38 takes the form of the lip member 70, and the housing body segment 50 further has the reinforcing member 68. It is understood that the above description regarding such structural features and functionality applies to the housing body segment 50 of FIGS. 38-48. It is also understood that the housing body segment 50 of FIGS. 38-48 is made from the same materials as discussed above.

FIGS. 38-48 further disclose the connector segment 52. As discussed, the connector segment 52 cooperates with and is operably connected to the housing body segment 50 to form the nasal mask 10 as described in greater detail below. The connector segment 52 generally forms an upper portion of the nasal mask 10. The connector segment 52 has a base portion 80 that generally corresponds to the top wall 28 of nasal mask 10. The connector segment 52 further has an upper sidewall segment 82 that generally depends down from the base portion 80. The base portion 80, or top wall 28, in cooperation with the upper sidewall segment 82 defines an internal area that cooperates with the internal area defined by the housing body segment 50 to define the internal cavity 30.

Similar to the lower sidewall segment 56 of the housing body segment 50, the upper sidewall segment 82 defines a front wall section 84, a rear wall section 86, a first end wall section 88 and a second end wall section 90. As further shown, the front wall section 84 has a shorter length dimension than the rear wall section 86. The front wall section 84 has a broad concave lower perimeter. The upper sidewall segment 82 has a proximal end that is integrally connected to the base portion 80 and top wall 28. These connections further define the first shoulder 32 and the second shoulder 34 at respective interface areas between the top wall 28 and the upper sidewall segment 82. A free depending end of the upper sidewall segment 82 defines the second connection surface 94. The second connection surface 94 also defines an inclined surface and adjacent a planar surface. These surfaces generally correspond and mirror the connection surface of the first connection surface 66.

It is understood that the second connection surface 94 could take various other configurations such as a planar surface, angled surface or a combination thereof. Generally, the second connection surface 92 has a cooperative configuration to be operably connected to the first connection surface 66. The second connection surface 94 is closer in proximity to the top wall 28 at the front wall section 84 than the second connection surface 94 at the rear wall surface 86. In addition, as can be appreciated from FIG. 42, the second connection surface 94 slopes downwardly from the front wall section 84 towards the rear wall section 86. The second connection surface 94 slopes generally along a linear path. As further shown in FIG. 48, the upper sidewall segment 82 has a second thickness $t_2$ of 0.070 inches in one exemplary embodiment. It is understood that the thickness can be varied. In addition, the top wall 28 has a thickness of 0.070 inches. The upper sidewall segment 82 has the second thickness $t_2$ that is generally equal to the first thickness $t_1$ of the lower sidewall segment 56 in this exemplary embodiment. Also, the second connection surface 94 is dimensioned to correspond to the lower sidewall segment 56. Similar to certain of the previous embodiments, the sidewall 16 is generally a straight and conical configuration. In other exemplary embodiments, the sidewall 16 may have a thickness of 0.080 inches or approximately 0.075 inches. The housing body segment 50 may have a part material volume of 0.551 cubic inches. In an exemplary embodiment, the connector segment 52 may have a part material volume of 0.544 cubic inches.

Figure 43:
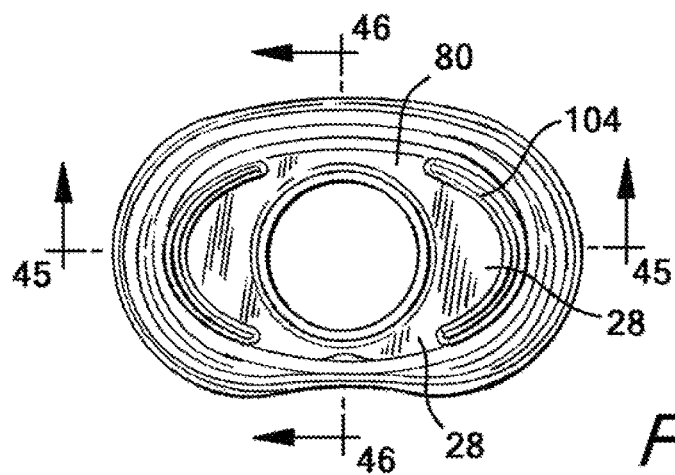
FIG. 43 is a top plan view of the nasal ventilation mask of FIG. 38
Figure 44:
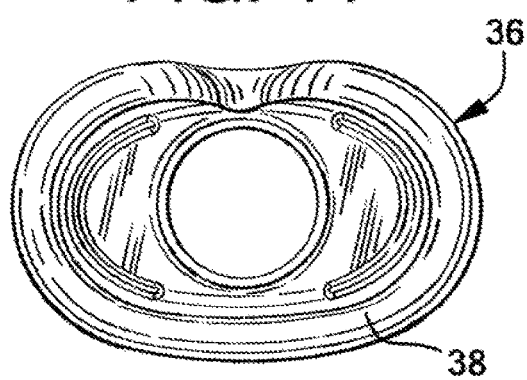
FIG. 44 is a bottom plan view of the nasal ventilation mask of FIG. 38

As further shown in FIGS. 38-43, the base portion 80 of the connector segment 52 has a gripping member 103 in the form of a pair of ridges 104. A ridge 104 is positioned proximate the first shoulder 32 and another ridge 104 is positioned proximate the second shoulder 34 (FIG. 40). The ridges 104 are dimensioned to provide an anti-slip finger gripping feature for operator convenience for forcing and holding the mask firmly against the patient's face. As shown in FIG. 43, the ridges 104 are positioned slightly inward from an outermost outer periphery of the top wall 28. The ridges 104 extend upwards from the top wall 28 proximate the sidewall 16. In an alternative embodiment, the ridges 104 can extend upwards at a location proximate an imaginary line extending from the inner surface of the sidewall 16. Other locations are also possible. The ridges 104 are generally inward from an outer radius of curvature of the connector segment 52. The ridge 104 can further comprise a plurality of ridges 104 spaced from one another in an exemplary embodiment. The height of the ridges 104 can vary but have a height to be engaged by a user and further to provide a tactile feedback including to a user wearing protective gloves.

Figure 45:
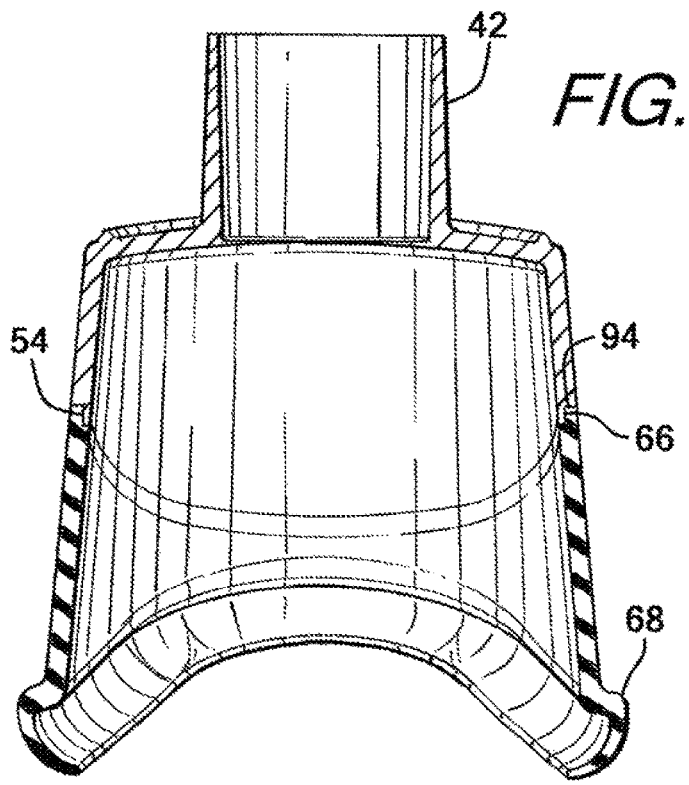
FIG. 45 is a cross-sectional view taken along lines 45-45 of FIG. 43.
Figure 46:
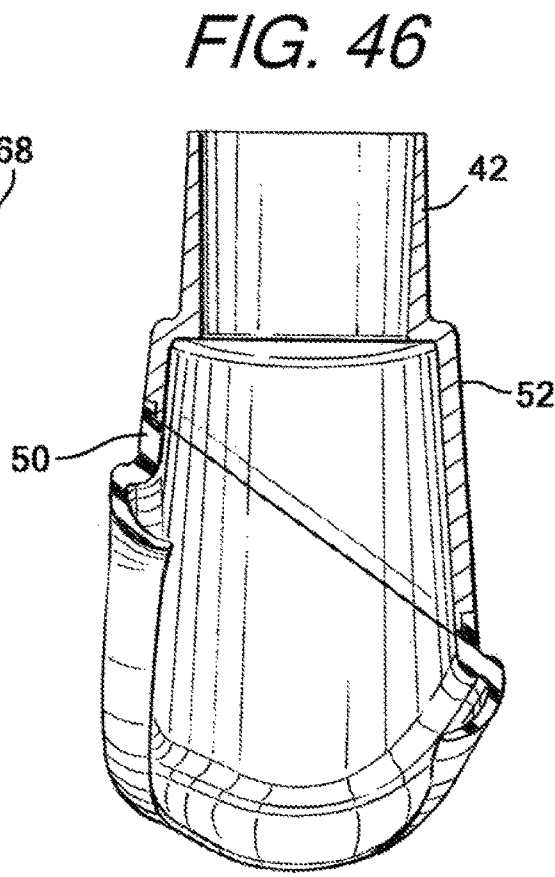
FIG. 46 is a cross-sectional view taken along lines 46-46 of FIG. 43.
Figure 47:
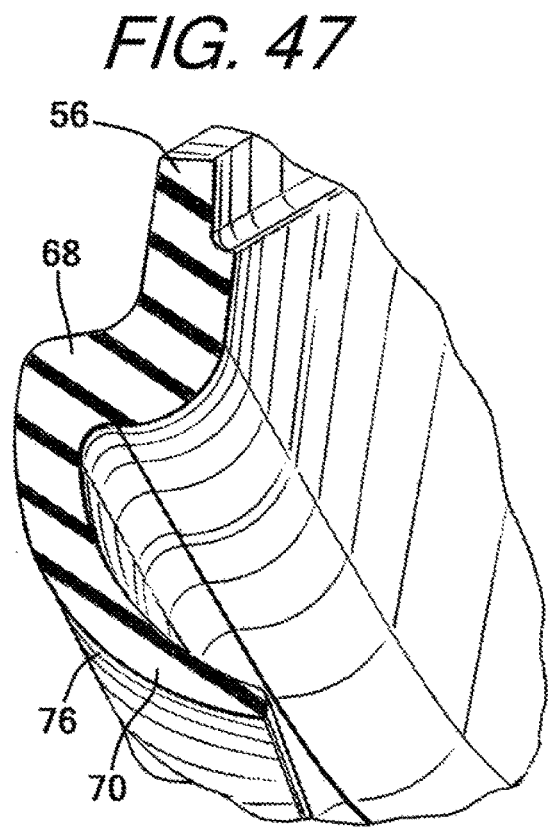
FIG. 47 is an enlarged partial cross-sectional view of a distal end of the nasal ventilation mask of FIG. 38.

FIGS. 45-46 and 48 further disclose details of the connector assembly 14 and receiver member 42. In certain medical standards for respiratory equipment/conical connectors, a 1.432 degree internal diameter taper is specified. An external approximate 1.5 degree taper (draft angle) on the receiver member 42 is utilized for reliable ejection of the part during the molding process. A distal end forming the outlet opening of the receiver member 42 is formed at approximately 0.030 inches. With such parameters, the wall thickness of the receiver member 42 proximate the top wall 28 is approximately 0.074 inches. Modifying the draft angle can result in other desired wall thicknesses. As previously discussed, the receiver member 42 has dimensions to conform to International Standard specifications for socket connectors for respiratory equipment.

As can be appreciated from FIGS. 48, the housing body segment 50 is operably connected to the connector segment 52 to form the nasal ventilation mask 10. When operably connected, the first connection surface 66 and the second connection surface 94 abut and are joined together to form the connection joint 54. The upwardly facing first connection surface 66 of the housing body segment 50 confronts the downward facing second connection surface 94 of the connector segment 52. As in the previous exemplary embodiment, the connection joint 54 is formed via an over-molding injection process wherein the segments 50,52 are joined together. For example, the connector segment 52 can be injection molded in a first mold assembly initially and after completion, placed into another mold assembly. The housing body segment 50 can then be injected molded, or over-molded onto the connector segment 52 resulting in the configuration described above and wherein a chemical bond is formed at the connection joint 54 between the materials of the housing body segment 50 and the connector segment 52. In addition, more complex mold assemblies can be used wherein the housing body segment 50 is molded sequentially during the same overall process as the molding of the connector body segment 52. Other connection methods are also possible such as adhesive bonding or other chemical bonding. Interlocking mechanical connections can also be utilized. Combinations of the above-described connection methods can also be utilized. It is further understood that in a two-shot molding process or over-molding process in forming the housing body segment 50 and connector segment 52, a chemical bond can also be formed between the segments 50,52. A chemical bond is formed between the two segments 50,52 to form the connection joint 54.

FIGS. 38-46 further show the connection joint 54 formed between the housing body segment 50 and the connector segment 52. The connection joint 54 generally has a contoured path around the circumferential sidewall 16. The contoured path provides enhanced operability of the mask 10. The connection joint 54 is more proximate to the top wall 28 at the front wall section 18 of the mask 10 than at the rear wall section 20 of the mask 10. In this exemplary embodiment, the connection joint 54 has a profile in a slanted configuration. In particular, the connection joint 54 generally slopes downwardly along a general linear path at the first end wall section 22 and the second end wall section 24 from the front wall section 18 towards the rear wall section 20. Thus, as can be appreciated from FIGS. 38-39 and 42, at the first end wall section 22 and at the second end wall section 24, the connection joint 54 has the downwardly slanted configuration.

The longer rear wall 86 of the connector segment 52 provides additional rigidity as the connector segment 52 is formed from the more rigid material. The additional rigid material is positioned at the lip area of the patient to minimize local flaring of the mask 10. Thus, the housing body segment 50 has a lesser dimension at the rear wall section 60 corresponding to the area configured to engage proximate the upper lip of the patient, and further has less flex at this area where flaring is undesirable. This configuration still allows the side contours of the mask 10 to flex or flare in a controlled manner to allow for variations in facial contours of patients. Thus, more portions of the nasal mask 10 are formed of the rigid material at strategic locations while the portions of the mask 10 that require flexibility for forming a good airtight seal against the patient's skin are formed of the more flexible material. The slanted connection joint 54 can be considered to have a planar slanted joint 54 as in a plane cutting through the housing body segment 56 at a downward angle. The slanted connection joint 54 achieves these characteristics and it is understood that the connection joint 54 could further have other configurations. The connection joint 54 could have a different slanted configuration or other profile that achieves the similar results to provide an optimal seal against the skin of the patient.

The nasal ventilation mask 10 of FIGS. 38-48 may have an alternative configuration of the sidewall 16 according to another exemplary embodiment of the present invention. This can be appreciated from FIG. 31 showing the sidewall 16 in cross-section and an alternative configuration of the sidewall 16 of the nasal mask 110 having a multiple thickness configuration. The lower sidewall segment 56 of the housing body segment 50 has a larger thickness than the straight-wall thickness of the upper sidewall segment 82 of the connector segment 52. In one exemplary embodiment, the lower sidewall segment 56 can have a thickness of 0.080 inches or 0.075 inches. The thickness of the upper sidewall segment 82 can have a thickness of 0.050 inches or 0.045 inches.

Once formed, the nasal mask 10 of FIGS. 38-48 can also be used with the manual resuscitator bag assembly 1. The nasal mask 10 is used in the same fashion as described above wherein emergency responders press the mask against the face of the patient as can be appreciated from FIGS. 33-37. The supply of breathing gas can be delivered to the patient. The above descriptions regarding operation and functionality apply to the nasal mask 10 of FIGS. 38-48.

Figure 49:
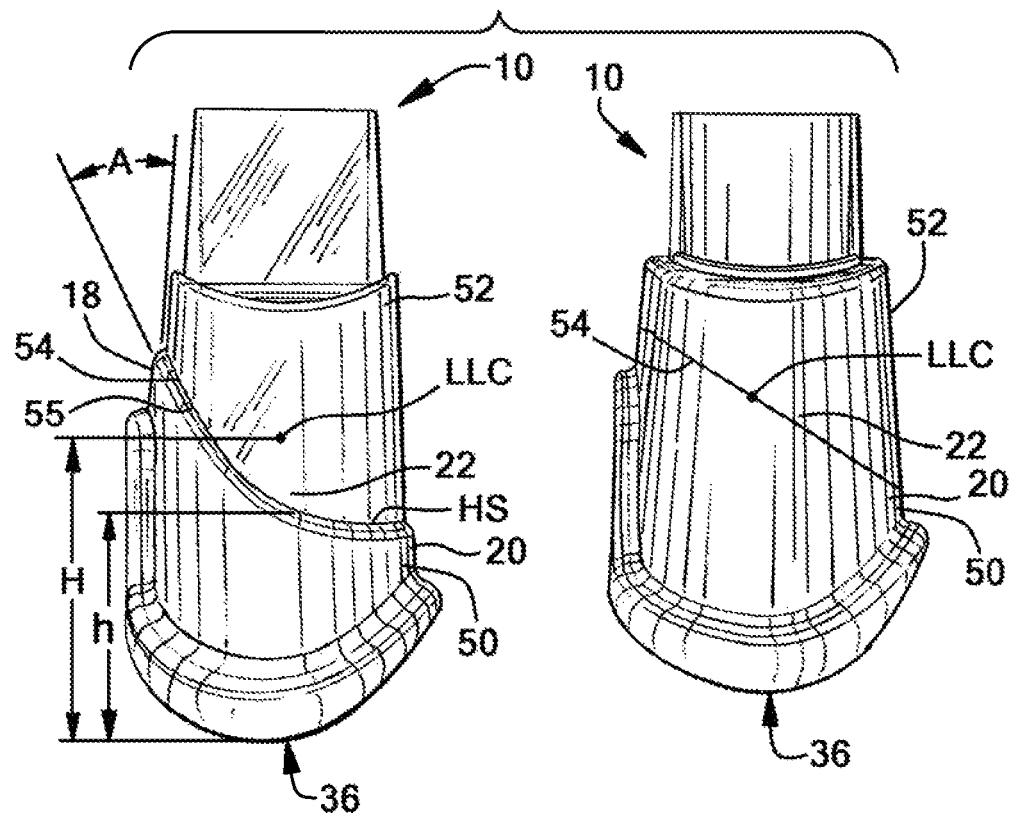
FIG. 49 is a comparison view of side elevation views of the nasal ventilation mask of FIG. 3 and FIG. 38.

As discussed, the exemplary embodiments of FIGS. 3-37 and FIGS. 38-48 utilize a two-piece design forming the connection joint 54. The connection joint 54 is formed between the housing body segment 50 and the connector segment 52. As discussed, the connection joint 54 of FIGS. 3-37 has a profile in a curved-slanted configuration, while the connection joint 54 of FIGS. 38-48 has the more linear slanted profile (or straight, planar slanted profile). FIG. 49 shows comparison side elevation view of the nasal ventilation masks 10 of FIGS. 3-37 (left-side mask 10) and FIGS. 38-38 (right-side mask 10). As shown in FIG. 49, the connection joint 54 of the left-side mask 10 extends from the front wall section 18 towards the rear wall section 20 along a curved line or path, or downwardly sloped line or path rather than a substantially linear configuration shown in the right-side mask 10. It is understood the housing body segment 50 and the connector segment 52 have the corresponding curved-slanted profiles that mate to form the connection joint 54 when operably connected. Thus, at proximate a lateral/longitudinal central portion LLC at respective end wall sections 22,24 of the mask 10, the mask is formed of the more rigid material of the connector segment 52. The lateral/longitudinal central portion LLC is an area on each of the first end wall section 22 and second end wall section 24 located at generally an intersection of a midpoint of a lateral dimension from the front wall section to the rear wall section of the mask and of a midpoint of a longitudinal dimension of an overall height of the mask 10 from the distal end 36 to the inlet opening of the receiver member. This can be appreciated from the left-side mask 10 in FIG. 49. With the curved profile, the more flexible housing body segment 50 is positioned below the lateral/longitudinal central location LLC while the connector segment 52 having more rigid material occupies the lateral/longitudinal central location LLC. This is further appreciated from the comparison of side elevation views in FIG. 49. In the right-side mask 10 having the linear slanted connection joint 54, the connection joint 54 is generally proximate the lateral/longitudinal central portion LLC of the end wall sections 22,24 of the mask 10 wherein the connection joint 54 may generally pass through the lateral/longitudinal central portion LLC of the end wall sections 22,24 of the mask 10. As shown in the left-side mask 10 in FIG. 49, in a slanted connection joint configuration, a height H would be defined from the distal end 36 to the lateral/longitudinal central portion LLC. With the curved-slanted connection joint 54, a lesser height h is defined from the distal end to a top portion of the housing body segment 40 at a lateral central portion of the mask 10. It is understood that the height H is greater than the height h, wherein the housing body segment 50 remains below the lateral/longitudinal central portion LLC of the mask 10. In certain exemplary embodiments, the height H may be approximately 1.088-1.089 inches, while the height h is approximately 0.741 inches. With the lower height h, the mask 10 is formed of the more rigid material of the connector segment 52 at a larger area of the first end wall section 22 and second end wall section 24 of the of the mask 10. This configuration assists in further stabilizing the mask 10 and resists undue flaring when pressing the mask 10 against a patient's skin during use. Thus, the configuration provides for more controlled flexibility of the mask 10 at the end wall sections 22,24 to accommodate varying patient facial contours while still providing for an enhanced seal against the face of the patient. Such configuration further provides material cost-saving benefits. In one exemplary embodiment, the curved slanted profile of the connection joint 50 is the result of a conic profile that travels linearly from one side of the mask body to the other side of the mask body in a path generally normal to a central plane of symmetry of the mask body. As discussed, the curved or downwardly sloped profile of the connection joint 54 could take other forms as well. The connection joint 54 could also be a radial curve or some arc of a circle. It is understood that the housing body segment 50 and the connector segment 52 have the corresponding and confronting curved slanted profiles. It is further understood that the linear slanted connection joint 54 of the right-side mask 10 also provides a greater amount of rigid material on the connection segment 52 on the end wall sections 22,24 (as opposed, for example, of a straight annular connection joint 54). The curved/slanted connection joint 54 provides more enhanced functionality over the linear slanted connection joint 54.

Referring to FIG. 49, with the curved slanted connection joint 102, the connection joint 54 may be considered to have a generally conic curve profile at the end wall sections 22,24 of the mask 10. As shown in the side elevation view, the connection joint 54 profile extends, or swings, or slopes downwardly from approximately an angle A of approximately 30° from a vertical axis at the front of the mask 10. The connection joint 54 continues sloping downwardly to an approximately horizontal profile proximate the rear wall section 20 of the mask 10. Thus, from the side elevation view, the connection joint 54 has the downwardly sloped profile from the front wall section 18 of the mask 10 to the rear wall section 20 of the mask 10. This profile may be considered to look like or resemble a ski slope shape. Thus, at the end wall sections 22,24, the connection joint 54 has a sloped segment SS and a substantially horizontal segment HS. As is further appreciated from the side elevation view, the housing body segment 50 has lesser dimensions on the end wall sections 22,24 wherein the mask 10 has more rigid material of the connector segment 52 on the end sections 22,24. Overall, the connection joint 54 has a concave configuration at the front wall section 18 and a generally horizontal configuration at the rear wall section 20 while having the curved slanted configuration as described on the end wall sections 22,24. It is further understood that the curved slanted configurations of the connection joint 54 at the end wall sections 22,24 have the downwardly sloped segment and a substantially horizontal segment more proximate to the rear wall section 20. It is recognized that the linear slanted joint 54 of the right-side mask 10 in FIG. 49 has a housing body segment 52 having a greater height dimension at the end wall sections 22,24. It is also recognized that the curved slanted connection joint 54 also results in a more pronounced arch profile on the front wall section 18 of the mask 10. The slanted connection joint 54 has a shallower arch as shown in the front elevation view of FIG. 40. The curved slanted connection joint 54 further has more bowed out front and back surfaces of the mask 10, which is more preferred than a true obround footprint with parallel planar surfaces on the front and back surfaces of the mask 10. It is further understood that the segments 50,52 have the cooperating and confronting surface profiles to form the connection joint 54 which results from the conic curve profile travelling from one side of the mask 10 to the other side of the mask 10 in a straight line normal to the plane of symmetry.

The nasal ventilation masks 10 of FIGS. 3-48 utilize many of the same features described herein such as the inwardly curled lip member 70 and the reinforcing member 68. It is understood that the housing body segment 50 in certain exemplary embodiments may have a material part volume of approximately 0.462 cubic inches. Also in certain exemplary embodiments, the connector body segment 52 may have a material part volume of approximately 0.396 cubic inches. The housing body segment 50 may also be formed from the materials described above and further be selected to have a Shore A durometer in the range of 30-40 and, in particular, a Shore A hardness of 30-32 in further exemplary embodiments. It is also contemplated that the overall height of the mask 10 can be increased such as by increasing the height of the shoulders 32,34 approximately 0.125 inches to accommodate patients with varying nose profiles.

Figure 50:
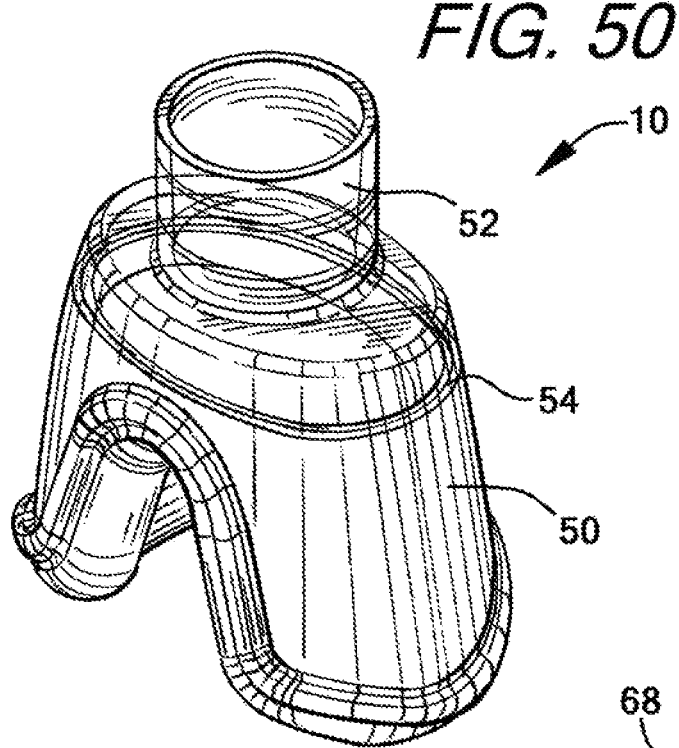
FIG. 50 is a perspective view of another exemplary embodiment of the nasal ventilation mask according to the present invention.
Figure 52:
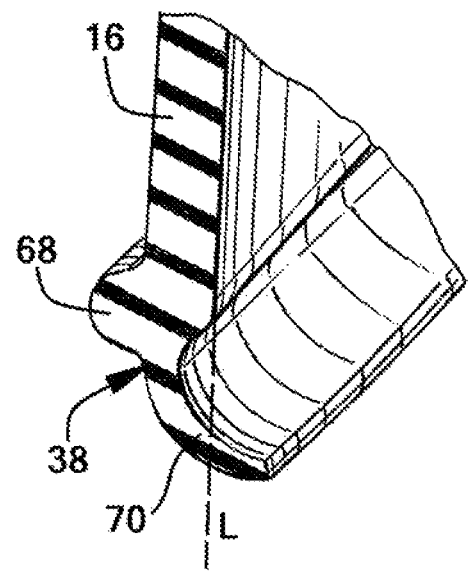
FIG. 52 is a partial enlarged perspective view of the nasal ventilation mask of FIG. 50.
Figure 51:
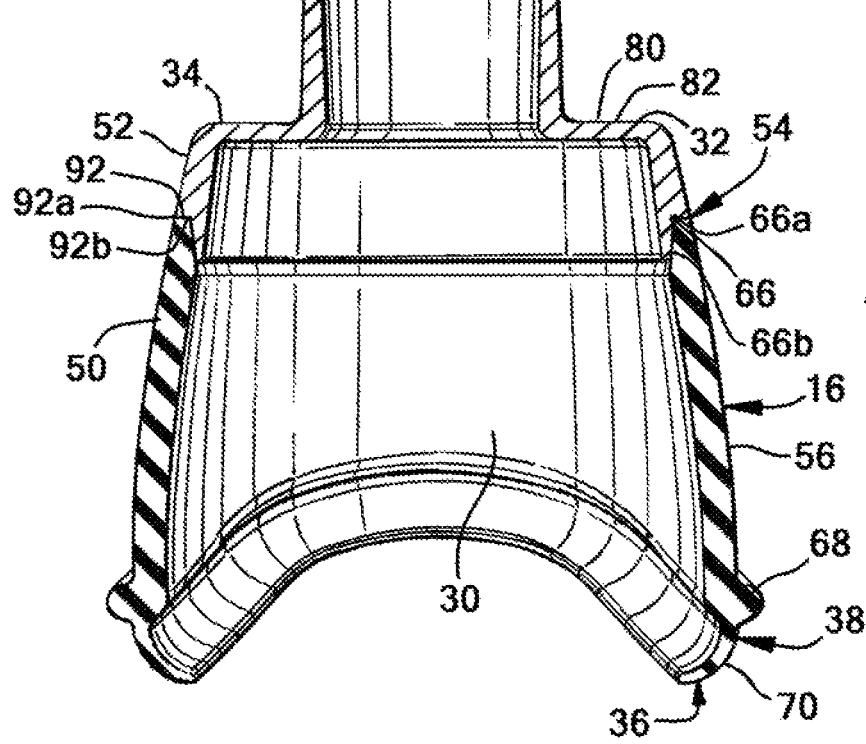
FIG. 51 is a cross-sectional view of the nasal ventilation mask of FIG. 50.

FIGS. 50-52 disclose a nasal ventilation mask according to another exemplary embodiment of the present invention, also generally designated with the reference numeral 10. The nasal mask 10 of FIGS. 50-51 has similar structures to the nasal masks 10 of FIGS. 3-48 described above. Such above descriptions and reference numerals apply to this nasal mask 10. Structural features and functionality that are different from the previously-described embodiments are further described herein. Structural and functional differences are described herein.

As in previous embodiments, the nasal mask 10 of FIGS. 50-52 has a two-piece construction. The nasal mask 10 has the housing body segment 50 and the connector segment 52. The housing body segment 50 is connected to the connector segment 52 to form the connection joint 54 wherein the housing body segment 50 and the connector segment 52 are formed as described above. Once connected as shown for example in FIG. 51, the nasal ventilation mask 10 has generally the same structures and function as described herein. It is understood that the housing body segment 50 defines the distal end 36 as well as the sealing member 38 having the inwardly curled lip member 70. The housing body segment 50 further has the reinforcing member 68 as in the previous embodiments. As can be appreciated from FIG. 51, it is further understood that the connector segment 52 defines the base portion 80, and the first shoulder 32 and the second shoulder 34 as well as the receiver member 42. When connected as described below, the housing body segment 50 and the connector segment 52 cooperate to form components of the nasal mask 10 such as the sidewall 16 and internal cavity 30.

FIG. 51 further disclose the housing body segment 50. As discussed, the housing body segment 50 has the lower sidewall segment 56. The housing body segment 50 has the distal end 36 and the inwardly curled lip member 70 and the reinforcing member 68 are defined proximate the distal end 36 similar to previous embodiments. As further shown in FIG. 51, a free end of the lower sidewall segment of the housing body segment 50 defines the first connection surface 66. As further shown, the first connection surface 66 in this exemplary embodiment further defines an upward facing connector surface 66a and an inclined connector surface 66b. The inclined connector surface 66b is tapered generally towards the inner area cooperatively defining the internal cavity 30 of the mask 10. The housing body segment 50 having the lower sidewall segment 56 has a thickness of 0.125 inches in an exemplary embodiment. As in previous embodiments, the housing body segment 50 is made from a flexible elastomeric material having a low or soft durometer value. In certain exemplary embodiments, the material can be thermoplastic polyurethane (TPU) or low durometer silicone. In further examples, such materials can have a Shore A hardness in the range of 25-40. In an exemplary embodiment, the housing body segment 50 has a part material volume of 1.042 cubic inches. The housing body segment 50 can also have the obround configuration or approximately obround at the distal end 36.

FIG. 52 further shows the sealing member 38. As discussed, the mask 10 utilizes the reinforcing member 68 that extends outwardly from an outer surface of the sidewall 16.

As previous embodiments, the sealing member 38 in the form of the lip member 70 is integrated with the reinforcing member 68. In this exemplary embodiment, the lip member 70 is generally aligned with the sidewall 16 rather than depending from an outer cantilevered end of the reinforcing member 68. Thus, the proximal end 72 of the lip member 70 is generally within the thickness of the sidewall 16. The distal end 74 of the lip member 70 is curled inwardly and extends past an imaginary line extending from an inner surface of the sidewall similar to previous embodiments. The lip member 70 is also tapered towards the distal end 74. The reinforcing member 68 further has a more contoured outer surface configuration in this embodiment.

FIG. 52 further disclose the connector segment 52. Similar to previous embodiments, the connector segment 52 has the base portion 80. The base portion 80 has the upper sidewall segment 82 depending from the base portion 80. The base portion 80 and upper sidewall segment 82 cooperate to form the inner area that cooperates to form the internal cavity 30 when connected to the housing body segment 50. The free end of the upper sidewall segment 82 defines the second connection surface 92. The second connection surface 92 further defines a downward facing connector surface 92a and an inclined connector surface 92b. In certain exemplary embodiments, the connector segment 52 has the receiver member 42 supported on the base portion 80. The wall thickness of the receiver member 42 can be in the range of 0.030 inches to 0.045 inches. In certain medical standards for respiratory equipment/conical connectors, a 1.432 degree internal diameter taper is specified. An external approximate 1.5 degree taper (draft angle) on the receiver member 42 is utilized for reliable ejection of the part during the molding process. In one exemplary embodiment, a distal end forming the outlet opening of the receiver member 42 is formed at approximately 0.030 inches in wall thickness. As in previous embodiment, the receiver member 42 is dimensioned to conform to the International Standard specifications for socket connectors for respiratory equipment.

Similar to previous embodiments, the connector segment 52 is made from a more rigid material. In exemplary embodiments, the connector segment 52 can be made from acrylonitrile butadiene styrene (ABS) or polycarbonate. Other rigid materials are also possible. In a further exemplary embodiment, the connector segment 52 has a part material volume of 0.458 cubic inches.

As can be appreciated from FIGS. 50-51, the housing body segment 50 is operably connected to the connector segment 52 to form the nasal ventilation mask 10. The respective connection surfaces 66,92 surfaces form a connection joint 54. The upwardly facing connector surface 66a of the housing body segment 50 confronts the downward facing connector surface 92a of the connector segment 52. The inclined connector surface 66b of the housing body segment 50 confronts the inclined connector surface 92b of the connector segment 52. In an exemplary embodiment similar to the previous embodiments, the connection joint 54 is formed via an over-molding injection process wherein the housing body segment 50 may be over-molded onto the connector segment 52. For example, the connector segment 52 can be molded initially and placed into another mold assembly. The housing body segment 50 can then be injection molded, or over-molded onto the connector segment 52 resulting in the configuration described above and wherein a chemical bond is formed at the connection joint 54. In addition, more complex mold assemblies can be used wherein the housing body segment 50 is molded sequentially during the same overall process as the molding of the connector body segment 52. Other connection methods are also possible such as adhesive bonding or other chemical bonding. Interlocking mechanical connections can also be utilized. Combinations of the above-described connection methods can also be utilized. In this embodiment, the connection joint 54 is circumferential about the mask 10 and follows generally a linear and horizontal path around the periphery of the mask 10. The linear and horizontal configuration continues in the end wall sections 22,24 of the mask 10, rather than having the curved slanted configuration or linear slanted configuration of the other embodiments in FIGS. 3-48.

Once formed, the nasal mask 10 of FIGS. 50-52 can also be used with the manual resuscitator bag assembly 1. The nasal mask 10 is used in the same fashion as described above wherein medical workers press the mask against the face of the patient as can be appreciated from FIGS. 33-37. The supply of breathing gas can be delivered to the patient. The above descriptions regarding operation and functionality apply to the nasal mask 10 of FIGS. 50-52.

Figure 53:
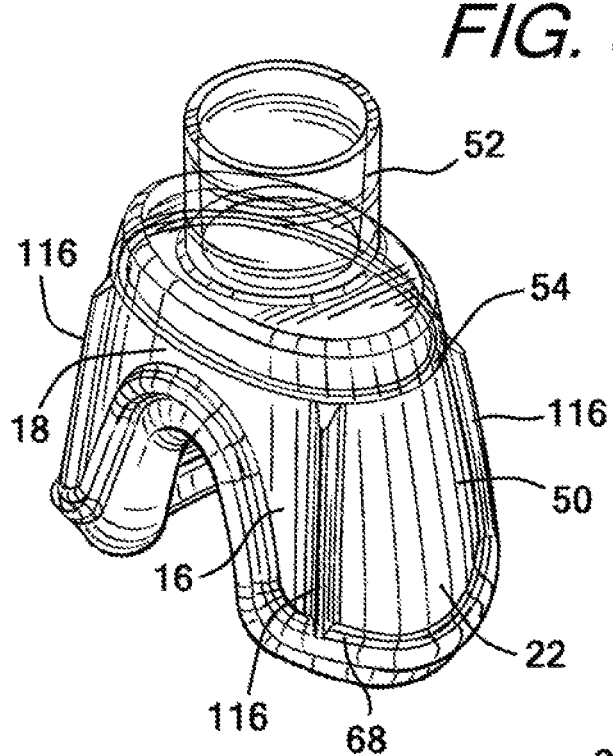
FIG. 53 is a front perspective view of another exemplary embodiment of the nasal ventilation mask according to the present invention.
Figure 54:
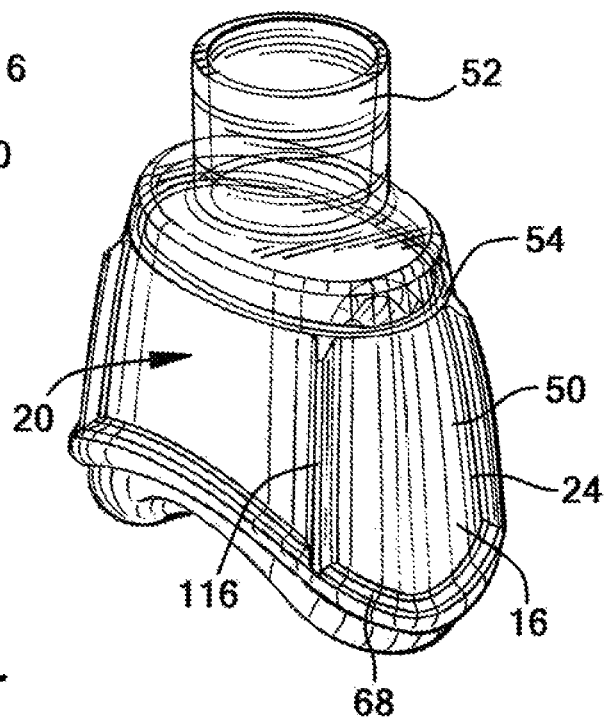
FIG. 54 is a rear perspective view of the nasal ventilation mask of 53.

FIGS. 53-54 discloses a nasal ventilation mask according to another exemplary embodiment of the present invention, also generally designated with the reference numeral 10. The nasal mask 110 of FIGS. 53-54 has similar structures to the nasal masks 10 described above. Such above descriptions and reference numerals apply to this nasal mask 10 as well. Structural and functional differences are described herein.

The nasal ventilation mask 10 of FIGS. 53-54 is a two-piece design having the housing body segment 50 operably connected to the connector segment 52 at the connection joint 54. In this embodiment, the connection joint 54 is also circumferential about the mask 10 and follows generally a linear and horizontal path similar to FIGS. 50-51. In this exemplary embodiment, the housing body segment 50 has a plurality of ribs 116, spaced from one another, and extending longitudinally along the sidewall 16 of the housing body segment 50. The ribs 116 extend upwards from the reinforcing member 68 towards the connector segment 52. In a further exemplary embodiment, the mask 10 includes four ribs 116 spaced around the periphery of the housing body segment 50. The ribs 116 are generally positioned on the front wall section 18 and rear wall section 20 and generally adjacent the end wall sections 22,24 of the mask 10. The ribs 116 provide stiffening properties for the housing body segment 50. Thus, the ribs 116 help minimize buckling, floppiness or other undesired deformation, while allowing desired flexing and stretching when pressing the mask 10 against a patient's skin to achieve an airtight seal during operation as can be appreciated from FIGS. 33-37.

Figure 56:
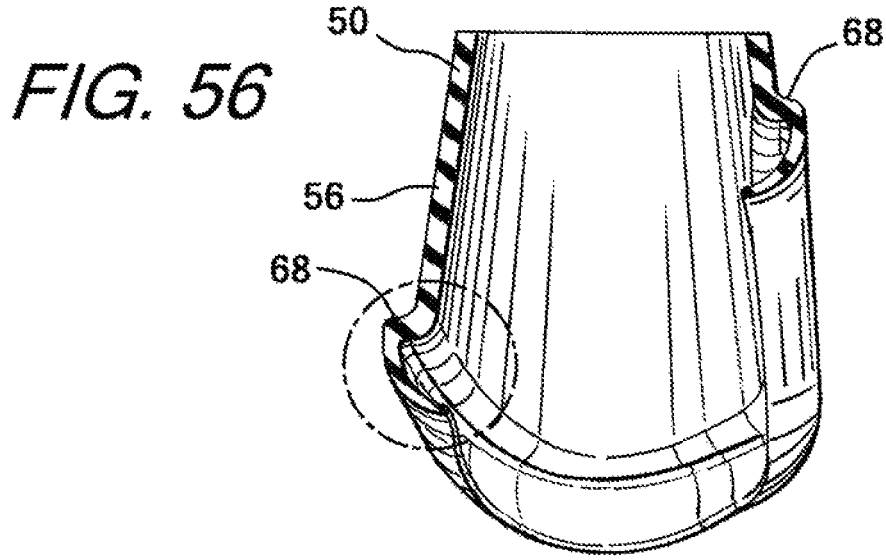
FIG. 56 is a cross-sectional side elevation view of the nasal ventilation mask of FIG. 55.
Figure 57:
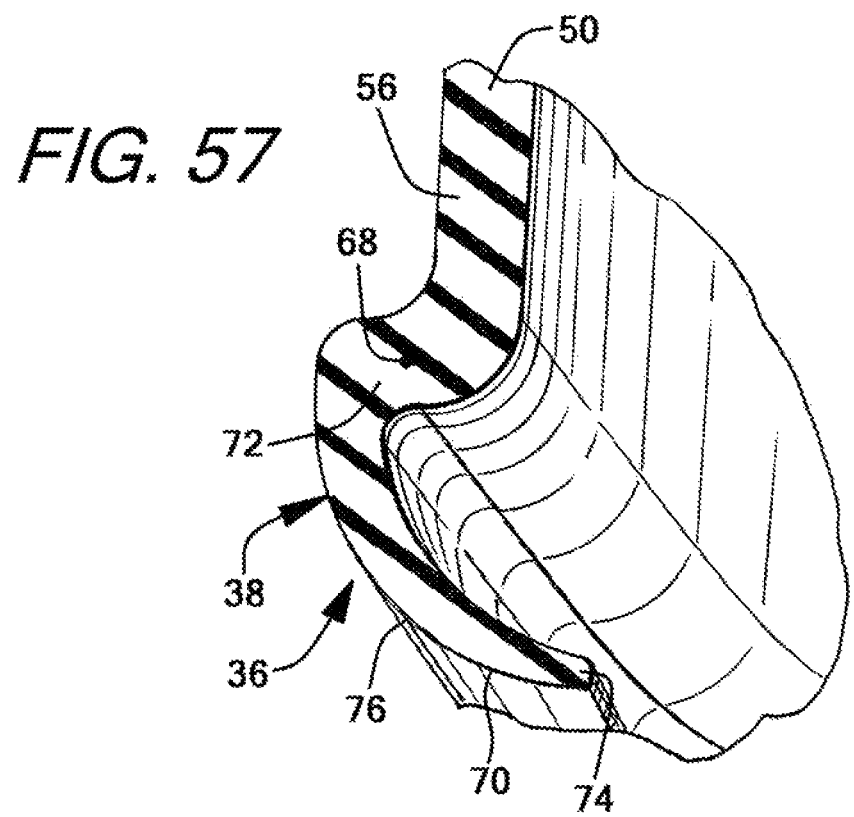
FIG. 57 is a partial enlarged perspective view of the nasal ventilation mask of FIG. 55 and showing a sealing member.
Figure 55:
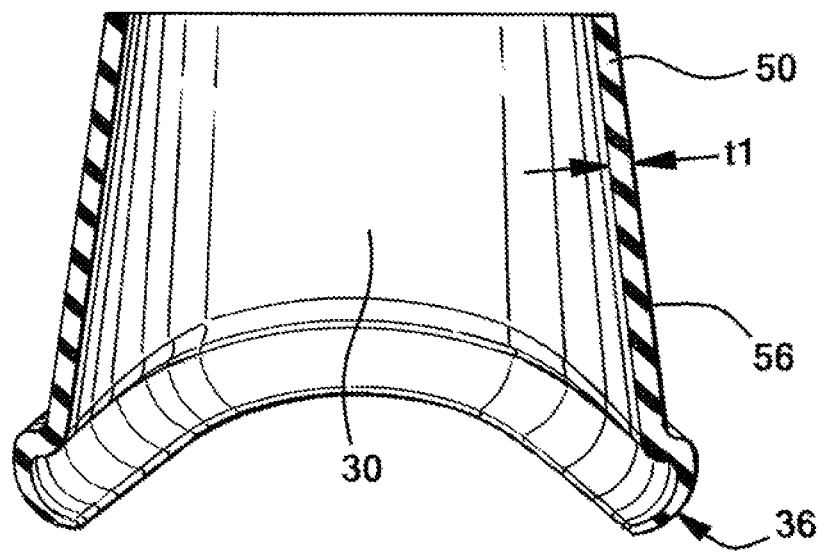
FIG. 55 is a cross-sectional front elevation view of a housing body segment according to another exemplary embodiment of the present invention.

FIGS. 55-57 disclose additional views of a housing body segment 52 according to another exemplary embodiment of the present invention. It is understood that the housing body segment 50 can be utilized with other connector segments 52 of the present invention to form the nasal mask 10. It is understood that in this design, the connection joint 54 formed between the housing body segment 50 and connector segment 52 would be formed along a linear, horizontal path around the sidewall 16 of the mask 10.

FIG. 55 shows a cross-sectional view of the housing body segment 50. The housing body segment 50 has the lower sidewall segment 56 that extends upwards from the distal end 36. The lower sidewall segment 56 has a straight, conical-type configuration. In other embodiments such as shown for example in FIGS. 53-54, the sidewall 16 of the mask 10 has a slightly bowed out configuration. The straight wall configuration of FIG. 55 allows the sidewall 16 to better resist bulging when a user pushes the mask 10 against the face of a patient when creating a seal between the mask 10 and skin of patient. In an exemplary embodiment, the housing body segment 50 has a part material volume of 0.714 cubic inches. In a further exemplary embodiment, the thickness $t_1$ of the lower sidewall segment 56 may be 0.080 inches, or 0.075 inches or approximate thereto. It is understood that the housing body segment 50 may also utilize the stiffening ribs 116 shown in the embodiment of FIGS. 53-54. FIGS. 56-57 further show the distal end 36 of the housing body segment 50. It is understood that the sealing member 38 and reinforcing member 68 have structures and functionality similar to the exemplary embodiment of the nasal ventilation mask 10 shown in FIGS. 3-37, and such descriptions apply to FIGS. 55-57.

Figure 58:
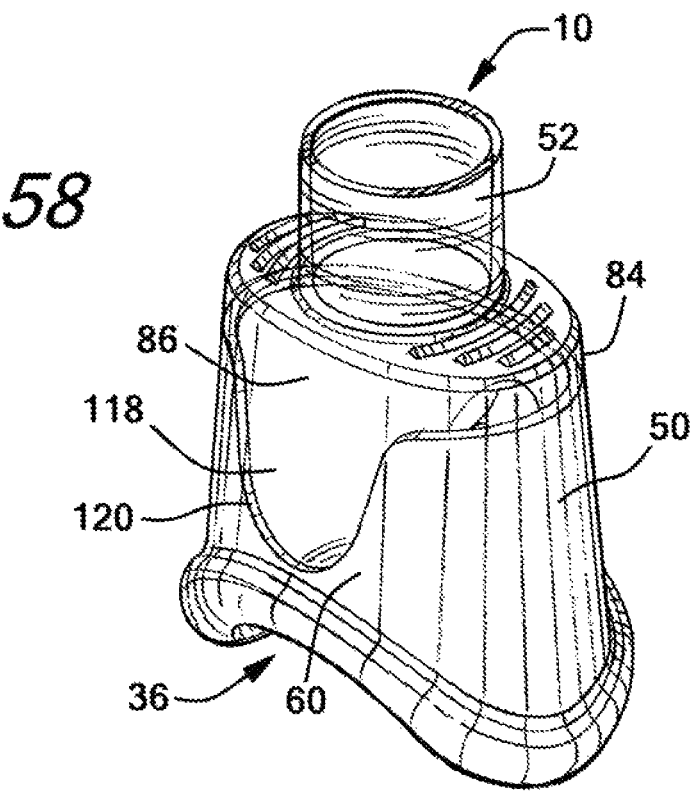
FIG. 58 is a rear perspective view of another exemplary embodiment of the nasal ventilation mask according to the present invention.
Figure 59:
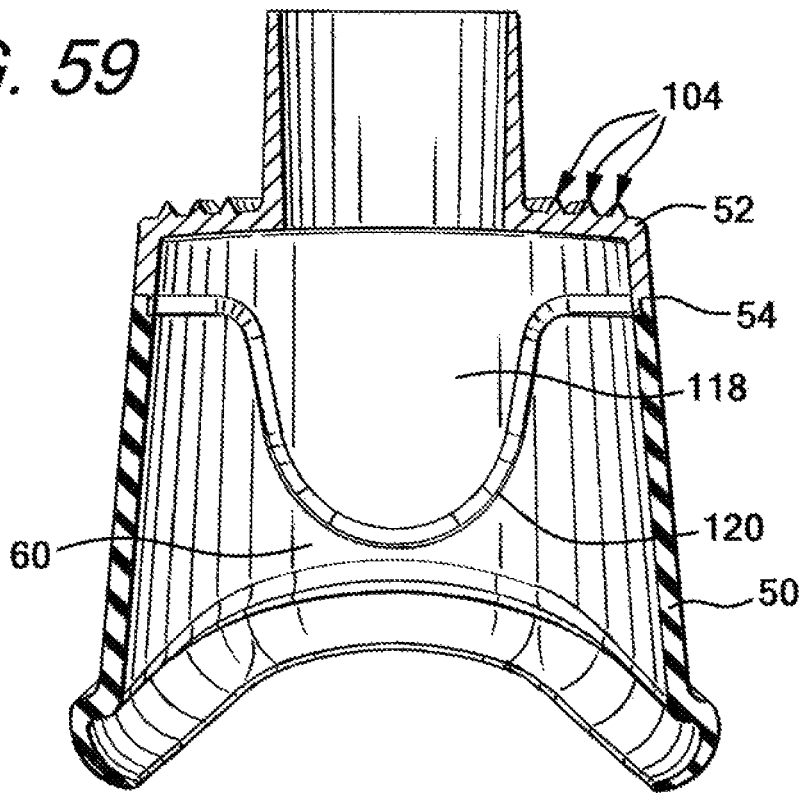
FIG. 59 is a cross-sectional elevation view of the nasal ventilation mask of FIG. 58.

FIGS. 58-59 disclose yet another embodiment of a two-piece nasal ventilation mask 10 having the housing body segment 50 operably connected to the connector segment 52 at the connection joint 54. In this embodiment, the connection joint 54 has an alternative profile. The housing body segment 50 and the connector segment 52 have a modified cooperative structure that forms the connection joint 54. As shown in FIGS. 58 and 59, the rear wall section 86 of the connector segment 52 has an extended length that forms a tongue 118 having a contoured profile. Such length of the tongue 118 is longer than the front wall section 84 of the connector segment 52. The rear wall section 60 of the housing body segment 50 has a lesser dimension at a central area forming a groove 120 to accommodate the tongue 118 of the connector segment 52. As seen in FIGS. 58 and 59, the operable connection between the housing body segment 50 and the connector segment 52 results in the connection joint 54 that extends around a periphery of the mask 10 and further extends towards the distal end 36 at the cooperative tongue 118 and groove 120 structures. The tongue 118 of the connector segment 52 provides additional rigidity as the connector segment 52 is formed from the more rigid material. The additional rigid material is positioned at the lip area of the patient to minimize local flaring of the mask 10. Thus, the housing body segment 52 has a lesser dimension at the area configured to engage proximate the upper lip of the patient, and further has less flex at this area where flaring is undesirable. This configuration still allows the end wall sections 22,24 of the mask 10 to flex and flare allowing for variations in facial contours of patients. Thus, more portions of the nasal mask 10 are formed of the rigid material at strategic locations while the portions of the mask 10 that require flexibility for forming a good seal against the patient's skin are formed of the more flexible material. The modified connection joint 54 utilizing the tongue/groove configuration achieves these characteristics and it is understood that the connection joint 54 could further have other configurations. The connection joint 54 could have a different profile that achieves the similar results to provide an optimal seal against the skin of the patient. Similar to previous embodiments, the connection joint 54 can have an adhesive connection or over-molded configuration and other chemical bonds. It is further understood that the connector segment 52 in any of the embodiments described herein can be made from substantially transparent material wherein workers can see openings of a patient's nostrils through the mask 10. Also, similar to certain of the previous embodiments, the sidewall 16 is generally a straight and conical configuration. As further shown in FIG. 59, the connector segment 52 may have the ridge 104 proximate the shoulders 32,34. In this embodiment, the ridge 104 on each shoulder comprise a plurality of ridges on each shoulder 32,34 to enhance gripping of the mask 10.

Figure 60:
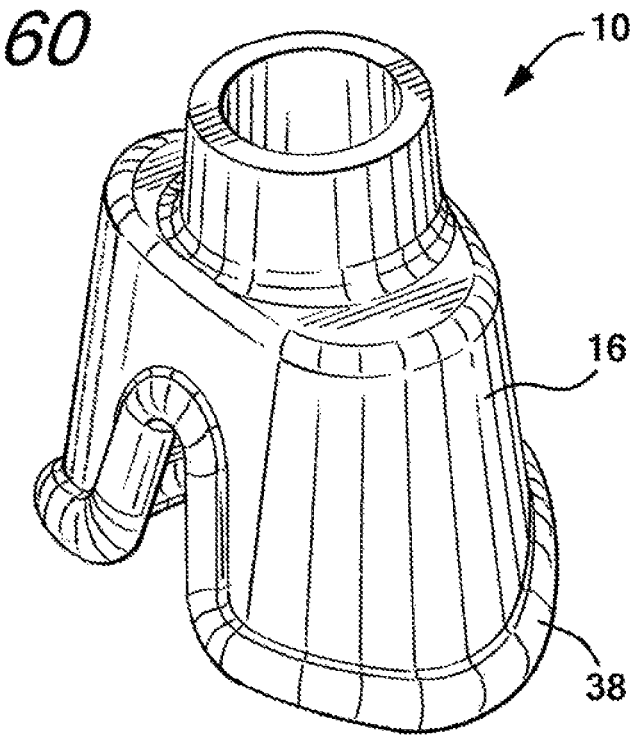
FIG. 60 is a front perspective view of another exemplary embodiment of the nasal ventilation mask according to the present invention.

FIG. 60 discloses a nasal ventilation mask 10 according to another exemplary embodiment of the invention. The nasal mask 10 of FIG. 60 has similar general structure and functionality of the nasal masks 10 described above. In the embodiment of FIG. 60, the nasal mask 10 has the sealing member 38 having the form of the inwardly curled lip member 70 that forms a seal against a patient's face as described above. The nasal mask 10, however, does not utilize the reinforcing member 68 as large in size as shown in the prior embodiments. The nasal mask 10 of FIG. 60 further has a sidewall 16 having a greater thickness dimension. In one exemplary embodiment, the thickness of the sidewall 16 is 0.150 inches or 0.188 inches or approximately 0.150 inches or approximately 0.188 inches. Additional ranges are possible in further exemplary embodiments. It is understood that thickness dimensions of the nasal mask 10 of FIG. 60 could also be used in a housing body segment 50 of two-piece nasal mask designs.

Figure 61:
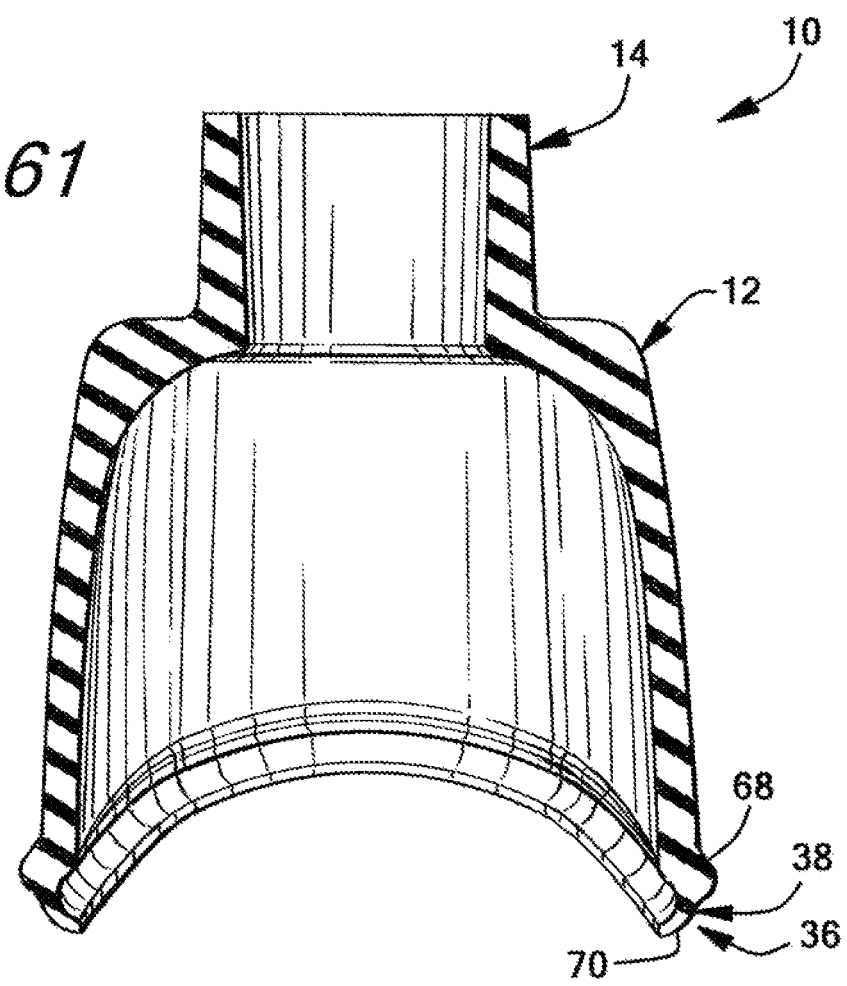
FIG. 61 is a cross-sectional front elevation view of another exemplary embodiment of the nasal ventilation mask according to the present invention.
Figure 62:
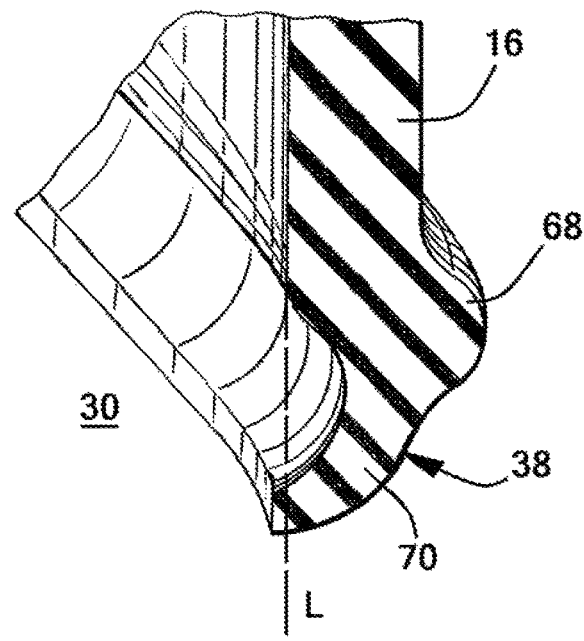
FIG. 62 is a partial enlarged cross-sectional view showing a sealing member of the nasal ventilation mask of FIG. 61.
Figure 63:
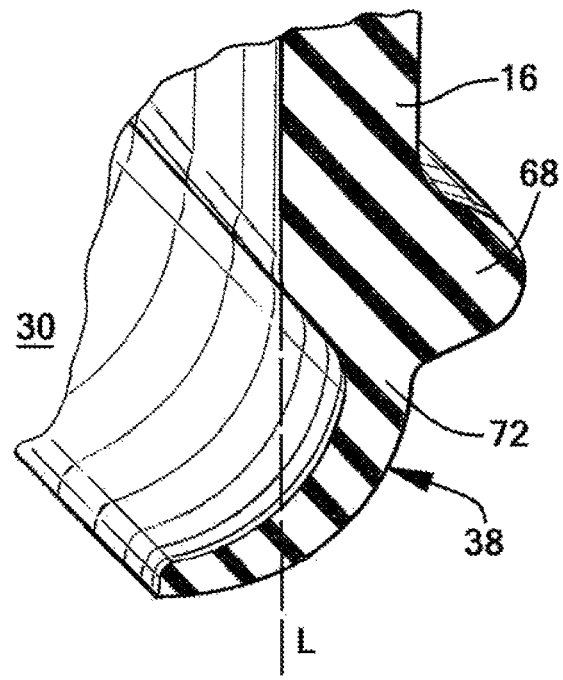
FIG. 63 is a partial enlarged cross-sectional view showing a sealing member of the nasal ventilation mask according to another exemplary embodiment of the invention.
Figure 64:
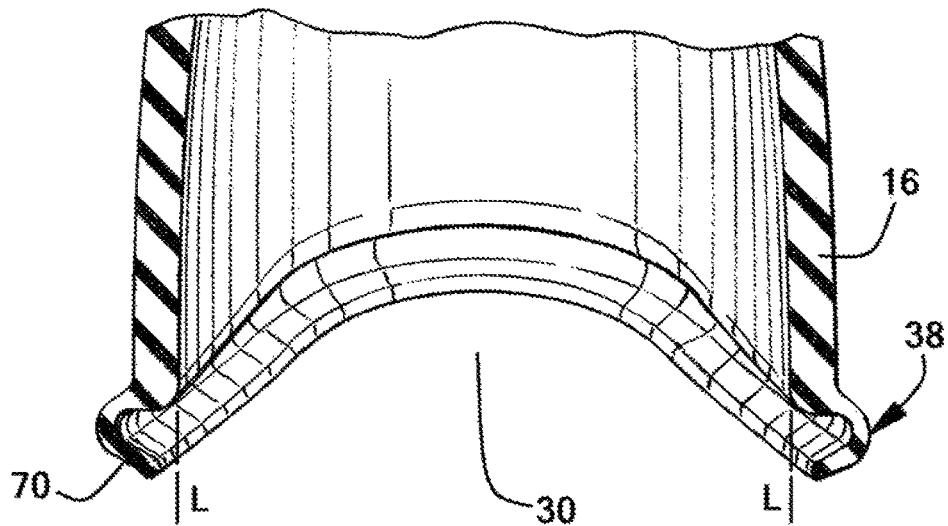
FIG. 64 is a partial enlarged cross-sectional view showing a sealing member of the nasal ventilation mask according to another exemplary embodiment of the invention.

FIGS. 61-64 disclose additional alternative features for the nasal ventilation masks 10 of the present invention. As described in greater detail below, FIG. 61 discloses an additional one-piece nasal mask 10 similar to the nasal mask 10 of FIG. 60. FIGS. 62-64 disclose additional configurations of sealing members 38 according to additional exemplary embodiments of the present invention.

The nasal ventilation mask 10 of FIG. 61 generally includes a housing body 12 and a connector assembly 14 that is connected to the housing body 12. In this exemplary embodiment, the nasal ventilation mask 10 has an integral one-piece injection molded construction similar to the mask 10 shown in FIG. 60. The body 12 and the connector assembly 14 are integral. It is understood, however, that other multi-component designs are possible such as the two-piece designs described herein.

The nasal ventilation mask 10 has similar structural features and functionality as the other masks 10 described herein. Other descriptions generally apply to the exemplary embodiment of FIG. 61. At the distal end 36 of the mask 10, the mask 10 utilizes the reinforcing member 68 and sealing member 38 in the form of the lip member 70. It is understood that the lip member 70 functions as described above.

FIGS. 61 and 62 further show the structural configuration of the sealing member 38 and the reinforcing member 68. Similar to other exemplary embodiments described herein, the sealing member 38 has the lip member 70. In particular, the lip member 70 has the inwardly curled configuration. The inwardly curled lip 70 extends generally into the internal cavity 30. The inwardly curled lip member 70 has a thickness, and the thickness generally tapers to a lesser thickness proximate a distal end of the inwardly curled lip member 70. This tapered thickness assists in ejecting the mask 110 from the mold once molding is complete as the tapered configuration provides a certain amount of flexibility. In an exemplary embodiment, the distal end 74 of the inwardly curled lip 70 extends into the internal cavity 30 approximately even with or just past an imaginary line L extending along the inner surface of the sidewall 16 past the distal end opening 40. In another exemplary embodiment such as shown in FIG. 64, the distal end of the inwardly curled lip 70 extends into the internal cavity 30 but does not extend past an imaginary line L extending along the inner surface of the sidewall 16 past the distal end opening 40. As described herein, the inwardly curled lip member 70 is configured to confront and engage a patient's skin thus providing an engagement portion and seal as described herein. In exemplary embodiments, the distal end of inwardly curled lip member 70 can have a thickness in the range of 0.020-0.025 inches. As further shown in FIGS. 61 and 62, the mask 10 further utilizes the reinforcing member 68. The reinforcing member 68 extends outwardly from an outer surface of the sidewall 16. The inwardly curled lip member 70 is generally aligned with the sidewall 16 in the embodiment shown in FIGS. 61 and 62. Thus, the proximal end 72 of the lip member 70 is positioned within the thickness of the sidewall 16. The reinforcing member 68 extends outwardly from the sidewall 16.

FIG. 63 discloses a sealing member 38 and reinforcing member 68 having similar configurations to FIGS. 61-62. In FIG. 63, the sealing member 68 in the form of the inwardly curled lip member 70 extends into the internal cavity 30. The lip member 70 extends past the imaginary line L extending along the inner surface of the sidewall 16. The reinforcing member 68 has a larger more pronounced structural configuration than the reinforcing member 68 in FIG. 62. The sealing members 38 of FIGS. 62-64 are configured to be pressed against the patient's skin as described herein to form the seal.

The nasal ventilation mask 10 having the one-piece construction can be made from a variety of different materials. In one exemplary embodiment, the mask 10 is made from flexible material such as a flexible elastomer material. Other materials are also possible such as polyethylene, polypropylene and polyvinyl chloride (PVC). With certain materials, the nasal mask 10 may also incorporate additional design modifications. For example, a nasal mask 10 made of certain materials may require a modified seal structure at the distal end 36 of the mask 10.

As discussed, in one exemplary embodiment, the nasal ventilation mask 10 is a one-piece construction. The mask 10 is formed in an injection molding process. The mask 10 is made from a single-durometer resin in an exemplary embodiment. In one exemplary embodiment, the material is of a 35 Shore A durometer. Other durometers are also possible. The mask 10 is sized to fit over the nose of the patient. As described herein, the mask 10 can have multiple sizes to accommodate patients of various ages. The mask 10 can also have one size designed to accommodate the majority of potential patients. Other forming processes could also be used such as thermoforming or blow-molding. Overmolding processes could also be used as well as multiple-shot injection molding processes for more complex designs.

As discussed, the nasal ventilation mask 10 of FIGS. 61-64 has similar functionality as described herein. The mask 10 is operably connected to a manual resuscitator bag assembly 1 wherein a medical worker can press the mask 10 against the patient's face to create a tight seal. Other descriptions herein regarding the functionality of the mask 10 apply to these exemplary embodiments.

The nasal ventilation mask 10 can be used with a manual resuscitator bag assembly 1 as described but could also be used with other components. For example, the nasal ventilation mask 10 can be used with a ventilator or a continuous positive airway pressure machine. Other components can also be operably associated or integrated with the mask such as oxygen monitors or carbon dioxide monitors or other sensors. Depending on desired configurations, the nasal mask 10 may incorporate additional port structures, adapters or other fittings for operable connection to such components. Such operable integrations with other components can be helpful to emergency responders or other medical personnel. For example, integration of a carbon dioxide monitor assists in determining proper ventilation of the patient. Wireless technology can also be operably associated with the nasal mask 10 and such operable connections.

Figure 65:
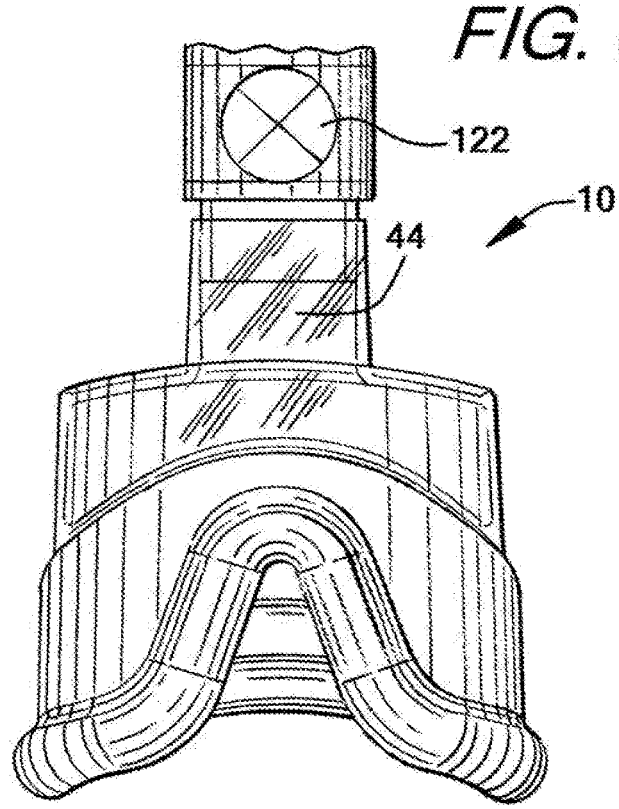
FIG. 65 is a front elevation view of a nasal ventilation mask according to another exemplary embodiment of the invention.
Figure 66:
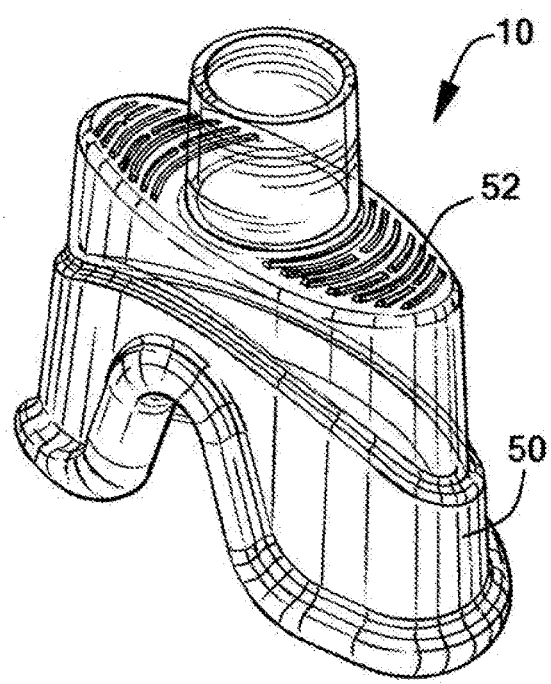
FIG. 66 is a front perspective view of a nasal ventilation mask according to another exemplary embodiment of the present invention.
Figure 67:
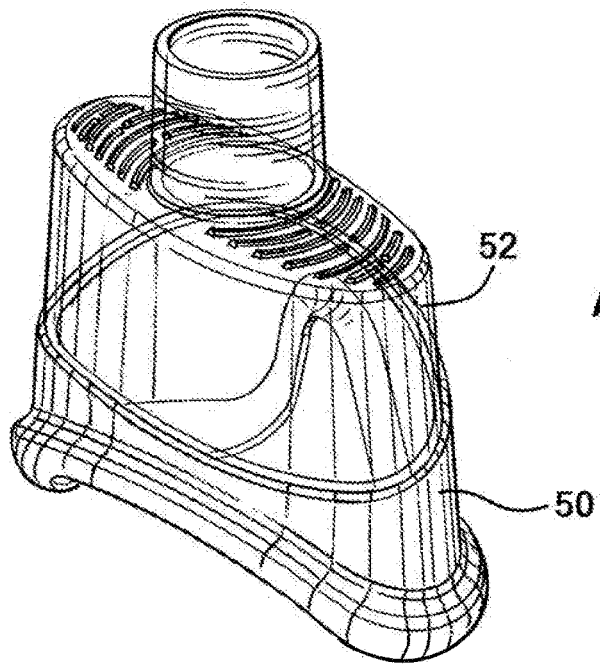
FIG. 67 is a rear perspective view of the nasal ventilation mask of FIG. 66.

The present application discloses multiple embodiments of masks that can be used with a manual resuscitator bag assembly. It is understood that the mask designs described herein can also be used to blow air into an airway of a patient from a medical worker. For example, as shown in FIG. 65, the nasal ventilation mask 10 can have a one-way valve 122 that is operably incorporated into or operably attached to the connector member 42 of the mask 10.

FIGS. 66-74 disclose another embodiment of a two-piece nasal ventilation mask 10 utilizing a housing body segment 50 operably connected to a connector segment 52 at a connection joint 54. The nasal ventilation mask 10 of FIGS. 66-74 utilizes many of the structural features and has similar functionality of the nasal ventilation mask 10 of FIGS. 3-37. As shown in FIGS. 66-74, the nasal mask 10 has the sealing member 38 in the form of the inwardly curled lip member 70 as well as the connection joint 54 having the curved slanted joint at the end wall sections 22,24 of the housing 12 of the mask 10. The mask 10 also utilizes the angled transition connector 92. Thus, the upper sidewall segment 82 of the connector segment 52 is offset inwardly, or positioned radially inwardly, from the lower sidewall segment 56 of the housing body segment 50. The different wall thickness configurations are also utilized. The above descriptions regarding these structures and features apply to the nasal mask 10 of FIGS. 66-74.

Figure 72:
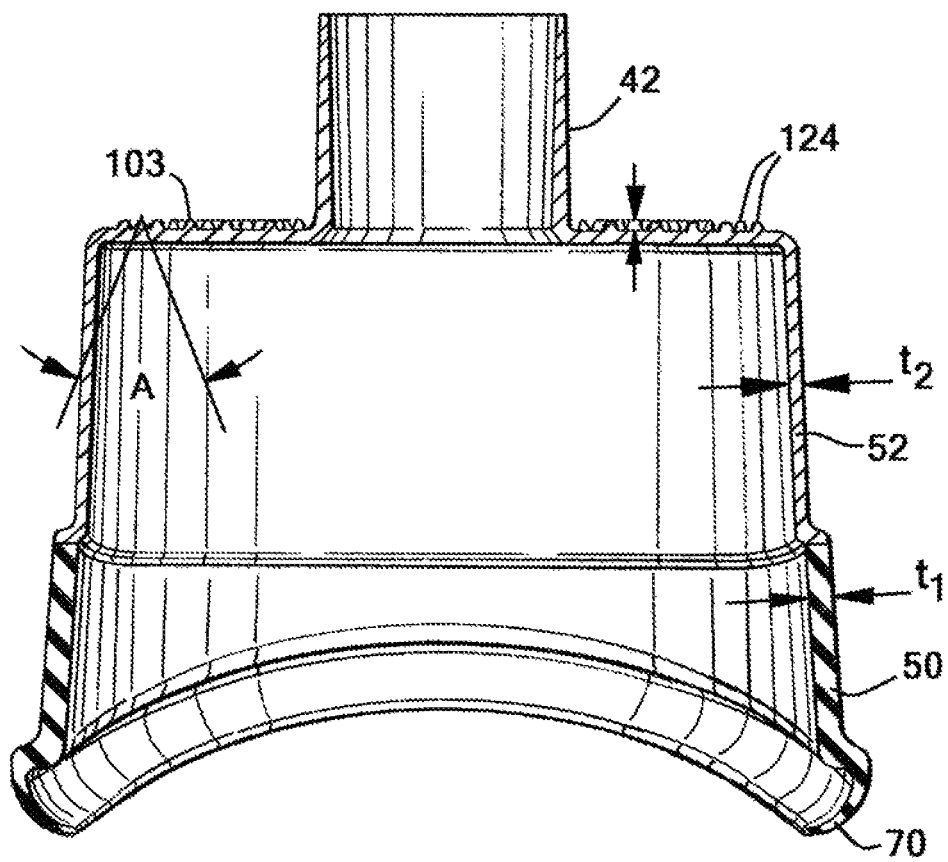
FIG. 72 is a cross-sectional view taken along lines 72-72 of FIG. 70.
Figure 72A:
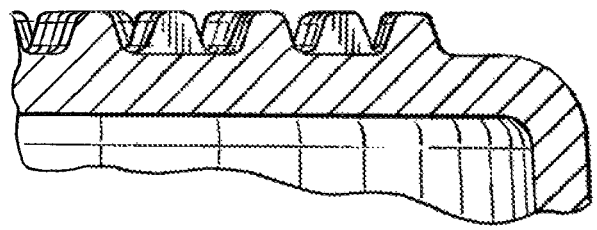
FIG. 72A is an enlarged partial cross-sectional view of a shoulder of the mask and showing gripping members.
Figure 73:
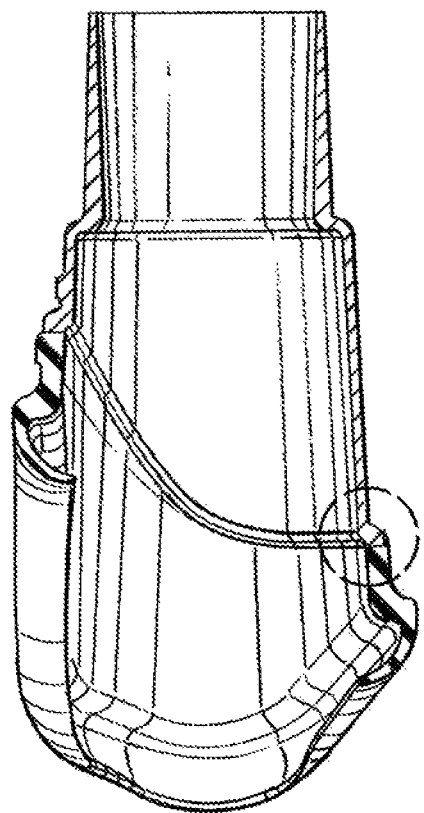
FIG. 73 is a cross-sectional view taken along lines 73-73 of FIG. 70.
Figure 74:
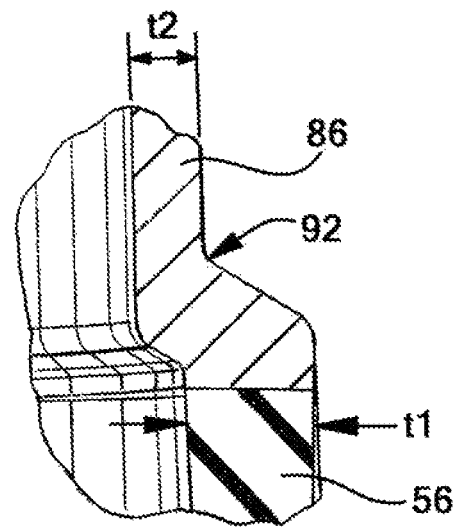
FIG. 74 is a partial cross-sectional view of an angled transition connector associated with a connector segment of the nasal ventilation mask.

As further shown in FIGS. 66-74, the nasal mask 10 has a wider dimension than the nasal mask 10 of FIGS. 3-37 or the nasal mask 10 of FIGS. 38-48. The wider dimension provides for accommodating additional patients having different facial features. Thus, the shoulders 32,34 have a greater surface area allowing for easier engagement by medical personnel when pressing the mask 10 against the face of the user (FIG. 68). As shown in FIGS. 68, 70 and 72, the gripping member 103 is included on the top wall 28. The gripping member 103 is in the form of a plurality of protrusions 124. In one exemplary embodiment, the protrusions are in the form of a truncated cone member. The cone angle may be in the range of 39°-43° or 40° or 41° in a further exemplary embodiment. The height of the protrusion 124 may be approximately 0.040 inches or 0.035 inches. The protrusions 124 provide a user a tactile feedback when engaging the shoulders 32,34 when pressing the mask 10 against the face of the patient. FIG. 72A discloses the protrusions 124 in greater detail. The protrusions 124 may be spaced approximately 0.125 inches from protrusion 124 to adjacent protrusion 124. It is further understood that the protrusions have smooth radiuses for enhanced functionality for emergency responders. Emergency responders wearing protective gloves and engaging the protrusions 124 on the shoulders 32,34 will provide tactile feedback and an enhanced ergonomic configuration for gripping the mask 10 for pressing against the skin of the face of the patient.

FIGS. 75-78 show additional comparison views of nasal ventilation masks 10 according to exemplary embodiments of the present invention. FIGS. 75-78 show three versions that all utilize the two-piece design having the housing body segment 50 connected to the connector segment 52 connected together at a connection joint 54. In the figures, the left-side mask 10 corresponds to the mask of FIGS. 3-37, and the right-side mask 10 corresponds to the mask of FIGS. 66-74. The mask 10 in the middle of each figure is similar to the right-side mask 10 but generally has intermediate dimensions between the left-side mask 10 and the right-side mask 10. For example, the middle mask 10 is wider than the left-side mask 10 but not as wide as the right-side mask 10. The middle mask 10 also utilizes the plurality of protrusions 124 on the top wall 24 of the housing as in the mask 10 of FIGS. 66-74. The masks 10 shown in FIGS. 75-78 all have similar structures and functionality as described herein which further applies to the masks 10 of FIGS. 75-78.

Figure 75:
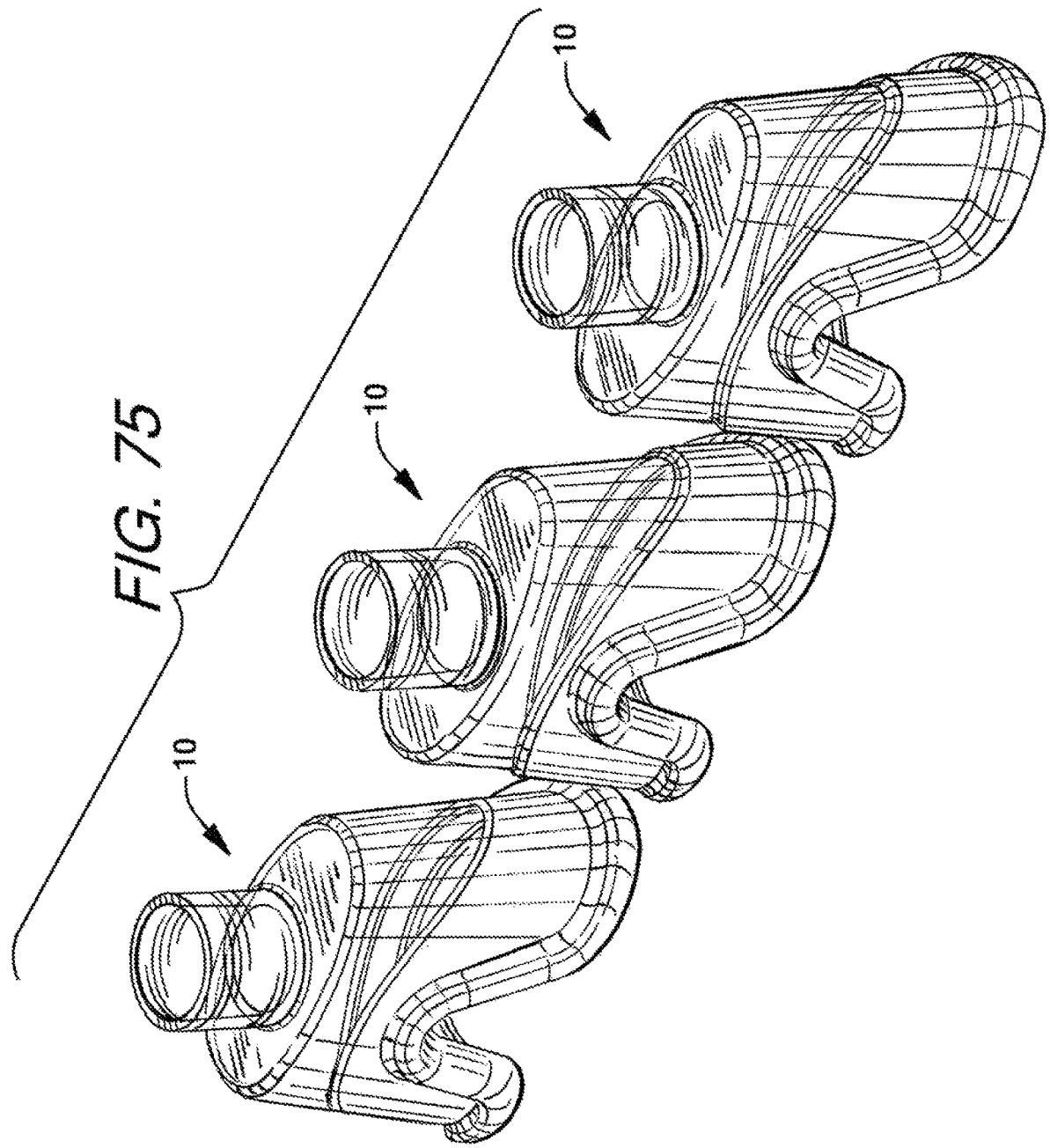
FIG. 75 are front perspective views comparing nasal ventilation masks according to exemplary embodiments of the invention.
Figure 76:
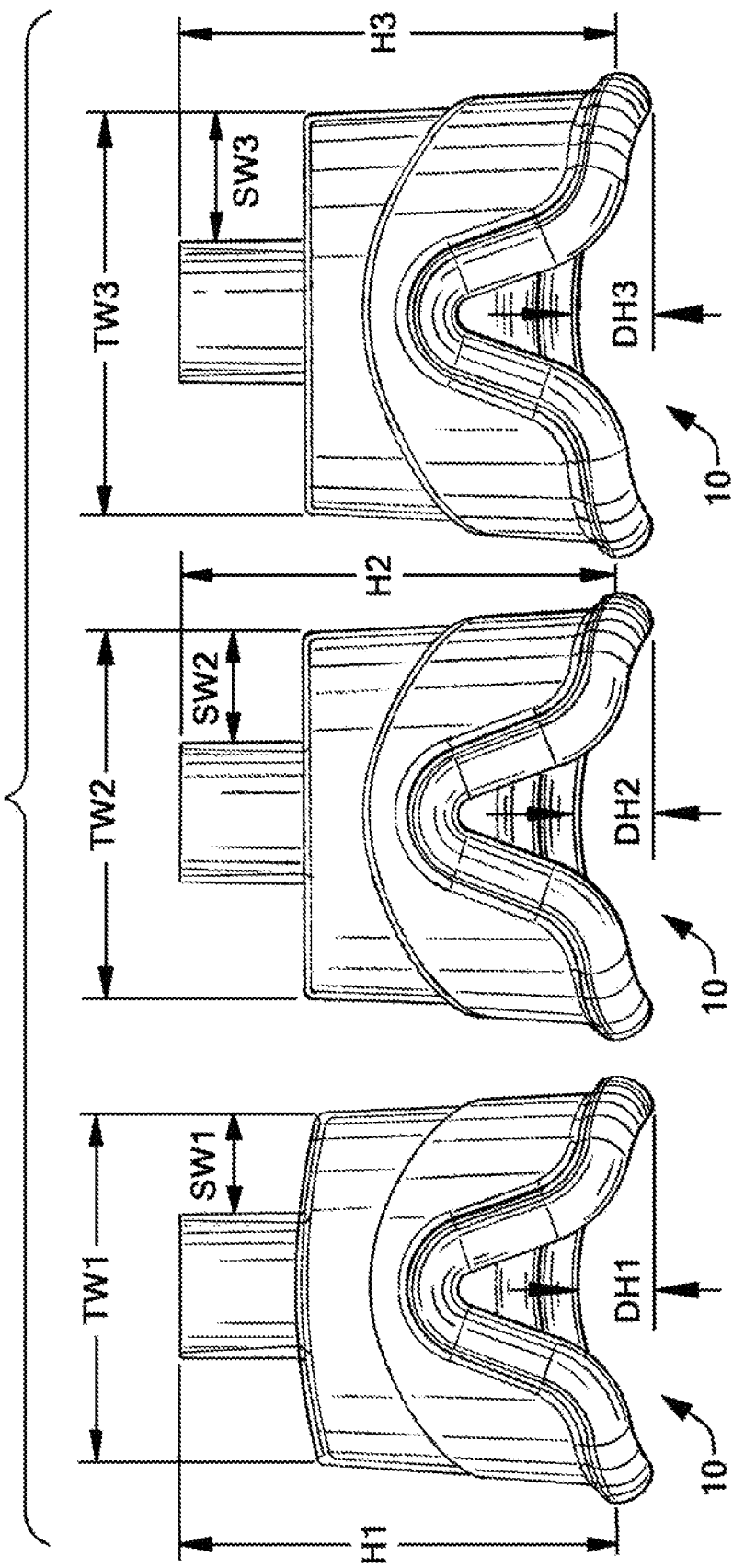
FIG. 76 are front elevation views comparing nasal ventilation masks according to exemplary embodiments of the invention.
Figure 77:
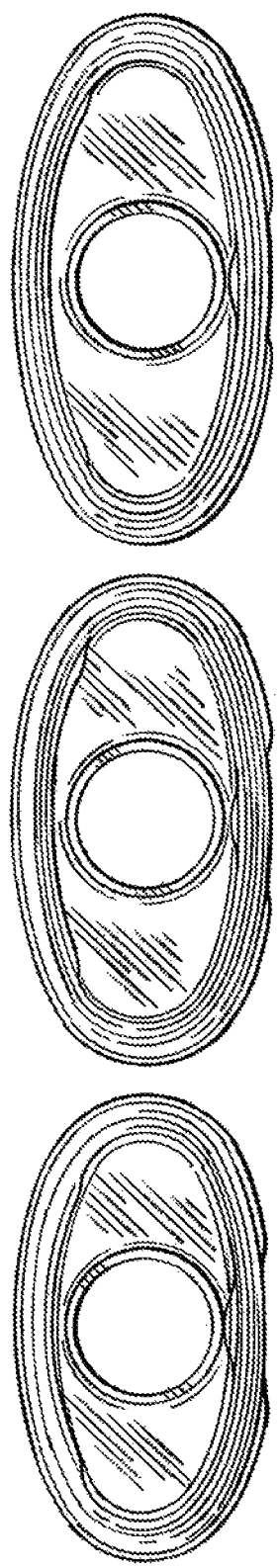
FIG. 77 are top plan views comparing nasal ventilation masks according to exemplary embodiments of the invention.
Figure 78:
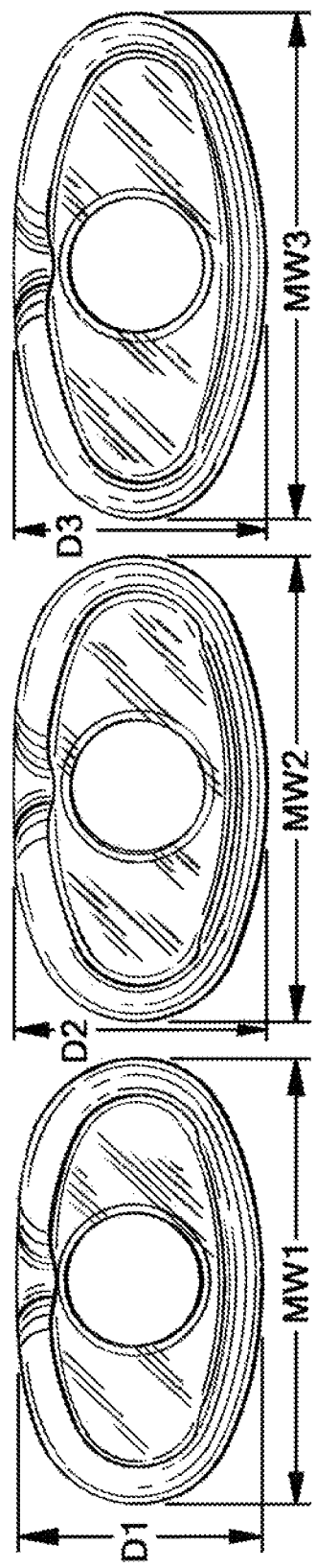
FIG. 78 are bottom plan views comparing nasal ventilation masks according to exemplary embodiments of the invention.

FIG. 75 shows front perspective view of the nasal masks 10. FIG. 76 shows front elevation views of the masks 10. Each mask 10 has a general height H dimension, a top width TW dimension, a shoulder width SW dimension, and a differential height DH dimension, e.g., the height difference between the seal member 38 at the rear wall section 20 and the seal member 38 proximate the end wall sections 22,24. In certain exemplary embodiments, the left side mask 10 may have a height H1 of approximately 2.930 inches, a top wall width TW1 of approximately 2.353 inches, a shoulder width SW1 of approximately 0.685 inches and a differential height H1 of 0.500 inches. Also in certain exemplary embodiments, the middle mask 10 may have a height H2 of approximately 2.930 inches, a top wall width TW2 of approximately 2.479 inches, a shoulder width SW2 of approximately 0.747 inches and a differential height H2 of 0.500 inches. Also in certain exemplary embodiments, the right-side mask 10 may have a height H3 of approximately 2.930 inches, a top wall width TW3 of approximately 2.729 inches, a shoulder width SW3 of approximately 0.872 inches and a differential height H3 of 0.500 inches. FIG. 77 shows top plan view of the masks 10. It is understood that the middle and right-side masks 10 utilize the plurality of protrusions 124. FIG. 78 shows bottom plan views of the masks 10. It is understood that the masks 10 have the housings 12 with end openings 40 defining generally oval footprints. The left-side mask 10 has a mask width MW1 of approximately 2.882 inches and a depth D1 of approximately 1.563. The middle mask 10 has a mask width MW2 of approximately 3.050 inches and a depth D2 of approximately 1.606 inches. The right-side mask 10 has a mask width MW3 of approximately 3.300 inches and a depth D3 of approximately 1.608 inches. It is understood that the right-side mask 10 has the mask width MW3 of the greatest dimension. The mask 10 is able to accommodate more patients having differing facial features.

It is understood that the nasal ventilation mask 10 can be embodied in several different configurations and parameters. In one particular exemplary embodiment, the nasal mask 10 is embodied in the middle mask of FIGS. 75-78. Thus, the mask 10 may have a height H2 of approximately 2.930 inches, a top wall width TW2 of approximately 2.479 inches, a shoulder width SW2 of approximately 0.747 inches and a differential height H2 of 0.500 inches. The middle mask 10 has a mask width MW2 of approximately 3.050 inches and a depth D2 of approximately 1.606 inches. In this configuration, the depth to height ratio may in the range of 53%-57% or approximately 55%. The depth to mask width ratio may also be in the range of 53%-57% or approximately 55%. Finally, a height to mask width ratio may be in the range of 95% to 100% or approximately 96%. The mask 10 in this exemplary embodiment may have a lower side wall thickness of 0.090 inches and an upper sidewall thickness of 0.045 inches. The housing body segment 50 may be made from TPU material being in range of 30-50 or 30-40 Shore A durometer. The lip member having a proximal end thickness of 0.060 inches and a distal end thickness of 0.025 inches. The connector segment 52 is made of ABS material. The mask 10 could also be in an exemplary embodiment having a slightly more narrow configuration wherein the shoulders 32,34 have a slightly smaller dimension. In this exemplary embodiment, Thus, the mask 10 may have a height H of approximately 2.930 inches, a top wall width TW2 of approximately 2.354 inches, a shoulder width SW2 of approximately 0.685 inches and a differential height H2 of 0.500 inches. The mask 10 has a mask width MW of approximately 2.925 inches and a depth D of approximately 1.606 inches. In this configuration, the depth to height ratio may in the range of 53%-57% or approximately 55%. The depth to mask width ratio may also be in the range of 53%-57% or approximately 55%. Finally, a height to mask width ratio may be in the range of 95% to 100% or approximately 100%. The mask 10 in this exemplary embodiment may have a lower side wall thickness of 0.090 inches and an upper sidewall thickness of 0.045 inches. The housing body segment 50 may be made from TPU material being in range of 30-50 or 30-40 Shore A durometer. The lip member having a proximal end thickness of 0.060 inches and a distal end thickness of 0.025 inches. The connector segment 52 is made of ABS material.

It is further understood that in any of the exemplary embodiments described herein, it is desirable for materials of the mask 10 to be as transparent as possible. It is further understood that materials may also be translucent. For example, in two-piece embodiments, the housing body segment 50 may have translucent properties and the connector segment 52 may have transparent properties.

Several embodiments of the nasal ventilation mask are disclosed herein. It is understood that in main exemplary embodiments, the ventilation mask is designed to be placed over a nasal airway of a patient wherein the oral cavity of the patient remains unobstructed as described above. It is understood that many of the features of the specific nasal ventilation mask can be used with a ventilation mask designed to be placed over both the nasal airway and oral airway of a patient.

It is understood that several exemplary embodiments are disclosed and described in the present application. The various exemplary embodiments share certain features and also utilize different features in certain embodiments. It is understood that the various features can be used in various combinations in yet further embodiments.

The ventilation mask or nasal ventilation mask provides several benefits. The sealing structures associated with the mask provide enhanced pneumatic seals between the patient's skin and the mask. The seal is airtight to maintain air pressure within the internal cavity of the mask to efficiently deliver a supply of breathing gas to the patient. The inwardly curled lip provides an enhanced seal in response to force being applied to the mask against the skin of the patient. It is understood that the seal is formed around the fully periphery of the end opening of the mask including the slot wherein the seal is formed at the sides of the nose and the dorsal base of the nose. The nasal ventilation mask has a two-piece construction in certain exemplary embodiments which assists in the mask having rigidity where desired. The mask has flexible portions where needed such in the housing body segment and sealing member and more rigid properties in the connector segment. In other embodiments, the nasal mask has one-piece construction that provides for enhanced operation and can be manufactured efficiently. It is understood that the reinforcing member positioned around the periphery of the housing body segment and proximate the distal end, provides additional stiffening to the body segment. This helps to minimize any undue buckling or deformation when personnel may apply force to the mask 10. In this configuration, the reinforcing member and lip member provide an integrated reinforcing structure that minimizes potential floppiness in the mask. Such integration provides a cleaner, enhanced design as well for allowing more efficient resin flow in the mold when forming the component. The mask further utilizes gripping members to assist in providing tactile feel to medical personnel using the mask on a patient. The structural profile of the mask also provides benefits. The generally oval footprint of the end opening and size/height of the slot to accommodate the patient's nose are dimensioned to provide an enhanced seal against the patient's face. The height of the slot extends only to the dorsal base of the nose rather than extending to a dorsal bridge of the nose closer to eyes of the patient. This minimizes the overall linear surface area of the sealing member required to form the seal. With such structural configuration, a single-sized mask can achieve an airtight seal on multiple sized patients and having varying facial contours. The mask can be successfully used on an infant, child or an adult. It is further understood that masks of different sizes can further be employed to accommodate additional patients of varying age and size.

While the invention has been described in its preferred embodiments, it is to be understood that the words which have been used are words of description rather than limitation and that changes may be made within the purview of the appended claims without departing from the true scope and spirit of the invention in its broader aspects.

What is claimed is:

1. A ventilation mask for supplying breathing gas to an airway of a patient, the ventilation mask comprising: a housing having a sidewall defining an internal cavity and having a peripheral end defining an end opening, the end opening being in fluid communication with the internal cavity, the housing further defining a slot wherein the slot is generally transverse to the end opening, the slot being in fluid communication with the internal cavity, the end opening configured to be positioned over an airway on a face of a patient, a sealing member connected to the housing proximate the end opening and remote from the sidewall, the sealing member extending towards the internal cavity, the sealing member configured to abut the face of the patient and deflect towards the internal cavity, the housing further defining a connector assembly having an opening in fluid communication with the internal cavity, the connector assembly configured to be operably connected to a supply of breathing gas, wherein the housing defines a top wall having a gripping member on the top wall, the gripping member configured to be engaged by medical personnel when pressing the mask against a face of the patient.

2. The ventilation mask of claim 1 wherein the sealing member forms an inwardly curled lip member extending into the internal cavity, the lip member having an outer surface configured to abut the face of the patient.

3. The ventilation mask of claim 2 wherein the lip member has a proximal end and a distal end, the lip member having a thickness being tapered towards the distal end.

4. The ventilation mask of claim 2 wherein the housing defines an internal surface wherein an imaginary line extends from the internal surface past the end opening, wherein a distal end of the lip member extends past the imaginary line.

5. The ventilation mask of claim 2 wherein an outer surface of the inwardly curled lip is smooth and uninterrupted.

6. The ventilation mask of claim 5 wherein the outer surface of the inwardly curled lip has a convex shape.

7. The ventilation mask of claim 2, wherein the lip member extends around a full peripheral of the end opening and slot.

8. The ventilation mask of claim 1 wherein the housing has a reinforcing member extending therefrom proximate the end opening.

9. The ventilation mask of claim 8 wherein the reinforcing member has an outer end, wherein the sealing member defines an inwardly curled lip member having a proximal end depending from the outer end of the reinforcing member.

10. The ventilation mask of claim 9 wherein the housing defines an internal surface wherein an imaginary line extends from the internal surface past the end opening, wherein a distal end of the lip member extends past the imaginary line.

11. The ventilation mask of claim 10 wherein the lip member has a thickness that is tapered towards the distal end.

12. The ventilation mask of claim 11 wherein the housing, reinforcing member and lip member comprise an integral structure.

13. The ventilation mask of claim 8 wherein the sealing member has a proximal end and wherein the proximal end depends from an outer end of the reinforcing member and is offset from the sidewall.

14. The ventilation mask of claim 1 wherein the housing comprises a housing body segment operably connected to a connector segment defining a circumferential connection joint.

15. The ventilation mask of claim 14 wherein the housing defines a front wall section opposite a rear wall section and a first end wall section extending between the front wall section and the rear wall section, wherein the connection joint extends along a downwardly curved path on the first end wall section from the front wall section towards the rear wall section.

16. The ventilation mask of claim 15 wherein the connection joint on the first end wall section has a curved segment adjacent a substantially horizontal segment proximate the rear wall section.

17. The ventilation mask of claim 14 wherein the housing body segment defines a lower sidewall segment and the connector segment defines an upper sidewall segment, the upper sidewall segment positioned inwardly offset from the lower sidewall segment.

18. The ventilation mask of claim 17 wherein the lower sidewall segment has a first thickness and the upper sidewall segment has a second thickness, the first thickness being greater than the second thickness.

19. The ventilation mask of claim 14 wherein the connection joint is a butt joint formed between the housing body segment and the connector segment wherein a chemical bond is formed between the materials of the housing body segment and the connector segment.

20. The ventilation mask of claim 14 wherein the connection joint is comprised of a tongue on one of the housing body segment and the connector segment and a groove on the other of the housing body segment and the connector segment.

21. The ventilation mask of claim 14 wherein the housing body segment is of a thermoplastic polyurethane material.

22. The ventilation mask of claim 14 wherein the connector segment is of an acrylonitrile butadiene styrene material.

23. The ventilation mask of claim 14 wherein a lowermost segment of the connection joint is located on a rear wall section of the housing.

24. The ventilation mask of claim 1 wherein the gripping member comprises a plurality of protrusions, the protrusions configured to be engaged by medical personnel when pressing the mask against a face of the patient.

25. The ventilation mask of claim 1 wherein the end opening defines a substantially oval footprint.

26. The ventilation mask of claim 1 wherein the housing has a plurality of longitudinal ribs spaced thereon.

27. The ventilation mask of claim 1 wherein the gripping member comprises a plurality of protrusions, the protrusions in the form of truncated cones, the truncated cones configured to be engaged by the medical personnel when pressing the mask against the face of the patient.

28. The ventilation mask of claim 1 wherein the slot is in fluid communication with the end opening, wherein when the end opening is configured to be placed over a nasal cavity of a patient, the slot is dimensioned to be positioned proximate a dorsal base of a nose of the patient.

29. A ventilation mask for supplying breathing gas to an airway of a patient, the ventilation mask comprising:
   a housing having a sidewall defining an internal cavity and having a peripheral end defining an end opening, the housing having a reinforcing member extending transversely from an outer surface of the sidewall proximate the end opening, the end opening being in fluid communication with the internal cavity, the end opening configured to be positioned over an airway on a face of a patient,
   a sealing member connected to and depending from an outer end of the reinforcing member proximate the end opening and remote from the sidewall, the sealing member extending towards the internal cavity, the sealing member configured to abut the face of the patient and deflect towards the internal cavity,
   the housing further defining a connector assembly having an opening in fluid communication with the internal cavity, the connector assembly configured to be operably connected to a supply of breathing gas, wherein the housing defines a top wall having a gripping member on the top wall, the gripping member configured to be engaged by medical personnel when pressing the mask against a face of the patient.

30. A nasal ventilation mask for supplying breathing gas to a nasal airway of a patient, the nasal ventilation mask comprising:
   a housing defining an internal cavity and comprising a housing body segment of flexible material operably connected to a connector segment of rigid material defining a circumferential connection joint,
   the housing body segment defining a distal end defining an end opening in fluid communication with the internal cavity, the housing body segment further defining a slot, the slot being in fluid communication with the end opening, the distal end having a sealing member positioned around the end opening and slot, the sealing member forming an inwardly curled lip member extending into the internal cavity,
   the connector segment having a receiver member defining an inlet opening in communication with the internal cavity, the connector segment defining a top wall, the top wall having a plurality of protrusions extending therefrom, and wherein the receiver member extends from the top wall,
   wherein the top wall and protrusions are configured to be pressed towards a face of the patient wherein the lip member is configured to engage the face of the patient and deflect into the internal cavity and configured to create a seal between the face of the patient and the lip member, and wherein the slot is dimensioned to be positioned proximate a dorsal base of a nose of the patient, wherein an inflatable bag of a manual resuscitator bag assembly is configured to be operably connected to the inlet opening of the receiver member of the connector segment such that breathing gas is configured to be delivered to the nasal airway of the patient.

* * * * *